United States Patent
Kelly et al.

(10) Patent No.: US 7,745,451 B2
(45) Date of Patent: Jun. 29, 2010

(54) TETRAHYDRONAPHTHYRIDINE AND TETRAHYDROPYRIDO[4,3-D]PYRIMIDINE COMPOUNDS AND COMPOSITIONS THEREOF USEFUL IN THE TREATMENT OF CONDITIONS ASSOCIATED WITH NEUROLOGICAL AND INFLAMMATORY DISORDERS AND DYSFUNCTIONS

(75) Inventors: Michael G. Kelly, Thousand Oaks, CA (US); John Kincaid, San Mateo, CA (US); Carl J. Kaub, San Jose, CA (US)

(73) Assignee: Renovis, Inc., South San Francisco, CA (US)

( * ) Notice: Subject to any disclaimer, the term of this patent is extended or adjusted under 35 U.S.C. 154(b) by 535 days.

(21) Appl. No.: 11/429,026

(22) Filed: May 4, 2006

(65) Prior Publication Data

US 2006/0258689 A1 Nov. 16, 2006

Related U.S. Application Data

(60) Provisional application No. 60/677,760, filed on May 4, 2005.

(51) Int. Cl.
C07D 471/04 (2006.01)
C07D 487/04 (2006.01)
C07D 413/04 (2006.01)
C07D 413/06 (2006.01)
C07D 295/13 (2006.01)
C07D 209/04 (2006.01)
C07D 209/34 (2006.01)

(52) U.S. Cl. .................. 514/264.11; 544/279; 544/127; 544/162; 544/128; 546/122; 548/491

(58) Field of Classification Search .............. 514/264.1, 514/264.11; 544/244, 279
See application file for complete search history.

(56) References Cited

U.S. PATENT DOCUMENTS

| | | | |
|---|---|---|---|
| 3,248,395 A | 4/1966 | Ohnacker | |
| 3,424,760 A | 1/1969 | Helsley et al. | |
| 3,424,761 A | 1/1969 | Helsley et al. | |
| 7,022,849 B2 | 4/2006 | Pitts et al. | |
| 7,105,667 B2 | 9/2006 | Pitts et al. | |
| 7,232,833 B2 * | 6/2007 | Bigot et al. | 514/314 |
| 2003/0092908 A1 | 5/2003 | Pitts | |
| 2005/0049253 A1 | 3/2005 | Tegley | |
| 2006/0239999 A1 | 10/2006 | Saki et al. | |
| 2006/0252679 A1 | 11/2006 | Saki et al. | |
| 2007/0037834 A1 | 2/2007 | Arai et al. | |
| 2007/0135458 A1 * | 6/2007 | Chen et al. | 514/264.11 |
| 2007/0142402 A1 | 6/2007 | Ding et al. | |

FOREIGN PATENT DOCUMENTS

| | | |
|---|---|---|
| DE | 2502588 | 7/1976 |
| GB | 1033384 | 6/1966 |
| JP | 04224580 A | 8/1992 |
| JP | 2005162673 A | 6/2005 |
| WO | WO 00/69849 | 11/2000 |
| WO | WO 01/32632 A2 | 5/2001 |
| WO | WO 01/44246 A1 | 6/2001 |
| WO | WO 01/62737 | 8/2001 |
| WO | WO 02/08221 | 3/2002 |
| WO | WO 02/22601 A1 | 3/2002 |
| WO | WO 02/22602 A2 | 3/2002 |
| WO | WO 02/22603 A1 | 3/2002 |
| WO | WO 02/22604 A1 | 3/2002 |
| WO | WO 02/22605 A1 | 3/2002 |
| WO | WO 02/22606 A1 | 3/2002 |
| WO | WO 02/22607 A1 | 3/2002 |
| WO | WO 02/22608 A1 | 3/2002 |
| WO | WO 02/50065 A2 | 6/2002 |
| WO | WO 02/053558 | 7/2002 |
| WO | WO 02/057259 A2 | 7/2002 |
| WO | WO 02/059111 A2 | 8/2002 |
| WO | WO 02/062789 A1 | 8/2002 |
| WO | WO 02/087513 | 11/2002 |
| WO | WO 03/062225 A1 | 7/2003 |
| WO | WO 03/076427 | 9/2003 |
| WO | WO 03/104230 | 12/2003 |
| WO | WO 2004/041259 | 5/2004 |
| WO | WO 2004/056774 | 7/2004 |
| WO | WO 2004/087056 A2 | 10/2004 |
| WO | WO 2004/093912 A1 | 11/2004 |
| WO | WO 2005/049033 A1 | 6/2005 |

(Continued)

OTHER PUBLICATIONS

Cockayne, et al., J. Physiol., vol. 567, No. 2, 621-639, Sep. 1, 2005.*

(Continued)

*Primary Examiner*—James O Wilson
*Assistant Examiner*—Cecilia M Jaisle
(74) *Attorney, Agent, or Firm*—Klauber & Jackson LLC

(57) ABSTRACT

Fused heterocyclic compounds are disclosed that have formula 1:

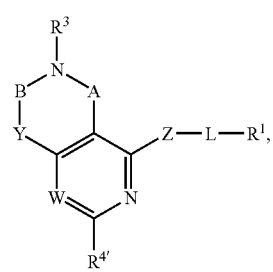

where A, B, L, N, $R^1$, $R^3$, $R^{4'}$, Y and Z are as defined herein. The compounds and pharmaceutical compositions thereof are useful for the prevention and treatment of a variety of conditions in mammals including humans, including by way of non-limiting example, pain, inflammation, cognitive disorders, anxiety, depression, and others.

31 Claims, 1 Drawing Sheet

FOREIGN PATENT DOCUMENTS

| | | |
|---|---|---|
| WO | WO 2006/035061 A1 | 4/2006 |
| WO | WO 2007/070872 A1 | 6/2007 |

OTHER PUBLICATIONS

Raff, et al., Europ. Urology 48 (2005) 303-308.*
Galligan, et al., Brit. J. Pharmacol. (2004) 141, 1294-1302.*
Florenzano, et al., Brain Repair, Chapter 5, 2006, 77-100.*
Willart, et al., Clin. & Experim. Allergy, 39, 12-29 (2008).*
Francis et al., "Anxiolytic Properties of Certain Annelated [1,2,4]triazolo[1,5-c]pyrimidin-5(6H)-ones," *Journal of Medicinal Chemistry*, 34(9):2899-2906 (1991).
Bennett and Xie, 1988, "A Peripheral Mononeuropathy in Rat that Produces Disorders of Pain Sensation Like Those Seen in Man", *Pain*, 33:87-107.
Chaplan et al., 1994, "Quantitative Assessment of Tactile Allodynia in the Rat Paw," *J. Neurosci. Methods*, 53:55-63.
Cockayne et al., 2000, "Urinary Bladder Hyporeflexia and Reduced Pain-Related Behaviour in P2X3-Deficient Mice," *Nature*, 407:1011-1015.
Cockayne et al. 2005, "Urinary Bladder Hyporeflexia and Reduced Pain-Related Behaviour in P2X3-Deficient Mice," *J. Physiol.*, 567:621-639.
Dixon, 1980, "Efficient Analysis of Experimental Observations," *Ann. Rev. Pharmacol. Toxicol.*, 2:441-462.
Dmitrieva et al., 1997, "The Role of Nerve Growth Factor in a Model of Visceral Inflammation," *Neuroscience*, 78:449-59.
Dubuisson and Dennis, 1977, "The Formalin Test: a Quantitative Study of the Analgesic Effects of Morphine, Meperidine, and Brain Stem Stimulation in Rats and Cats," *Pain*, 4:161-174.
Jarvis et al., 2004, "[3H]A-317491, A Novel High-Affinity Non-Nucleotide Antagonist that Specifically Labels Human P2X2/3 and P2X3 Receptors," *J. Pharmacol. Exp. Ther.*, 10:407-416.
Hargrreaves et al., 1988, "A New and Sensitive Method for Measuring Thermal Nociception in Cutaneous Hyperalgesia," *Pain*, 32:77-88.
Kawashima et al., 1998, "A Novel and Efficient Method for the Stable Expression of Heteromeric Ion Channels in Mammalian Cells," *Receptors Channels*, 5:53-60.
Kim and Chung, 1992, "An Experimental Model for Peripheral Neuropathy Produced by Segmental Spinal Nerve Ligation in the Rat," *Pain*, 50:355-363.
Kotinen et al.,1999, "Behavioural Measures of Depression and Anxiety in Rats with Spinal Nerve Ligation-Induced Neuropathy," *Pain*, 80:341-346.
Neelands et al., 2003, "2', 3'-O-(2,4,6,trinitrophenyl)-ATP and A-317491 are Competitive Antagonists at a Slowly Desensitizing Chimeric Human P2X3 Receptor," *Br. J. Pharmacol.*, 140:202-10, 2003.
Polomano et al., 2001, "A Painful Peripheral Neuropathy in the Rat Produced by the Chemotherapeutic Drug, Paclitaxel," *Pain*, 94:293-304.
Stein et al. 1988, "Unilateral Inflammation of the Hindpaw in Rats as a Model of Prolonged Noxious Stimulation: Alterations in Behavior and Nociceptive Thresholds," *Pharmacol. Biochem. Behav.*, 31:451-455.
Vlaskovska et al., 2001, "P2X3 Knock-Out Mice Reveal a Major Sensory Role for Urothelially Released ATP," *J. Neuroscience*, 21:5670-5677.
Wesselmann et al., 1998, "Uterine Inflammation as a Noxious Visceral Stimulus: Behavioral Characterization in the Rat," *Neurosci. Lett.*, 246, 73-76.
Yee, 1997, "In Vitro Permeability Across Caco-2 Cells (Colonic) Can Predict in vivo (Small Intestinal) Absorption in Man—Fact or Myth," *Pharm. Res.*, 14:763-766.
Zhou et al., 1998, "Properties of HERG Channels Stably Expressed in HEK 293 Cells Studied at Physiological Temperature," *Biophys. J.*, 74:230-241.
ISA/US International Search Report dated Sep. 16, 2008, for International Application No. PCT/US2006/017614.
ISA/US Written Opinion of the International Searching Authority dated Sep. 16, 2008, for International Application No. PCT/US2006/017614.

* cited by examiner

TETRAHYDRONAPHTHYRIDINE AND TETRAHYDROPYRIDO[4,3-D]PYRIMIDINE COMPOUNDS AND COMPOSITIONS THEREOF USEFUL IN THE TREATMENT OF CONDITIONS ASSOCIATED WITH NEUROLOGICAL AND INFLAMMATORY DISORDERS AND DYSFUNCTIONS

RELATED APPLICATIONS

This application claims the benefit under 35 U.S.C. §119 of U.S. Provisional Application No. 60/677,760, filed May 4, 2005, incorporated herein by reference in its entirety for all purposes.

FIELD OF THE INVENTION

This invention relates to novel fused heterocyclic compounds of the class tetrahydronaphthyridines and tetrahydropyrido[4,3-d]pyrimidines and to pharmaceutical compositions containing such compounds. This invention also relates to methods for preventing and/or treating conditions in mammals, such as (but not limited to) arthritis, Parkinson's disease, Alzheimer's disease, asthma, myocardial infarction, the treatment and prophylaxis of pain syndromes (acute and chronic or neuropathic), neurodegenerative disorders, schizophrenia, cognitive disorders, anxiety, depression, inflammatory bowel disease and autoimmune disorders, and promoting neuroprotection, using the fused heterocyclic compounds and pharmaceutical compositions of the invention.

BACKGROUND OF THE INVENTION

Therapeutic strategies for the effective management of pain and central nervous system disorders or diseases are sought.

International Patent Application, Publication Number WO 02/08221 discloses diaryl piperazine and related compounds which are said to be useful in the treatment of chronic and acute pain conditions, itch and urinary incontinence.

WO02/053558 describes certain quinazolone derivatives as alpha 1A/B adrenergic receptor antagonists, and WO03/076427 and WO04/041259 both describe compounds of the same class for use in the treatment of female sexual dysfunction. WO04/56774 describe certain substituted biphenyl-4-carboxylic acid arylamide analogues having possible application as receptor modulators. Also, WO03/104230 describes certain bicyclic pyrimidine derivatives, and US Published Application Serial No. 20030092908 and WO02/087513 describe fused heterocyclic PDE7 inhibitors.

U.S. Pat. Nos. 3,424,760 and 3,424,761 both describe a series of 3-ureidopyrrolidines that are said to exhibit analgesic, central nervous system, and pyschopharmacologic activities. These patents specifically disclose the compounds 1-(1-phenyl-3-pyrrolindinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

SUMMARY OF THE INVENTION

Fused heterocylic compounds, and pharmaceutical compositions thereof, having potency and selectivity in the prevention and treatment of conditions that have been associated with neurological and inflammatory disorders and dysfunctions are described herein.

In particular, compounds, pharmaceutical compositions and methods provided are used to treat, prevent or ameliorate a range of conditions in mammals such as, but not limited to, pain of various genesis or etiology, for example acute, chronic, inflammatory and neuropathic pain, dental pain and headache (such as migraine, cluster headache and tension headache). In some embodiments, the compounds, pharmaceutical compositions and methods provided are useful for the treatment of inflammatory pain and associated hyperalgesia and allodynia. In some embodiments, the compounds, pharmaceutical compositions and methods provided are useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). In some embodiments, the compounds, pharmaceutical compositions and methods provided are useful as anti-inflammatory agents for the treatment of arthritis, and as agents to treat Parkinson's Disease, Alzheimer's Disease, asthma, myocardial infarction, neurodegenerative disorders, inflammatory bowel disease and autoimmune disorders, renal disorders, obesity, eating disorders, cancer, schizophrenia, epilepsy, sleeping disorders, cognitive disorders, depression, anxiety, blood pressure, and lipid disorders.

Accordingly, in one aspect, fused heterocyclic compounds are provided that have formula 1:

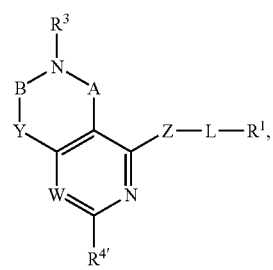

wherein

A and B are independently selected from $CR^2R^{2'}$, CO, and CS;

Y is $CR^2R^{2'}$;

W is selected from $CR^4$ and N;

Z is selected from O and $NR^2$;

L is a bond, substituted or unsubstituted alkylene, or substituted or unsubstituted heteroalkylene;

$R^1$ and $R^3$ independently are a substituted or unsubstituted carbocyclic group or a substituted or unsubstituted heterocyclic group;

$R^2$ is selected from hydrogen, alkyl, cycloalkyl, aryl and aralkyl;

each $R^{2'}$ is selected from hydrogen, substituted or unsubstituted $C_1$-$C_6$ alkyl, substituted or unsubstituted $C_3$-$C_8$ cycloalkyl, substituted or unsubstituted aryl and substituted or unsubstituted aralkyl;

$R^4$ is selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, amino, substituted or substituted aryl, substituted or substituted arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, substituted or substituted heteroaryloxy, substituted or unsubstituted heteroaryl, substituted or unsubstituted heteroalkyl, hydroxy, nitro, and thio; and $R^{4'}$ is selected from $R^4$ and —Z'-L'-$R^4$, wherein Z' is a bond, $NR^{2'}$, O, S, SO, $SO_2$, COO, or $CONR^{2'}$ and L' is $C_1$-$C_6$ alkylene;

or a pharmaceutically acceptable salt, solvate or prodrug, stereoisomer, tautomer or isotopic variant thereof.

In one aspect, a fused heterocyclic compounds is provided having formula 1a:

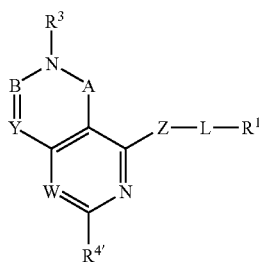

1a wherein

A is selected from $CR^{2'}R^{2'}$, CO, and CS;

each of B and Y is $CR^{2'}$; and

W, Z, L, $R^1$, $R^{2'}$, $R^3$, $R^4$ and $R^{4'}$ are as defined above with regard to formula 1;

or a pharmaceutically acceptable salt, solvate, prodrug, stereoisomer, tautomer, or isotopic variant thereof.

In another aspect, pharmaceutical compositions are provided comprising a fused heterocyclic compound of the invention, and a pharmaceutical carrier, excipient or diluent.

The pharmaceutical composition can comprise one or more of the fused heterocyclic compounds described herein.

It will be understood that fused heterocyclic compounds of the present invention useful in the pharmaceutical compositions and treatment methods disclosed herein, can be pharmaceutically acceptable as prepared and used.

In another aspect, methods are provided for preventing, treating or ameliorating a condition from among those listed herein, and particularly, such condition as may be associated with, e.g., arthritis, asthma, myocardial infarction, lipid disorders, cognitive disorders, anxiety, schizophrenia, depression, memory dysfunctions such as Alzheimers disease, inflammatory bowel disease and autoimmune disorders, which method comprises administering to a mammal in need thereof an amount of one or more of the compounds as provided herein, or pharmaceutical composition thereof, effective to prevent, treat or ameliorate the condition.

In yet another aspect, methods are provided for preventing, treating or ameliorating a condition that gives rise to pain responses or that relates to imbalances in the maintenance of basal activity of sensory nerves in a mammal. The fused heterocyclic compounds provided herein have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In one aspect, methods are provided for preventing, treating or ameliorating a neurodegenerative disease or disorder in a mammal. A neurodegenerative disease or disorder can, for example, be Parkinson's disease, Alzheimer's disease and multiple sclerosis; diseases and disorders which are mediated by or result in neuroinflammation such as, for example, encephalitis; centrally-mediated neuropsychiatric diseases and disorders such as, for example, depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example, psoriasis; obesity; lipid disorders; cancer; and renal disorders Typically, the methods comprise administering an effective condition-treating or condition-preventing amount of one or more of the compounds as provided herein, or pharmaceutical composition thereof, to the mammal in need thereof.

In additional aspects, methods are provided for synthesizing the fused heterocyclic compounds described herein, with representative synthetic protocols and pathways described below.

Other objects and advantages will become apparent to those skilled in the art from a consideration of the ensuing detailed description.

DETAILED DESCRIPTION OF THE INVENTION

Definitions

Figure 1:
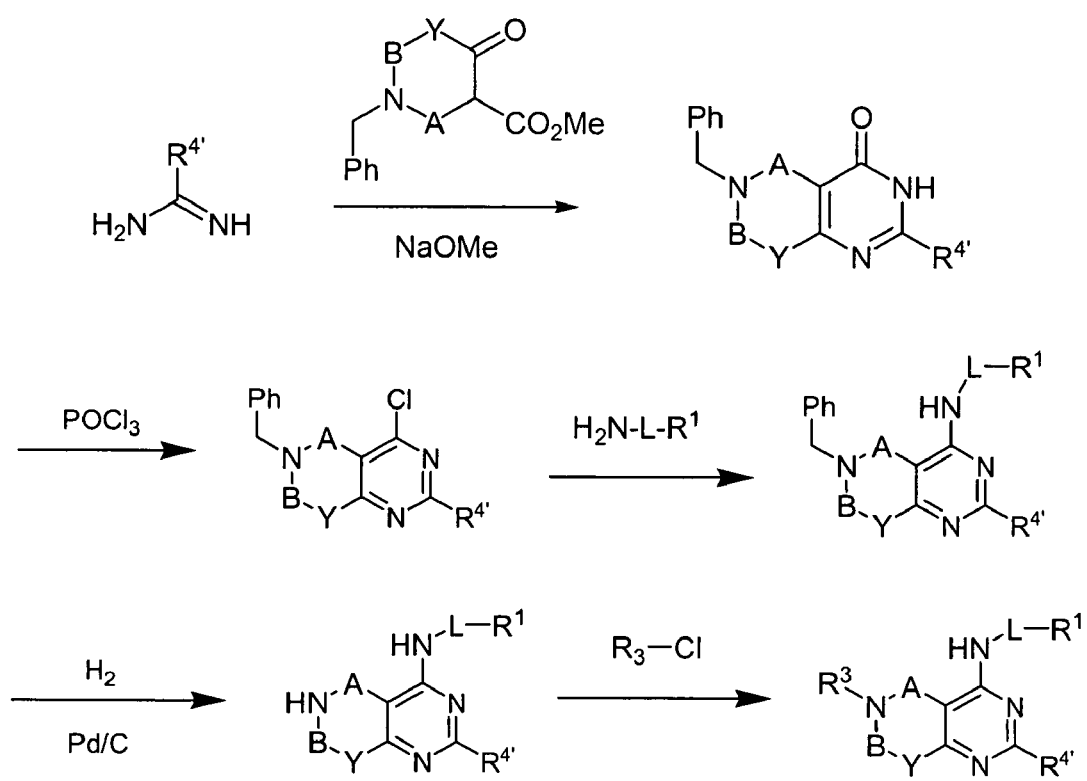
FIG. 1 provides a general synthetic scheme for preparing compounds provided herein.

When describing the compounds, pharmaceutical compositions containing such compounds and methods of using such compounds and compositions, the following terms have the following meanings unless otherwise indicated.

It should also be understood that, consistent with the scope of the present invention, any of the moieties defined herein and/or set forth below may be substituted with a variety of substituents, and that the respective definitions are intended to include such substituted moieties within their scope. By way of non-limiting example, such substituents may include, e.g., halo (such as fluoro, chloro, bromo), —CN, —CF$_3$, —OH, —OCF$_3$, $C_{2-6}$ alkenyl, $C_3$-$C_6$ alkynyl, $C_1$-$C_6$ alkoxy, aryl and di-$C_1$-$C_6$ alkylamino.

"Acyl" refers to a radical —C(O)R, where R is hydrogen, alkyl, cycloalkyl, cycloheteroalkyl, aryl, arylalkyl, heteroalkyl, heteroaryl, or heteroarylalkyl, as are defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, or heteroarylalkyl and R is hydrogen, alkyl, alkoxy, cycloalkyl, cycloheteroalkyl, aryl, arylalkyl, heteroalkyl, heteroaryl or heteroarylalkyl, as are defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-N'—, wherein R' is selected from hydrogen and alkyl.

"Arylamino" refers to the group aryl-NR'—, wherein R' is selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an unsubstituted amino group.

"Aminocarbonyl" or "amido" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carbocyclic" refers to a cyclic carbyl group, which includes an aromatic group, a non-aromatic group or a non-aromatic group fused with an aromatic group. Examples of representative carbocyclics include the following:

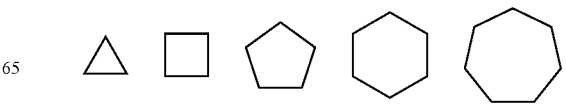

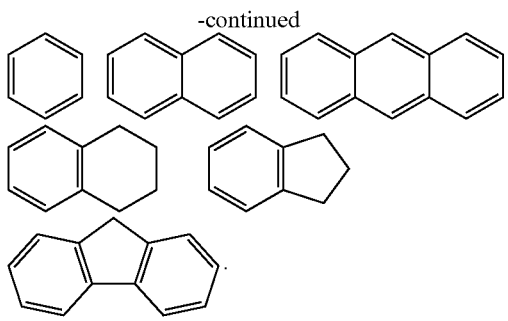

"Carboxyl" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy, and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group, as are defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, aryl, arylalkyl, cycloalkyl, cycloheteroalkyl, heteroalkyl, heteroaryl, heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl; and R$^{18}$ and R$^{19}$ are independently hydrogen, alkyl, aryl, arylalkyl, cycloalkyl, cycloheteroalkyl, heteroalkyl, heteroaryl or heteroarylalkyl.

Examples of representative substituted aryls include the following

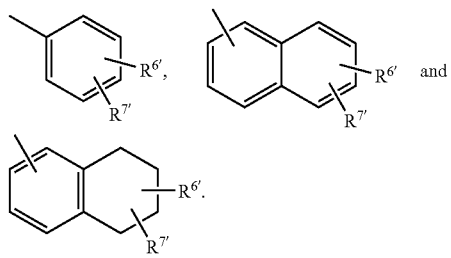

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{11}$, NR$^{10}$R$^{11}$, SO$_2$NR$^{10}$R$^{11}$, S-alkyl, S-alkyl, SO-alkyl, SO$_2$-alkyl, S-aryl, SO-aryl, SO$_2$-aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, heteroaryl, heteroalkyl, or the like.

"Hetero" when used to describe a compound or a group present on a compound or group means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroalkylene" refers to divalent saturated aliphatic hydrocarbyl groups particularly having up to about 11 carbon atoms and more particularly 1 to 6 carbon atoms which can be straight-chained or branched and one or more carbon atoms in the group have been replaced by a nitrogen, oxygen, or sulfur heteroatom. This term is exemplified by groups such as —(CH$_2$)$_2$SCH$_2$—, —(CH2)$_3$—SO$_2$CH$_2$—, —(CH$_2$)$_2$NHCH$_2$—, —(CH$_2$)$_4$OCH$_2$—, and the like.

"Substituted heteroalkylene" includes those groups recited in the definition of "substituted" herein, and particularly refers to a heteroalkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

Examples of representative heteroaryls include the following:

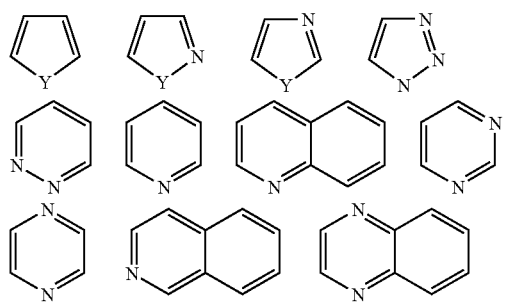

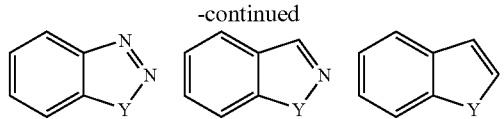

wherein each Y is selected from carbonyl, N, NR$^4$, O, and S, where R$^4$ is as defined herein.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl, morpholinyl, and include, for example, the following:

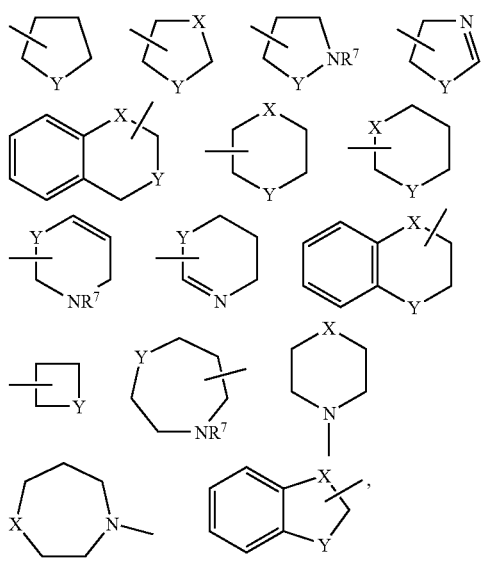

wherein each X is selected from C(R$^4$)$_2$, NR$^4$, O and S; each Y is selected from NR$^4$, O and S; where R$^4$ is as defined herein and R$^7$ is independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Optionally, a cycloheteroalkyl can be substituted, for example, with one or more groups selected from the group consisting of acyl, acylamino, acyloxy, alkoxy, alkoxycarbonyl, alkoxycarbonylamino, amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Representative cycloheteroalkenyls include the following:

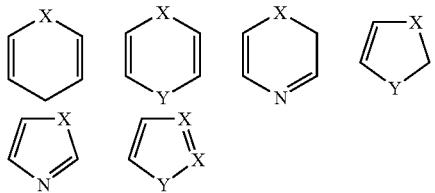

wherein each X is selected from C(R⁴)₂, NR⁴, O and S; and each Y is selected from carbonyl, N, NR⁴, O and S, where $R^4$ is as defined herein.

Representative aryls having heteroatoms containing substitution include the following:

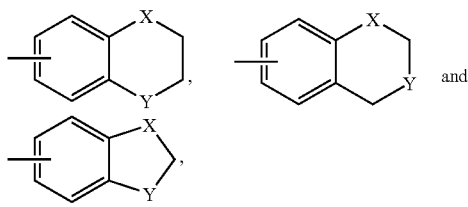

wherein each X is selected from C—R⁴, C(R⁴)₂, NR⁴, O and S; and each Y is selected from carbonyl, NR⁴, O and S, where $R^4$ is as defined herein.

"Hetero substituent" refers to a halo, O, S or N atom-containing functionality that may be present as an $R^4$ in a $CR^4$ group present as substituents directly on W or Z of the compounds of this invention or may be present as a substituent in the "substituted" aryl, heteroaryl and aliphatic groups present in the compounds. Examples of hetero substituents include: -halo, —NO₂, —NH₂, —NHR, —N(R)₂, —NRCOR, —NRSOR, —NRSO₂R, OH, CN, CO₂R, —CO₂H, —O—R, —CON(R)₂, —CONROR, —SO₃H, —S—R, —SO₂N(R)₂, —S(O)R, and —S(O)₂R, wherein each R is independently an aryl or aliphatic, optionally with substitution. Among hetero substituents containing R groups, preference is given to those materials having aryl and alkyl R groups as defined herein. Where feasible, each R may include hydrogen. Also, where feasible, two R groups when on same atom may join to form a heterocyclic ring of 3-8 atoms. For example, two R groups of $NR^2$, $SO_2NR^2$, and $CONR^2$ may join, together with the N atom, to form a N-morpholino, N-pyrrolo, N-piperidino, and N-pyrazolylo ring. Preferred hetero substituents are those listed above.

"Heterocyclic" refers to a cyclic group which includes a heteroaromatic group, a hetero non-aromatic or cycloheteroalkyl group, a non-aromatic group fused with a heteroaromatic group, a cycloheteroalkyl group fused with aromatic group and a cycloheteroalkyl group fused with a heteroaromatic group. Examples of representative heterocyclic groups include the following:

wherein each X is selected from C—R⁴, C(R⁴)₂, NR⁴, O and S; each Y is selected from carbonyl, NR⁴, O and S; and where $R^4$ and $R^7$ are as defined herein.

"Dihydroxyphosphoryl" refers to the radical —PO(OH)₂.

"Substituted dihydroxyphosphoryl" includes those groups recited in the definition of "substituted" herein, and particularly refers to a dihydroxyphosphoryl radical wherein one or both of the hydroxyl groups are substituted.

"Aminohydroxyphosphoryl" refers to the radical —PO(OH)NH₂.

"Substituted aminohydroxyphosphoryl" includes those groups recited in the definition of "substituted" herein, and particularly refers to an aminohydroxyphosphoryl wherein the amino group is substituted with one or two substituents and/or wherein the hydroxyl group is substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)₂— and aryl-S(O)₂—.

"Sulfanyl" refers to the radical HS—. "Substituted sulfanyl" refers to a radical such as RS— wherein R is any substituent described herein.

"Sulfonyl" refers to the divalent radical —S(O₂)—. "Substituted sulfonyl" refers to a radical such as S(O₂)—R wherein R is any substituent described herein. "Aminosulfonyl" or "Sulfonamide" refers to the radical H₂N(O₂)S—, and "substituted aminosulfonyl" "substituted sulfonamide" refers to a radical such as $R_2N(O_2)S$— wherein each R is independently any substituent described herein.

"Sulfoxide" refers to the divalent radical —S(O)—. "Substituted sulfoxide" refers to a radical such as S(O)—R, wherein R is any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol-keto structures and equilibrium are illustrated below:

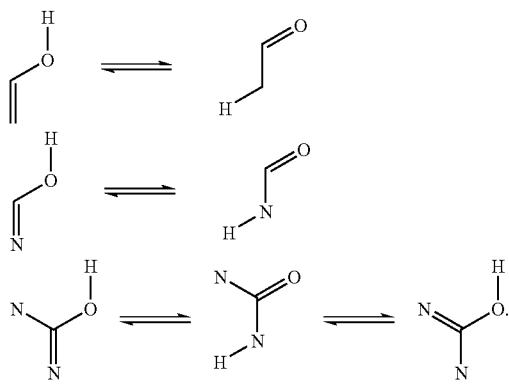

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

An "isotopic variant" refers to a compound as provided herein that contains unnatural proportions of isotopes at one or more of the atoms that constitute such compounds. For example, in certain embodiments, an "isotopic variant" of a compound can contain one or more radioactive isotopes such as tritium ($^3$H), iodine-125 ($^{125}$I), carbon-14 ($^{14}$C), and so forth. In some embodiments, an "isotopic variant" of a compound can be a stable form, that is, non-radioactive, for example containing one or more isotopes such as deuterium ($^2$H), carbon-13 ($^{13}$C), nitrogen-15 ($^{15}$N), and so forth. It will be understood that, in a compound as provided herein, any hydrogen can be $^2$H, for example, or any carbon can be $^{13}$C, as another example, or any nitrogen can be $^{15}$N, as another example, and so forth, where feasible according to the judgment of one of skill.

All isotopic variants of the compounds provided herein, radioactive or not, are intended to be encompassed with the scope of the invention.

The Compounds

In certain aspects, the present invention provides fused heterocyclic compounds useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In one aspect, the present invention provides fused heterocyclic compounds according to formula 1:

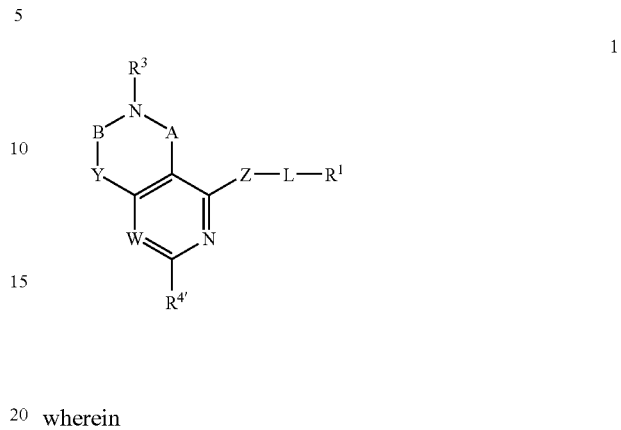

wherein

A and B are independently selected from $CR^{2'}R^{2'}$, CO, and CS;

Y is $CR^{2'}R^{2'}$;

W is selected from $CR^4$ and N;

Z is selected from O and $NR^2$;

L is a bond, substituted or unsubstituted alkylene, or substituted or unsubstituted heteroalkylene;

$R^1$ is a substituted a unsubstituted carbocyclic group or a substituted or unsubstituted heterocyclic group;

$R^2$ is selected from hydrogen, alkyl, cycloalkyl, aryl and aralkyl;

each $R^{2'}$ is selected from hydrogen, substituted or unsubstituted $C_1$-$C_6$ alkyl, substituted or unsubstituted $C_3$-$C_8$ cycloalkyl, substituted or unsubstituted aryl and substituted or unsubstituted aralkyl;

$R^3$ is a substituted or unsubstituted carbocyclic group or a substituted or unsubstituted heterocyclic group;

$R^4$ is selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and $R^{4'}$ is selected from $R^4$ and —Z'-L'-$R^4$, wherein Z' is a bond, $NR^{2'}$, O, S, SO, $SO_2$, COO, or $CONR^{2'}$ and L' is ($C_1$-$C_6$)alkylene;

or a pharmaceutically acceptable salt, solvate, prodrug, stereoisomer, tautomer or isotopic variant thereof.

In one aspect, a compound having formula 1a is provided:

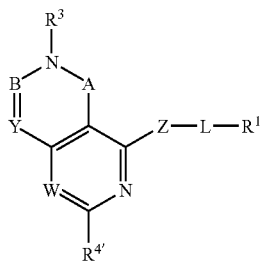

1a wherein
A is selected from $CR^{2'}R^{2'}$, CO, and CS;
each of B and Y is $CR^{2'}$;
W is selected from $CR^4$ and N;
Z is selected from O and $NR^2$;
L is a bond, substituted or unsubstituted alkylene, or substituted or unsubstituted heteroalkylene;
$R^1$ is a substituted a unsubstituted carbocyclic group or a substituted or unsubstituted heterocyclic group;
$R^2$ is selected from hydrogen, alkyl, cycloalkyl, aryl and aralkyl;
each of $R^{2'}$ is selected from hydrogen, substituted or unsubstituted $C_1$-$C_6$ alkyl, substituted or unsubstituted $C_3$-$C_8$ cycloalkyl, substituted or unsubstituted aryl and substituted or unsubstituted aralkyl;
$R^3$ is a substituted or unsubstituted carbocyclic group or a substituted or unsubstituted heterocyclic group;
$R^4$ is selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and
$R^{4'}$ is selected from $R^4$ and —Z'-L'-$R^4$, wherein Z' is a bond, $NR^{2'}$, O, S, SO, $SO_2$, COO, or $CONR^{2'}$ and L' is ($C_1$-$C_6$)alkylene;
or a pharmaceutically acceptable salt, solvate, prodrug, stereoisomer, tautomer or isotopic variant thereof.

With regard to compounds of formula 1, in certain embodiments, A, B and Y independently represent $CR^{2'}R^{2'}$. More suitably, with respect to formula 1, each of A, B and Y independently represent $CH_2$.

With respect to formula 1a, in certain embodiments, A represents $CH_2$ and each of B and Y independently represent CH.

With regard to compounds of formula 1 and 1a, in some embodiments, Z is O or NH. In one embodiment Z is O. In yet another and preferred embodiment Z is NH.

In some embodiments, L is a bond.
In certain embodiments, L is $C_1$-$C_9$ alkylene or $C_1$-$C_9$ heteroalkylene
In yet other embodiments, L is $C_2$-$C_5$ alkylene or $C_2$-$C_5$ heteroalkylene. In some embodiments, L is $C_2$-$C_5$ heteroalkylene containing two to four carbon atoms and a heteroatom selected from O, N, or S. Suitably the heteroatom is S.

In some embodiments, L is selected from —$CH_2$—, —$(CH_2)_2$—, —$(CH_2)_3$—, —$(CH_2)_4$—, —$CH(CH_3)CH_2$—, —$(CH_2)_2SCH_2$—, —$(CH_2)_2$—$SO_2CH_2$—, —$CH(CH_2CH_3)$ $CH_2OCH_2$—, —$CH_2CHF$—, —$CH_2CF_2$—, —$CH_2CH$(OH)— and —$CH_2CO$—.

In a preferred embodiment, L is a bond, or is a —$(CH_2)_2$ $SCH_2$— group.

With regard to formula 1, in certain embodiments, the compound is selected from the group consisting of 6-(3-chloropyridin-2-yl)-N-(4-(difluoromethoxy)phenyl)-5,6,7,8-tetrahydropyrido[4,3-d]pyrimidin-4-amine; 6-(3-chloropyridin-2-yl)-5,6,7,8-tetrahydro-N-phenylpyrido[4,3-d]pyrimidin-4-amine; 6-(3-chloropyridin-2-yl)-N-(4-fluorophenyl)-5,6,7,8-tetrahydropyrido[4,3-d]pyrimidin-4-amine; 6-(3-chloropyridin-2-yl)-N-(6-(trifluoromethyl)pyridin-3-yl)-5,6,7,8-tetrahydropyrido[4,3-d]pyrimidin-4-amine; N-(6-(trifluoromethyl)pyridin-3-yl)-5,6,7,8-tetrahydro-6-(3-(methylsulfonyl)pyridin-2-yl)pyrido[4,3-d]pyrimidin-4-amine; 6-(3-chloropyridin-2-yl)-5,6,7,8-tetrahydro-N-(4-(trifluoromethylsulfonyl)phenyl)pyrido[4,3-d]pyrimidin-4-amine; 5,6,7,8-tetrahydro-6-(3-(methylsulfonyl)pyridin-2-yl)-N-(4-(trifluoromethylsulfonyl)phenyl)pyrido[4,3-d]pyrimidin-4-amine; 5,6,7,8-tetrahydro-N-(2,3-dihydrobenzo[b][1,4]dioxin-6-yl)-6-m-tolylpyrido[4,3-d]pyrimidin-4-amine; N-(4-(trifluoromethyl)phenyl)-5,6,7,8-tetrahydro-6-phenylpyrido[4,3-d]pyrimidin-4-amine; N-(4-(trifluoromethyl)phenyl)-5,6,7,8-tetrahydro-6-o-tolylpyrido[4,3-d]pyrimidin-4-amine; N-(4-(trifluoromethyl)phenyl)-5,6,7,8-tetrahydro-6-m-tolylpyrido[4,3-d]pyrimidin-4-amine; and N-(4-(trifluoromethyl)phenyl)-5,6,7,8-tetrahydro-6-p-tolylpyrido[4,3-d]pyrimidin-4-amine.

With regard to formula 1, in certain embodiments where L is a bond, the compound is not 6-(3-chloropyridin-2-yl)-N-(4-(difluoromethoxy)phenyl)-5,6,7,8-tetrahydropyrido[4,3-d]pyrimidin-4-amine; 6-(3-chloropyridin-2-yl)-5,6,7,8-tetrahydro-N-phenylpyrido[4,3-d]pyrimidin-4-amine; 6-(3-chloropyridin-2-yl)-N-(4-fluorophenyl)-5,6,7,8-tetrahydropyrido[4,3-d]pyrimidin-4-amine; 6-(3-chloropyridin-2-yl)-N-(6-(trifluoromethyl)pyridin-3-yl)-5,6,7,8-tetrahydropyrido[4,3-d]pyrimidin-4-amine; N-(6-(trifluoromethyl)pyridin-3-yl)-5,6,7,8-tetrahydro-6-(3-(methylsulfonyl)pyridin-2-yl)pyrido[4,3-d]pyrimidin-4-amine; 6-(3-chloropyridin-2-yl)-5,6,7,8-tetrahydro-N-(4-(trifluoromethylsulfonyl)phenyl)pyrido[4,3-d]pyrimidin-4-amine; 5,6,7,8-tetrahydro-6-(3-(methylsulfonyl)pyridin-2-yl)-N-(4-(trifluoromethylsulfonyl)phenyl)pyrido[4,3-d]pyrimidin-4-amine; 5,6,7,8-tetrahydro-N-(2,3-dihydrobenzo[b][1,4]dioxin-6-yl)-6-m-tolylpyrido[4,3-d]pyrimidin-4-amine; N-(4-(trifluoromethyl)phenyl)-5,6,7,8-tetrahydro-6-phenylpyrido[4,3-d]pyrimidin-4-amine; N-(4-(trifluoromethyl)phenyl)-5,6,7,8-tetrahydro-6-o-tolylpyrido[4,3-d]pyrimidin-4-amine; N-(4-(trifluoromethyl)phenyl)-5,6,7,8-tetrahydro-6-m-tolylpyrido[4,3-d]pyrimidin-4-amine; or N-(4-(trifluoromethyl)phenyl)-5,6,7,8-tetrahydro-6-p-tolylpyrido[4,3-d]pyrimidin-4-amine.

With regard to formula 1, in certain embodiments where L is a bond, the compound is not:
3-chloro-7-cyclohexyl-1-(cyclohexylamino)-5,6,7,8-tetrahydro-2,7-naphthyridine-4-carbonitrile;
7-cyclohexyl-1-(cyclohexylamino)-5,6,7,8-tetrahydro-3-(1-piperidinyl)-2,7-naphthyridine-4-carbonitrile; or
7-cyclohexyl-1-(cyclohexylamino)-5,6,7,8-tetrahydro-3-(4-morpholinyl)-2,7-naphthyridine-4-carbonitrile.

With regard to compounds of formula 1 and 1a, in certain embodiments, W is $CR^4$. In some embodiments, W is N.

In certain embodiments, $R^1$ is a carbocyclic group. Alternatively, $R^1$ is a heterocyclic group.

In some embodiments, $R^1$ is an aryl or heteroaryl group.

In certain other embodiments, $R^1$ is a cycloalkyl or cycloheteroalkyl group.

In yet other embodiments, $R^1$ is selected from substituted or unsubstituted

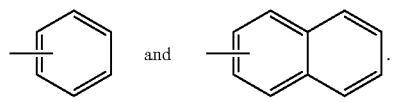

In yet other embodiments, $R^1$ is selected from substituted or unsubstituted

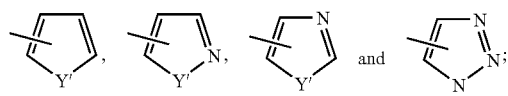

wherein Y' is selected from O, N, S, SO, $SO_2$, and $NR^{2'}$.

In some embodiments, $R^1$ is selected from substituted or unsubstituted

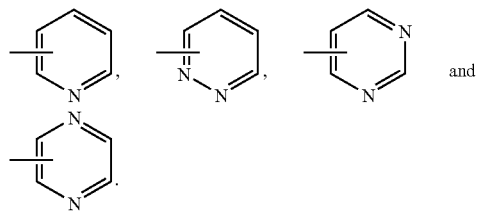

In certain embodiments, $R^1$ is selected from substituted or unsubstituted

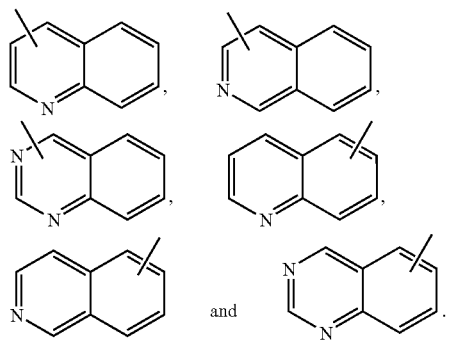

In other embodiments, $R^1$ is selected from substituted or unsubstituted

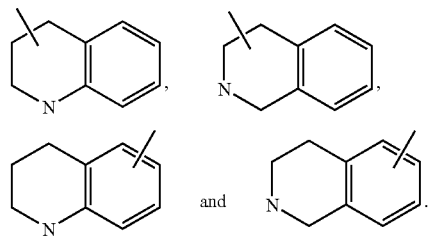

In yet other embodiments, $R^1$ is selected from substituted or unsubstituted

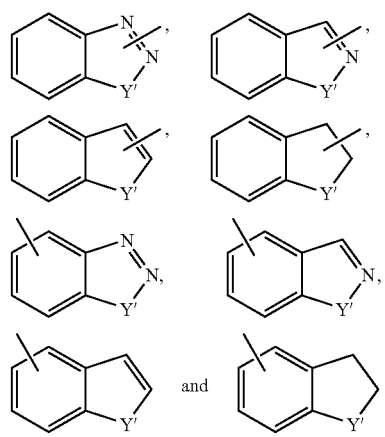

wherein Y' is selected from $CR^{2'}$, $CR^{2'}R^{2'}$, N, O, S, SO, $SO_2$ and $NR^{2'}$.

In some embodiments, $R^1$ is selected from substituted or unsubstituted

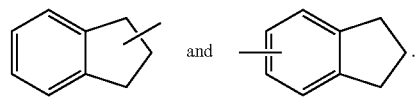

In some embodiments, $R^1$ is selected from substituted or unsubstituted

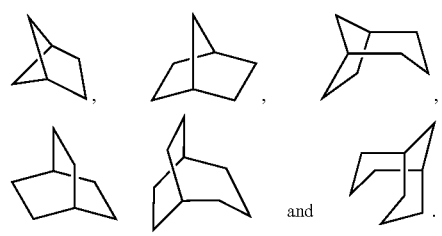

In preferred embodiments, $R^1$ is selected from
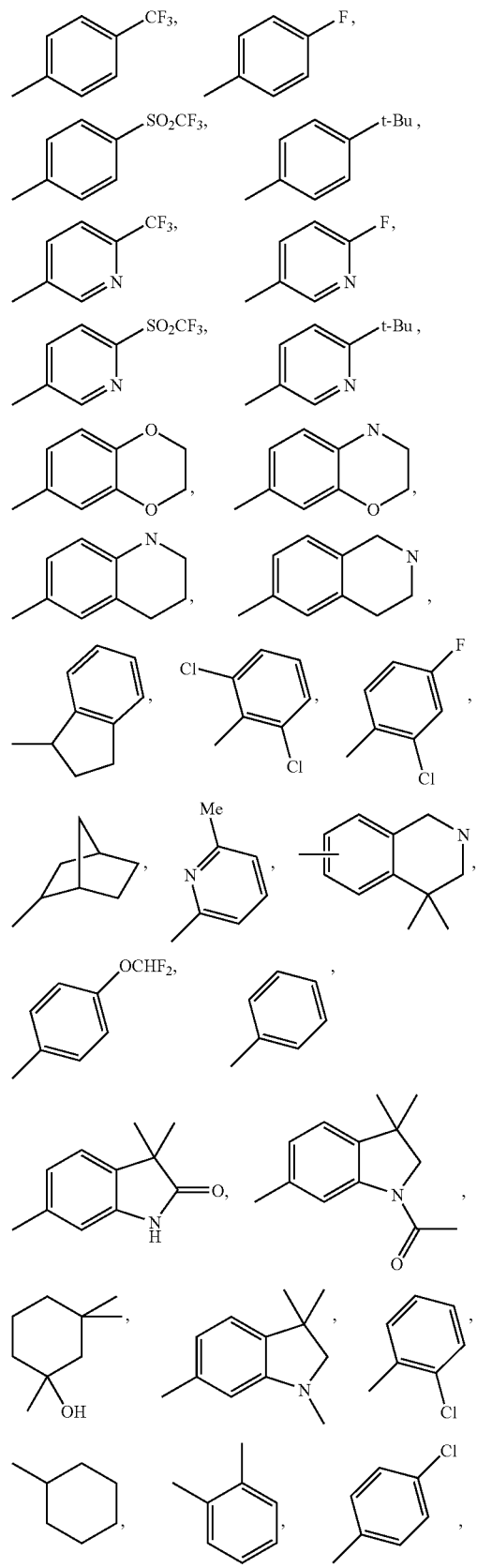
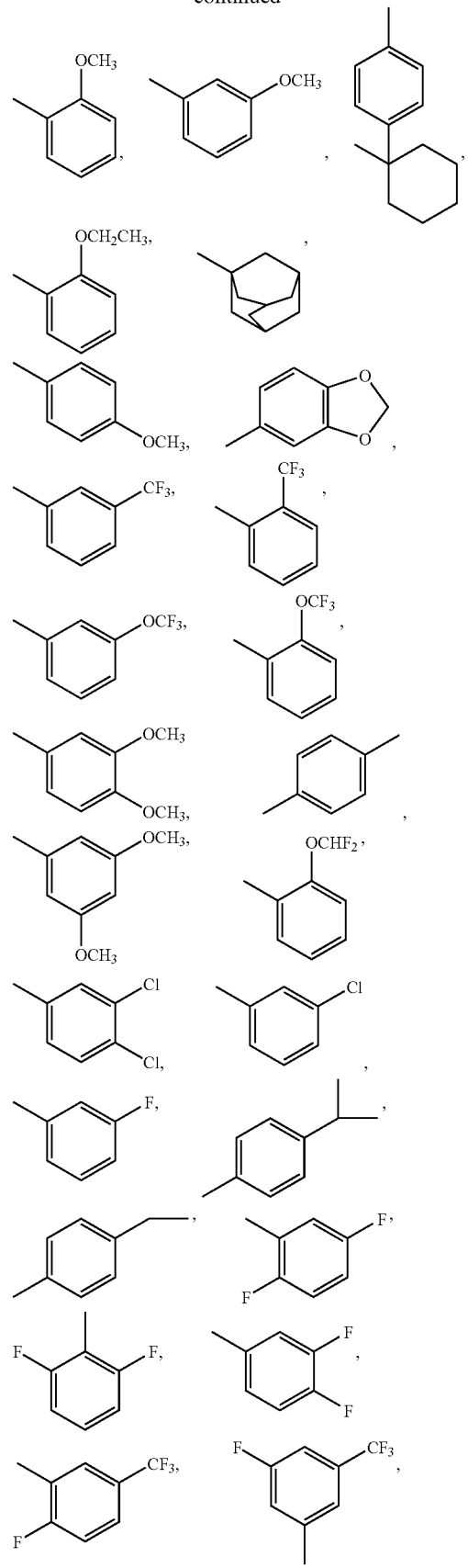

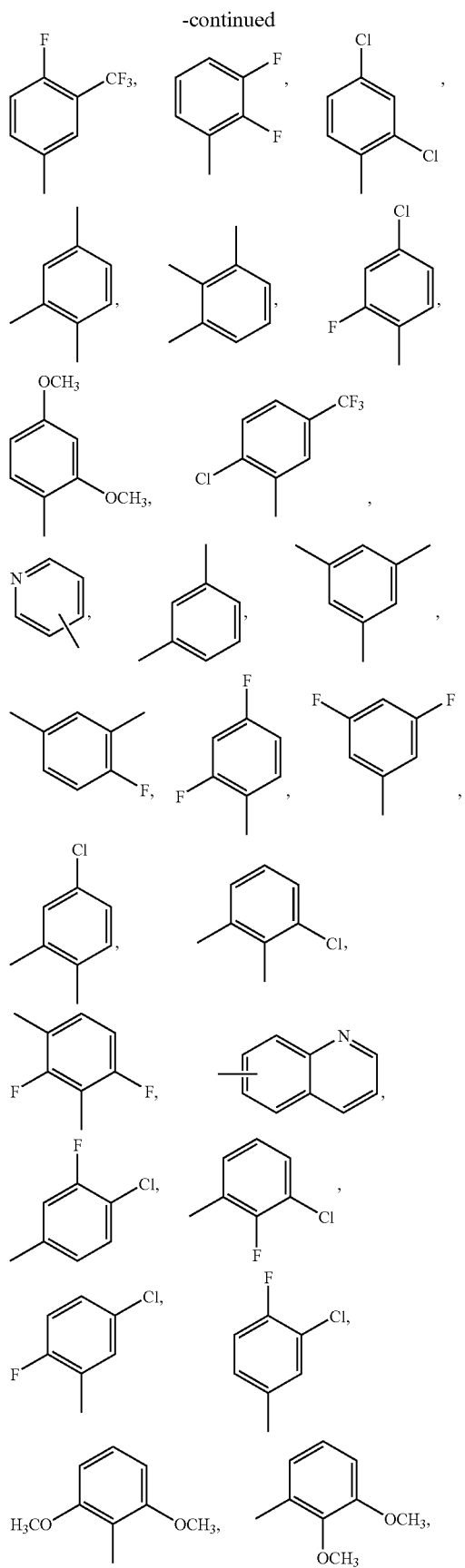
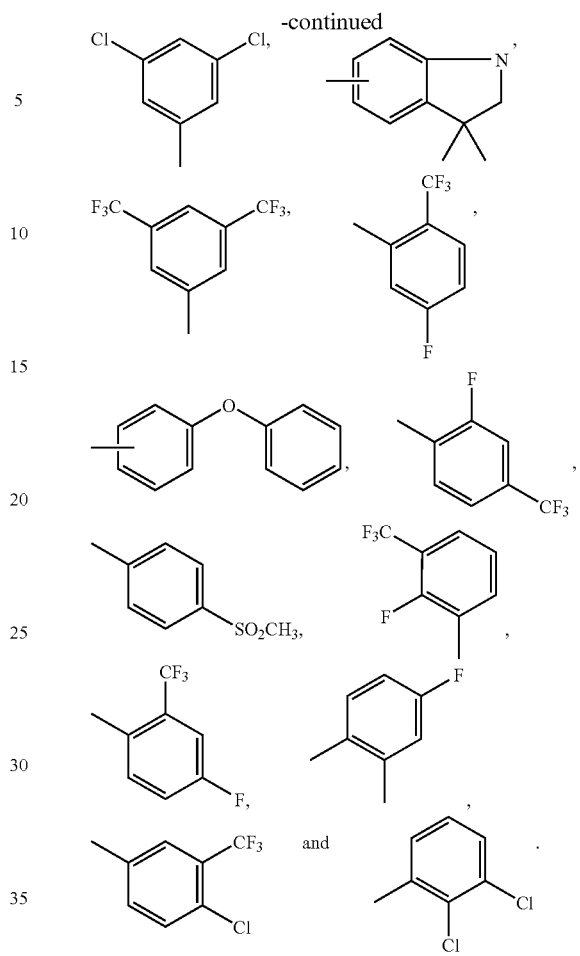

Suitably, the substituent on N is H or substituted or unsubstituted alkyl, where feasible.

With regard to formula 1 and 1a, in certain embodiments, $R^2$ is selected from hydrogen, $C_1$-$C_6$ alkyl, $C_3$-$C_8$ cycloalkyl, aryl and aralkyl. In certain embodiments, $R^2$ is selected from hydrogen, $C_1$-$C_6$ alkyl, and $C_3$-$C_8$ cycloalkyl.

With regard to formula 1 and 1a, in certain embodiments, each $R^{2'}$ is independently selected from hydrogen, and substituted or unsubstituted $C_1$-$C_6$ alkyl. In preferred embodiments, $R^{2'}$ is hydrogen.

In certain embodiments, $R^3$ is a carbocyclic group. In some embodiments, $R^3$ is a heterocyclic group. In certain embodiments, $R^3$ is an aryl or heteroaryl. In some embodiments, $R^3$ is an aryl.

In some embodiments, $R^3$ is selected from substituted or unsubstituted aryl, substituted or unsubstituted heteroaryl, substituted or unsubstituted cycloalkyl, substituted or unsubstituted cycloheteroalkyl, substituted or unsubstituted cycloalkenyl, substituted or unsubstituted cycloheteroalkenyl, substituted or unsubstituted bicycloalkyl, substituted or unsubstituted bicycloheteroalkyl, substituted or unsubstituted bicycloalkenyl, substituted or unsubstituted bicycloheteroalkenyl, substituted or unsubstituted bicycloaryl, and substituted or unsubstituted bicycloheteroaryl.

In some embodiments, $R^3$ is a phenyl. In certain embodiments, $R^3$ is a substituted phenyl.

In some embodiments, $R^3$ is a mono-substitued phenyl.

In other embodiments, $R^3$ is a di-substituted phenyl.

In certain embodiments, $R^3$ is a substituted phenyl where the substituent on the phenyl is selected from halo, amido, alkyl, alkoxy, sulfonyl, sulfonamidyl, haloalkyl and trihaloalkyl. In preferred embodiments, the substitution on the $R^3$ phenyl is selected from Cl, F, $CF_3$, Me, OMe, $SO_2R^{2'}$, $NR^{2'}R^{2'}$, and $SO_2NR^{2'}R^{2'}$. In more preferred embodiments, the substitution on the $R^3$ phenyl is selected from Cl, Me and $SO_2Me$. In the most preferred embodiments, the substitution on the $R^3$ phenyl is Cl.

In embodiments where $R^3$ is a substituted phenyl, one or more substitutuents are on the phenyl at the 2 (ortho), 3 (meta) and/or 4 (para) position relative to the carbon attached to the nitrogen atom in the fused heterocyclic scaffold in formula 1 or 1a. In certain embodiments, $R^3$ is a substituted phenyl, where a substituent is on the phenyl at the 2 (ortho), 3 (meta) and/or 4 (para) position. In more preferred embodiments, the substitution on the $R^3$ phenyl is at the 2 or 4 position. In the most preferred embodiments, the substitution on the $R^3$ phenyl is at the 2 position.

In some embodiments, $R^3$ is a heteroaryl.

In certain embodiments, $R^3$ is a substituted pyridyl or pyrimidine group.

In some embodiments, $R^3$ is a substituted pyridyl.

In some embodiments, $R^3$ is a substituted pyrid-2-yl. In certain embodiments, the $R^3$ pyrid-2-yl is di-substituted. In preferred embodiments, the $R^3$ pyrid-2-yl is mono substituted.

In other embodiments, the substituent on the $R^3$ pyrid-2-yl is selected from halo, amido, alkyl, alkoxy, sulfonyl, sulfonamidyl, haloalkyl and trihaloalkyl.

In preferred embodiments, the substitution on the $R^3$ pyrid-2-yl is selected from Cl, F, $CF_3$, Me, OMe, $SO_2R^{2'}$, $NR^{2'}R^{2'}$, and $SO_2NR^{2'}R^{2'}$. In more preferred embodiments, the substitution on $R^3$ pyrid-2-yl is selected from Cl, Me and $SO_2Me$. In the most preferred embodiments, the substitution on $R^3$ pyrid-2-yl is Cl or Me.

In some embodiments, the substitution on the $R^3$ pyrid-2-yl is at the 3, 4 or 5 position. In more preferred embodiments, the substitution on the $R^3$ pyrid-2-yl is at the 3 or 5 position. In the most preferred embodiments, the substitution on the $R^3$ pyrid-2-yl is at the 3-position.

In the most preferred embodiments, $R^3$ is 3-chloropyrid-2-yl or 5-methylpyrid-2-yl.

In some embodiments, $R^1$ or $R^3$ are selected from

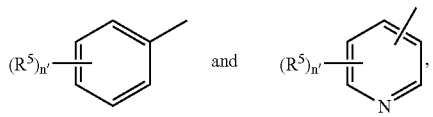

wherein subscript n' is selected from 1-5 and each of $R^5$ is independently selected from hydrogen, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

With regard to formula 1 and 1a, in certain embodiments, W is $CR^4$, where $R^4$ is as defined above in formula 1.

In some embodiments, W is $CR^4$, where $R^4$ is selected from H, alkyl and halo.

In preferred embodiments, W is $CR^4$, and $R^4$ is H.

In certain embodiments $R^{4'}$ is selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio.

In some embodiments, $R^{4'}$ is selected from H, halo, alkyl, $CF_3$, cyano, $OR^{2'}$, $SR^{2'}$, $COOR^{2'}$, and $CONR^{2'}R^{2'}$.

In yet other embodiments, $R^{4'}$ is selected from Et, Cl, Me, n-Bu, i-Pr, n-Pr, $CH_2F$, NHEt, OEt, $CO_2H$, $SO_2Me$, $CONHCH_2Ph$, SMe, SEt, S-n-Pr, $SCH_2Ph$, S-i-Pr, $SCH_2COMe$, $SCH_2COOMe$, $SCH_2CONHMe$, $SCH_2CF_3$, $SCH_2CN$, $SCH_2CONH_2$, $S(CH_2)_2OH$, $S(CH_2)_2OMe$, $S(CH_2)_2COOMe$, $S(CH_2)_2NHCOMe$, $SCH_2CH(OH)CH_2OH$, $SCH_2CH(OH)CH_3$, $S(CH_2)_2F$, $S(CH_2)_3OH$, and $SCH_2C(Me)_2OH$. In one preferred embodiment, $R^{4'}$ is $S(CH_2)_2OH$.

In yet other embodiments, $R^{4'}$ is selected from OMe, OEt, O-n-Pr, $OCH_2Ph$, O-i-Pr, $OCH_2COMe$, $OCH_2COOMe$, $OCH_2CONHMe$, $OCH_2CF_3$, $OCH_2CN$, $OCH_2CONH_2$, $O(CH_2)_2OH$, $O(CH_2)_2OMe$, $O(CH_2)_2COOMe$, $O(CH_2)_2NHCOMe$, $OCH_2CH(OH)CH_2OH$, $OCH_2CH(OH)CH_3$, $O(CH_2)_2F$, $O(CH_2)_3OH$, and $OCH_2C(Me)_2OH$. In one preferred embodiment, $R^{4'}$ is $O(CH_2)_2OH$.

In yet other embodiments, $R^{4'}$ is selected from $CH_2Me$, $CH_2Et$, $CH_2$-n-Pr, $CH_2CH_2Ph$, $CH_2$-i-Pr, $CH_2CH_2COMe$, $CH_2CH_2COOMe$, $CH_2CH_2CONHMe$, $CH_2CH_2CF_3$, $CH_2CH_2CN$, $CH_2CH_2CONH_2$, $CH_2(CH_2)_2OH$, $CH_2(CH_2)_2OMe$, $CH_2(CH_2)_2COOMe$, $CH_2(CH_2)_2NHCOMe$, $CH_2CH_2CH(OH)CH_2OH$, $CH_2CH_2CH(OH)CH_3$, $CH_2(CH_2)_2F$, $CH_2(CH_2)_3OH$, and $CH_2CH_2C(Me)_2OH$. In one preferred embodiment, $R^{4'}$ is $CH_2(CH_2)_2OH$.

In other embodiments, $R^{4'}$ is a group —Z'-L'-$R^4$.

In certain embodiments, when $R^{4'}$ is a group —Z'-L'-$R^4$, Z' is selected from a bond, $NR^{2'}$, O, S, SO, $SO_2$, and CONH. In further embodiments, Z' is a bond, O or S. In yet further embodiments, Z' is O or S. In a preferred embodiment, Z' is S.

In certain embodiments when $R^{4'}$ is a group —Z'-L'-$R^4$, L' is a substituted or unsubstituted alkylene chain or heteroalkylene chain. In further embodiments, L' is a substituted or unsubstituted alkylene chain of 1-9 C atoms in length. In preferred embodiments, L' is selected from —$(CH_2)_2$—, —$(CH_2)_3$—, —$(CH_2)_4$—, —$CH(CH_3)CH_2$—, —$CH(CH_2CH_3)CH_2OCH_2$—, —$CH_2CHF$—, —$CH_2CF_2$—, and —$CH_2CH(OH)$—. In more preferred embodiments, L' is selected from —$(CH_2)_2$—, —$CH(CH_3)CH_2$—, —$CH_2CHF$—, —$CH_2CF_2$—, and —$CH_2CH(OH)$—. In one preferred embodiment, L' is —$(CH_2)_2$—.

In certain embodiments when $R^{4'}$ is a group —Z'-L'-$R^4$, $R^4$ is selected from H, halo, alkoxy, $CF_3$, $COOR^{2'}$, $COR^{2'}$, $CONR^{2'}R^{2'}$, OH, CN and substituted or unsubstituted aryl. In further embodiments, $R^4$ is selected from halo, OH, $CF_3$, COMe and COOMe. In preferred embodiments, $R^4$ is selected from halo, OH, $CF_3$, and COMe. In more preferred embodiments, $R^4$ is selected from halo and OH. In one preferred embodiment, $R^4$ is OH.

A, B and Y can, for example, all represent $CH_2$. Alternatively, A can represent CO, and B and Y represent $CH_2$. Alternatively, B can represent CO, and A and Y represent $CH_2$.

Among the compounds described above by formula 1, in certain preferable embodiments, $R^3$ is a 6 membered aryl or heteroaryl ring.

With regard to formula 1, in certain embodiments, a compound is provided having formula 2:

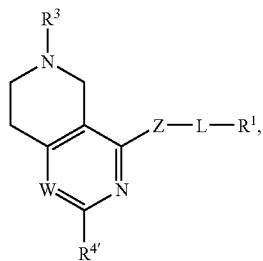

wherein W, Z, L, $R^1$, $R^3$ and $R^{4'}$ are as defined above in formula 1, or a pharmaceutically acceptable salt, solvate, prodrug, stereoisomer, tautomer or isotopic variant thereof.

With regard to formula 2, in some embodiments, W is selected from $CR^4$ and N.

In some embodiments, Z is NH.

In some embodiements, $R^3$ is selected from substituted or unsubstituted aryl, substituted or unsubstituted heteroaryl, substituted or unsubstituted cycloalkyl, substituted or unsubstituted cycloheteroalkyl, cycloalkenyl, substituted or unsubstituted cycloheteroalkenyl, substituted or unsubstituted bicycloalkyl, substituted or unsubstituted bicycloheteroalkyl, substituted or unsubstituted bicycloalkenyl, substituted or unsubstituted bicycloheteroalkenyl, substituted or unsubstituted bicycloaryl, and substituted or unsubstituted bicycloheteroaryl.

In some embodiments, $R^{4'}$ is H.

In some embodiments, the compound according to formula 1 can be described by formula 3:

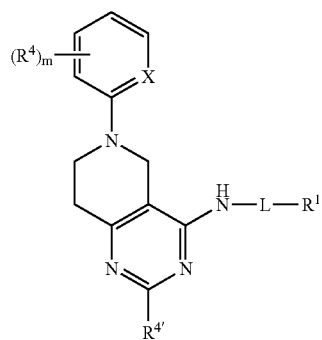

wherein
X is N or $CR^4$;
L is a bond, substituted or unsubstituted alkylene, or substituted or unsubstituted heteroalkylene;
$R^1$ is a substituted a unsubstituted carbocyclic group or a substituted or unsubstituted heterocyclic group;

each $R^4$ is independently selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

$R^{4'}$ is selected from $R^4$ and a group —Z'-L'-$R^4$, wherein Z' is a bond, $NR^{2'}$, O, S, SO, $SO_2$, COO, or $CONR^{2'}$; and L' is substituted or unsubstituted $C_1$-$C_6$ alkylene; and
subscript m is selected from 0-4.

In certain embodiments, subscript m is selected from 0 to 3.

In some embodiments, the compounds according to formula 1a can be described by formula 4:

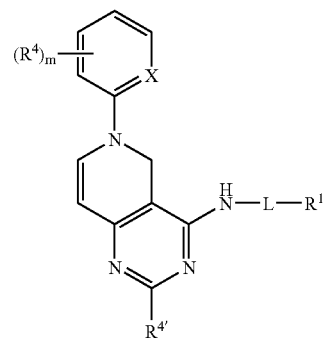

wherein
X is N or $CR^4$;
L is a bond or substituted or unsubstituted alkylene or heteroalkylene chain;
$R^1$ is substituted and unsubstituted carbocyclic or heterocyclic group;
each $R^4$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

$R^{4'}$ is selected from $R^4$ and a group —Z'-L'-$R^{4''}$, wherein Z' is a bond, $NR^{2'}$, O, S, SO, $SO_2$, COO, or $CONR^{2'}$; L' is substituted or unsubstituted $C_1$-$C_6$ alkylene chain and $R^{4''}$ is $R^4$; and subscript m is selected from 0-4;

or a pharmaceutically acceptable salt, solvate, prodrug, stereoisomer, tautomer, or isotopic variant thereof.

In some embodiments, subscript m is selected from 0, 1, 2 or 3.

It will be understood that the compounds provided herein, for example, as provided in any formula, including formulas 1-10, can be in the form of a pharmaceutically acceptable salt, solvate, prodrug, stereoisomer, tautomer, or istopic variant.

In certain embodiments, compounds are provided having any one of formulas 5-10:

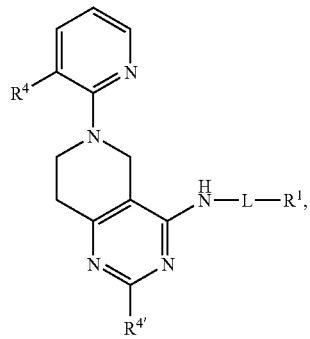

5

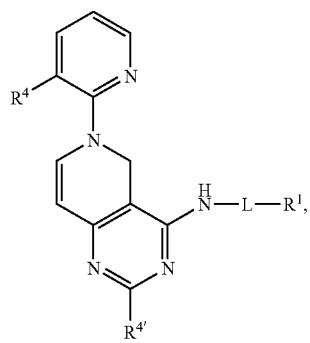

6

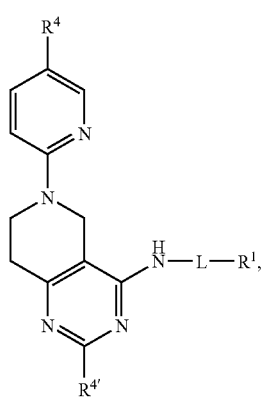

7

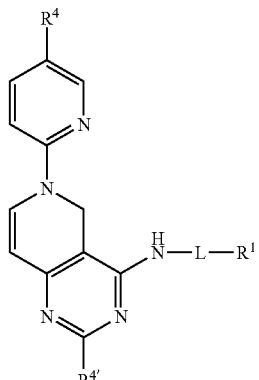

8

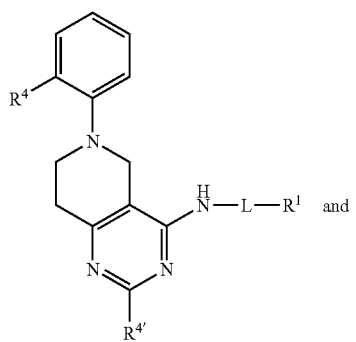

9

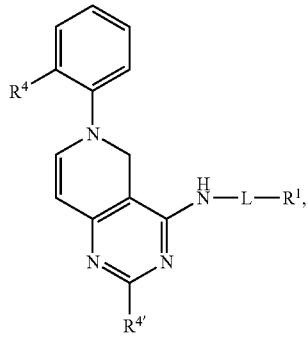

and

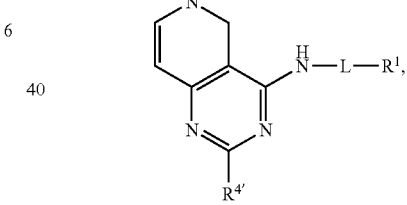

10 wherein $R^4$ is selected from Cl, F, Me, iso-Pr, OMe, $OCF_3$, $SO_2CF_3$, $SO_2Me$, and $SO_2NMe_2$, and L, $R^1$ and $R^{4'}$ are as defined above.

In some embodiments, L-$R^1$ can, for example, be selected from

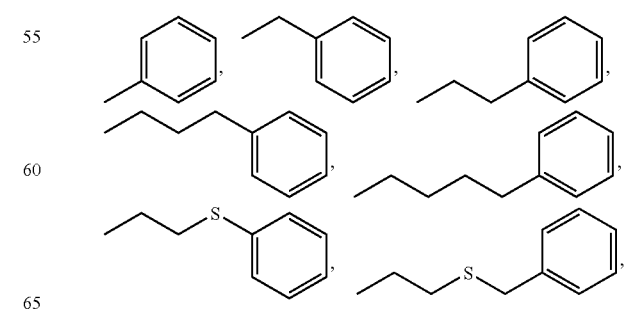

and substitued versions thereof, where the phenyl is substituted with 1, 2 or 3 halo, $CF_3$, or SMe groups.

In certain embodiments, L-$R^1$ is selected from substituted or unsubstituted

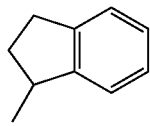 and 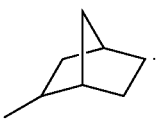.

In some embodiements, L-$R^1$ is selected from substituted or unsubstituted

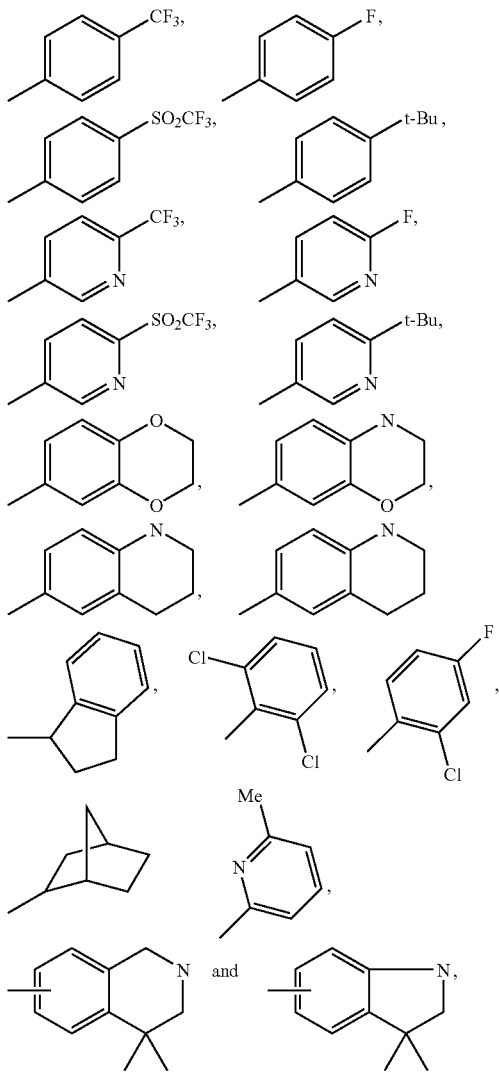

wherein the substitutent on N is H or substituted or unsubstituted alkyl.

In certain embodiments, L-$R^1$ is selected from substituted or unsubstituted

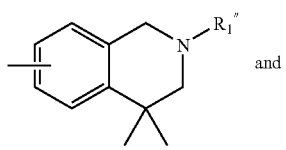 and

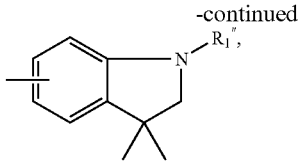, wherein
$R^{1''}$ is H, alkyl, or a group represented by —$(CR^{2'}R^{2'})_n$—$R^{3''}$;
each $R^{2'}$ is selected from hydrogen, substituted or unsubstituted $C_1$-$C_6$ alkyl, substituted or unsubstituted $C_3$-$C_8$ cycloalkyl, substituted or unsubstituted aryl and substituted or unsubstituted aralkyl;
$R^{3''}$ is hydrogen, a hetero substituent, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, or bicycloheteroaryl ring; and
subscript n is selected from 2-5.

In preferred embodiments, each $R^{2'}$ is H; subscript n is 2-4 and $R^{3''}$ is substituted or unsubstituted cycloalkyl, cycloheteroalkyl, aryl or heteroaryl.

$R^{3''}$ can, for example, be substituted or unsubstituted

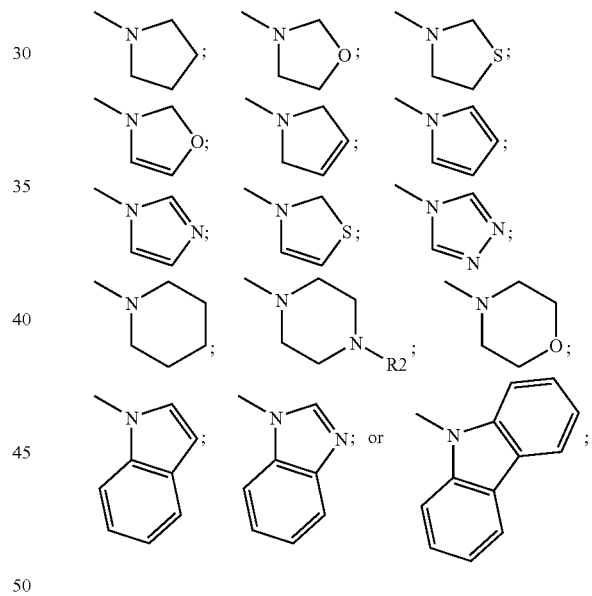

and where $R^2$ is H or alkyl.

$R^{3''}$ can, for example, be a hetero substitutent and there is a preference for the heterosubstituent to be COOH, $SO_2Me$, SMe, OH, OEt, OMe, $NEt_2$, halo, $NHSO_2Me$, $CONH_2$, $CONMe_2$, $SO_2NH_2$, and $SO_2NMe_2$.

Additional embodiments within the scope of the present invention are set forth in non-limiting fashion elsewhere herein and in the examples. It should be understood that these examples are for illustrative purposes only and are not to be construed as limiting this invention in any manner.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Certain compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy) alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the fused heterocyclic compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The compound of formula I is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present fused heterocyclic compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, asthma, myocardial infarction, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example psoriasis; obesity; lipid disorders; cancer; and renal disorders method comprises administering an effective condition-treating or condition-preventing amount of one or more of the pharmaceutical compositions just described.

As a further aspect of the invention there is provided the present fused heterocyclic compounds for use as a pharmaceutical especially in the treatment or prevention of the aforementioned conditions and diseases. We also provide the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active amines and derivatives.

General Synthetic Procedures

The fused heterocyclic compounds of this invention can be prepared from readily available starting materials using the following general methods and procedures. See, e.g., FIG. 1 and Synthetic Schemes 1-10 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, N.Y., 1991, and references cited therein.

The compounds of this invention, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative fused heterocyclics that have been listed hereinabove. The compounds of the invention may be prepared from known or commercially available starting materials and reagents by one skilled in the art of organic synthesis.

Synthetic Scheme 1

Various N-substituted-6-(pyridin-2-yl)-5,6,7,8-tetrahydropyrido[4,3-d]pyrimidin-4-amine derivatives are prepared using a general procedure described below. Accordingly, ethyl 1-benzyl-4-oxopiperidine-3-carboxylate hydrochloride is reacted with formamidine acetate to yield 6-benzyl-5,6,7,8-tetrahydropyrido[4,3-d]pyrimidin-4(4aH)-one, which, in turn, is reacted with POCl₃ to afford the 4-chloro derivative. The intermediate chloro derivative is then condensed with substituted aniline or amine to give the desired N-substituted-6-benzyl-5,6,7,8-tetrahydropyrido[4,3-d]pyrimidin-4-amine. Debenzylation using standard procedures known in the art followed by nucleophilic displacement of an appropriate 2-halo-pyridine yields the appropriate N-substituted-6-(pyridin-2-yl)-5,6,7,8-tetrahydropyrido[4,3-d]pyrimidin-4-amine. As a representative example, synthesis of N-(4-tert-butylphenyl)-6-(3-chloropyridin-2-yl)-5,6,7,8-tetrahydropyrido[4,3-d]pyrimidin-4-amine is depicted in Scheme 1.

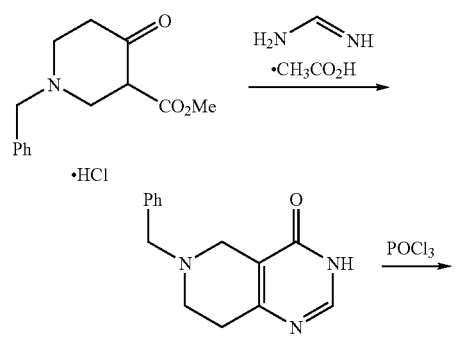

-continued

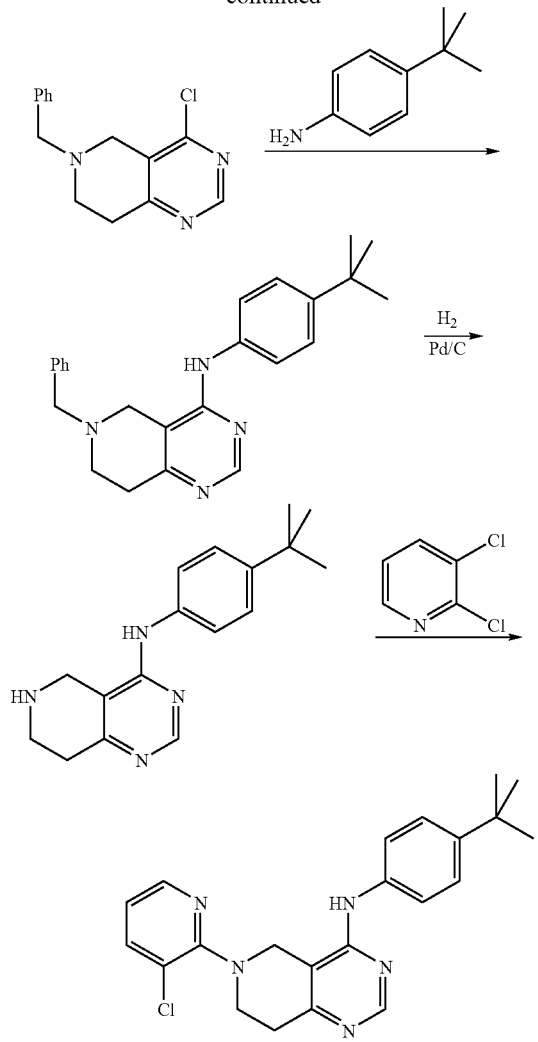

Synthetic Scheme 2

Conversely, N-substituted-6-(pyridin-2-yl)-5,6,7,8-tetrahydropyrido[4,3-d]pyrimidin-4-amine derivatives are prepared by first deprotecting the 6-benzyl-5,6,7,8-tetrahydropyrido[4,3-d]pyrimidin-4(4aH)-one and reacting the product with an appropriate 2-halo-pyridine to give the 6-(pyridin-2-yl)-5,6,7,8-tetrahydropyrido[4,3-d]pyrimidin-4(4aH)-one which is reacted with POCl₃ followed by condensation with an appropriate aniline or amine to yield the appropriate the appropriate N-substituted-6-(pyridin-2-yl)-5,6,7,8-tetrahydropyrido[4,3-d]pyrimidin-4-amine. As a representative example, synthesis of N-(4-tert-butylphenyl)-6-(3-chloropyridin-2-yl)-5,6,7,8-tetrahydropyrido[4,3-d]pyrimidin-4-amine is depicted in Scheme 2.

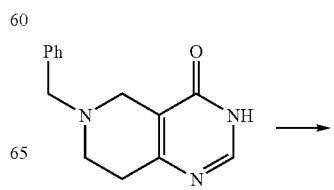

-continued

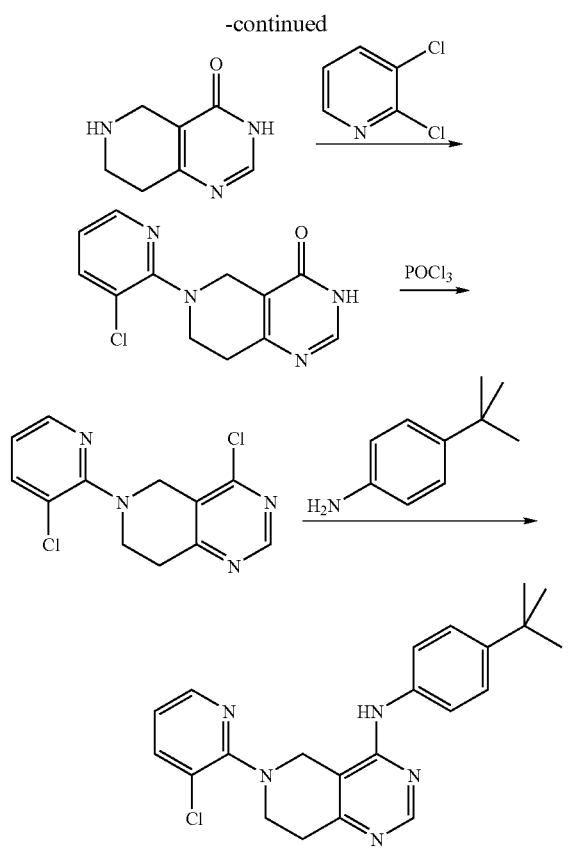

Synthetic Scheme 3

The 2-substituted pyrido[4,3-d]pyrimidin-4-one derivatives are prepared using the synthetic sequence given below. The intermediate 6-benzyl-5,6,7,8-tetrahydro-2-(methylthio)pyrido[4,3-d]pyrimidin-4(3H)-one is formed by reaction of ethyl 1-benzyl-3-oxopiperidine-4-carboxylate hydrochloride with thiourea. This intermediate methylthio derivative is then subjected to synthetic sequence outlined above (Scheme 2) to give the appropriate N-substituted-6-(pyridin-2-yl)-5,6,7,8-tetrahydro-2-(methylthio)pyrido[4,3-d]pyrimidin-4-amine derivative, which is oxidized to the corresponding sulfone derivative and in turn reacted with an appropriate nucleophile to give the analogous 2-substituted-N-substituted-6-(pyridin-2-yl)-5,6,7,8-tetrahydropyrido[4,3-d]pyrimidin-4-amine derivative. As a representative example, synthesis of N-(4-tert-butylphenyl)-6-(3-chloropyridin-2-yl)-5,6,7,8-tetrahydro-2-methoxypyrido[4,3-d]pyrimidin-4-amine is depicted in Scheme 3.

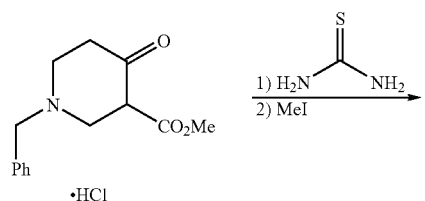

Synthetic Scheme 4

Conversely, 2-chloroacetamidine hydrochloride is reacted with an appropriate nucleophile to form an appropriate amidine derivative. The amidine is reacted with ethyl 1-benzyl-4-oxopiperidine-3-carboxylate hydrochloride to afford the intermediate 2-substituted-N-substituted-6-(pyridin-2-yl)-5,6,7,8-tetrahydropyrido[4,3-d]pyrimidin-4-amine derivative.

This intermediate pyrido[4,3-d]pyrimidin-4-amine is then subjected to the reaction sequence described in Scheme 2 to yield appropriately 2-substituted N-substituted-6-(pyridin-2-yl)-5,6,7,8-tetrahydropyrido[4,3-d]pyrimidin-4-amine derivative. As a representative example, synthesis of N-(4-tert-butylphenyl)-6-(3-chloropyridin-2-yl)-5,6,7,8-tetrahydro-2-(morpholinomethyl)pyrido[4,3-d]pyrimidin-4-amine is depicted in Scheme 4.

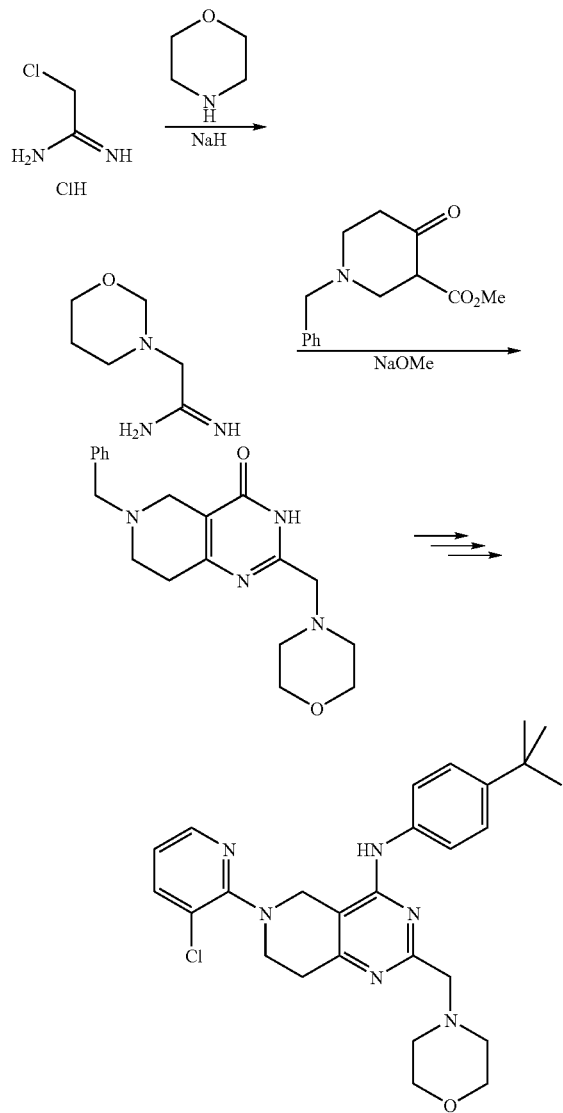

Synthetic Scheme 5

Appropriate N-aryl substituted-5,6,7,8-tetrahydro-6-arylpyrido[4,3-d]pyrimidin-4-amine, obtained by following synthetic scheme 2, are prepared by the reaction of the corresponding N-substituted-5,6,7,8-tetrahydropyrido[4,3-d]pyrimidin-4-amine with an appropriate aryl boronic acid in the presence of copper acetate and triethylamine. As a representative example, preparation of N-(4-(trifluoromethyl)phenyl)-5,6,7,8-tetrahydro-6-m-tolylpyrido[4,3-d]pyrimidin-4-amine is depicted in Scheme 5.

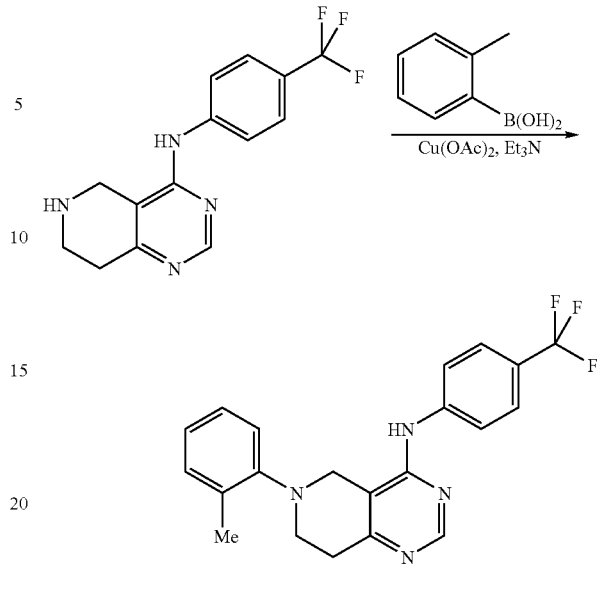

Synthetic Scheme 6

Appropriate 6-(pyridin-2-yl)-5,6,7,8-tetrahydro-N-(1,2,3,4-tetrahydro-4,4-dimethyl-1-substituted)quinolin-7-yl)pyrido[4,3-d]pyrimidin-4-amine derivatives are prepared starting from 1,2,3,4-tetrahydro-4,4-dimethyl-7-nitroquinoline. The nitroquinoline derivate is reacted with appropriate alkylating agent to give the N-substituted nitroquinoline, which is reduced using standard procedures known in the art to yield 7-aminoquinoline derivative. The resulting aminoquinoline derivated is then condensed with the appropriate 4-chloro-6-(pyridin-2-yl)-5,6,7,8-tetrahydropyrido[4,3-d]pyrimidine to give the desired 6-(pyridin-2-yl)-5,6,7,8-tetrahydro-N-(1,2,3,4-tetrahydro-4,4-dimethyl-1-substituted)quinolin-7-yl)pyrido[4,3-d]pyrimidin-4-amine derivative. As a representative example, preparation of the N-morpholionethyl derivative is depicted in Scheme 6.

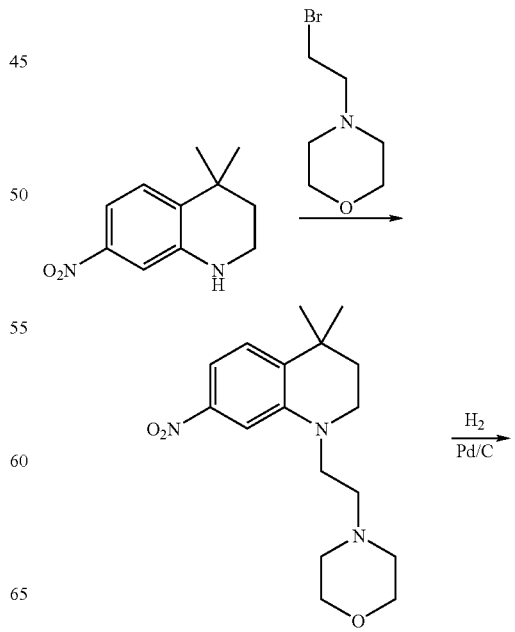

45

-continued

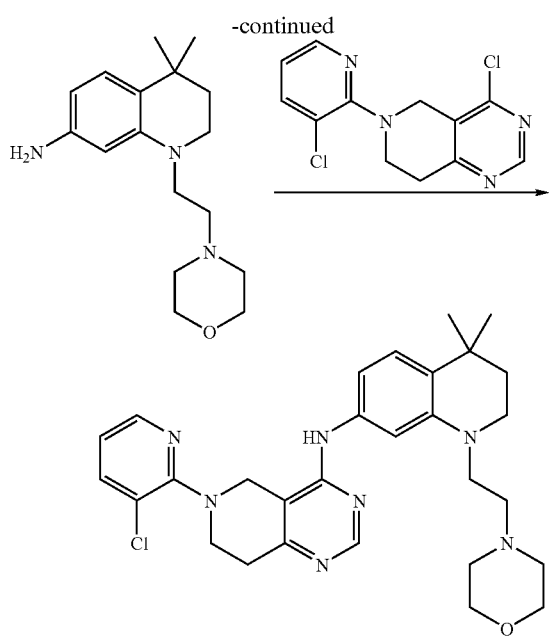

Synthetic Scheme 7

A similar sequence of reactions using substituted amidines, and set forth in the scheme presented below, gives rise to 2-substituted products. For example, trifluoromethyl amidine can be employed in the similar sequence of reactions to afford 2-trifluoromethyl substituted products.

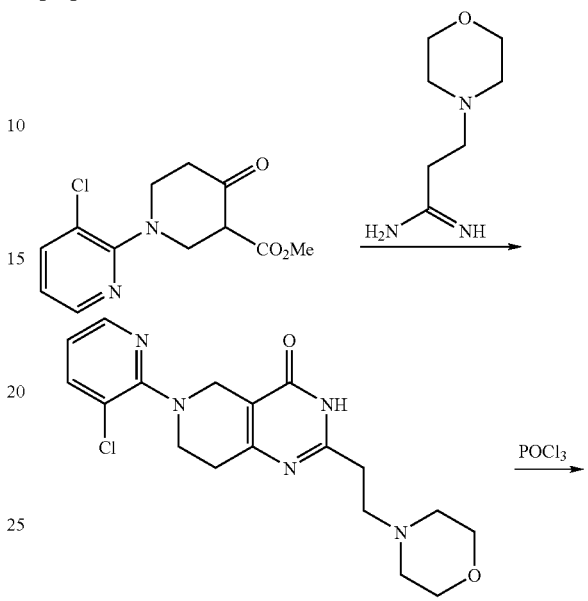

46

Synthetic Scheme 8

Similarly, another sequence of reactions, as depicted in Scheme 8, using substituted amidines can be employed to prepare 2-substituted derivatives.

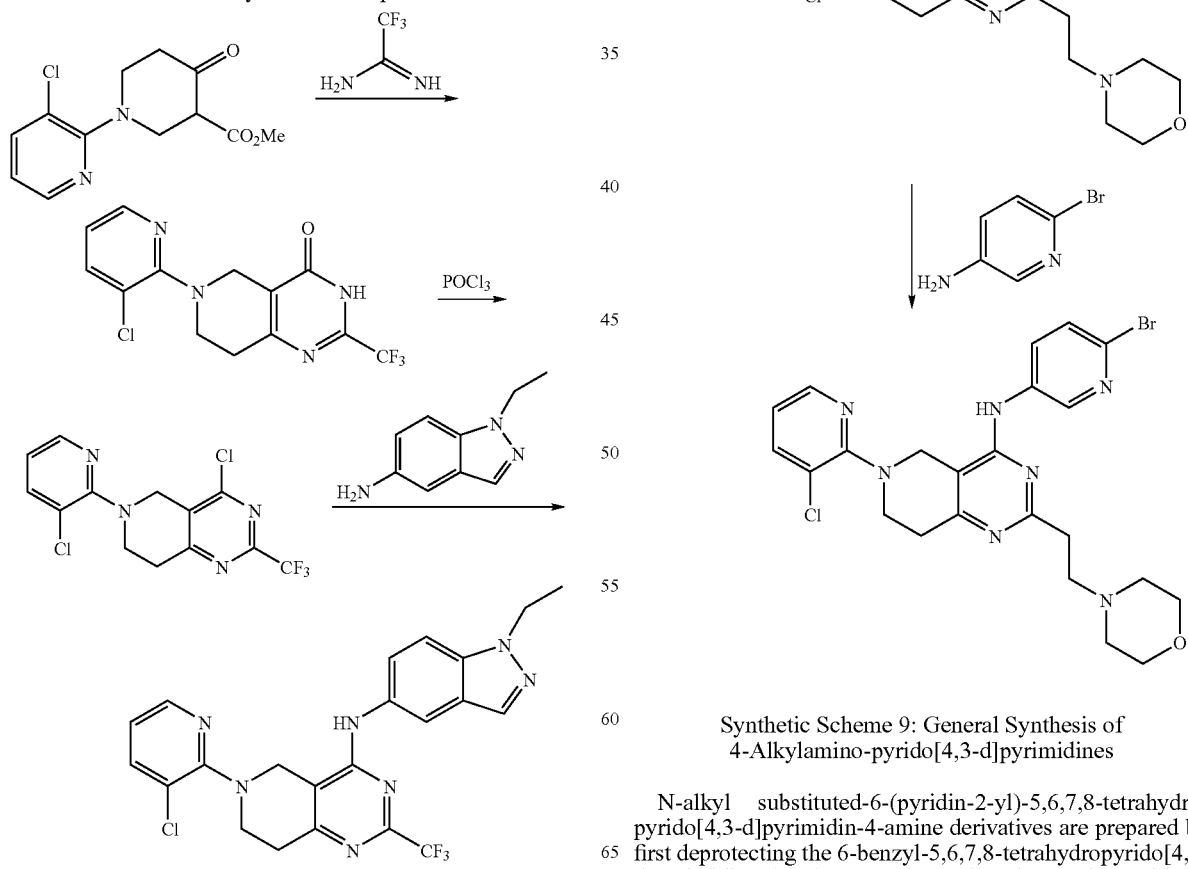

Synthetic Scheme 9: General Synthesis of 4-Alkylamino-pyrido[4,3-d]pyrimidines

N-alkyl substituted-6-(pyridin-2-yl)-5,6,7,8-tetrahydropyrido[4,3-d]pyrimidin-4-amine derivatives are prepared by first deprotecting the 6-benzyl-5,6,7,8-tetrahydropyrido[4,3-d]pyrimidin-4(4aH)-one and reacting the product with an appropriate 2-halo-pyridine to give the 6-(pyridin-2-yl)-5,6, 7,8-tetrahydropyrido[4,3-d]pyrimidin-4(4aH)-one which is reacted with POCl3 followed by condensation with an appropriate alkylamine to yield the appropriate the appropriate N-substituted-6-(pyridin-2-yl)-5,6,7,8-tetrahydropyrido[4,3-d]pyrimidin-4-amine. As a representative example, synthesis of N-(alkyl)-6-(3-chloropyridin-2-yl)-5,6,7,8-tetrahydropyrido[4,3-d]pyrimidin-4-amine is depicted in Scheme 9.

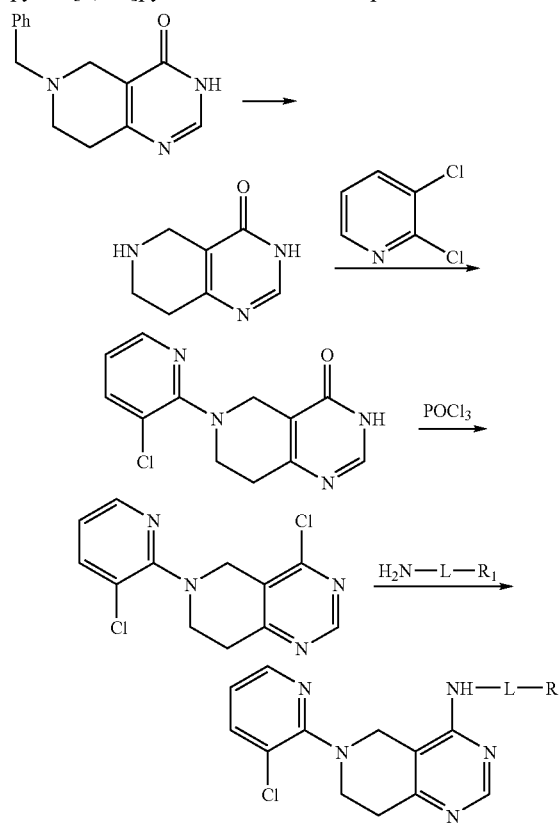

L=alkylene or heteroalkylene chain and R¹=substituted and unsubstituted carbocyclic or heterocyclic group.

Synthetic Scheme 10: General Synthesis of 2-Substituted pyrido[4,3-d]pyrimidines The 2-substituted pyrido[4,3-d]pyrimidin-4-one derivatives are prepared using the synthetic sequence given below. The intermediate N-substituted-6-(pyridin-2-yl)-5,6,7,8-tetrahydro-2-(methylthio)pyrido[4,3-d]pyrimidin-4-amine, as prepared following the synthetic Scheme 3, is oxidized to the corresponding sulfone derivative and in turn reacted with an appropriate nucleophile to give the analogous 2-substituted-N-substituted-6-(pyridin-2-yl)-5,6,7,8-tetrahydropyrido[4,3-d]pyrimidin-4-amine derivative.

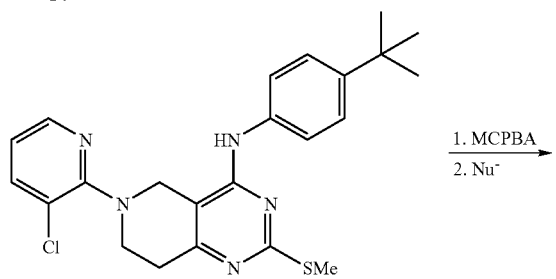

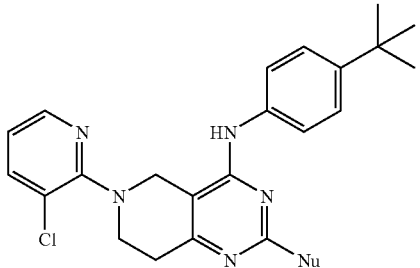

Nu=R4''-L'-Z'⁻; R⁴''=substituted and unsubstituted carbocyclic or heterocyclic group; L'=alkylene or heteroalkylene chain; and Z'⁻=S⁻, or O⁻.

Synthetic Scheme 11: General Synthesis of 6 substitiuted 5,6,7,8-tetrahydro-6-(5-methylpyridin-2-yl) pyrido[4,3-d]pyrimidine

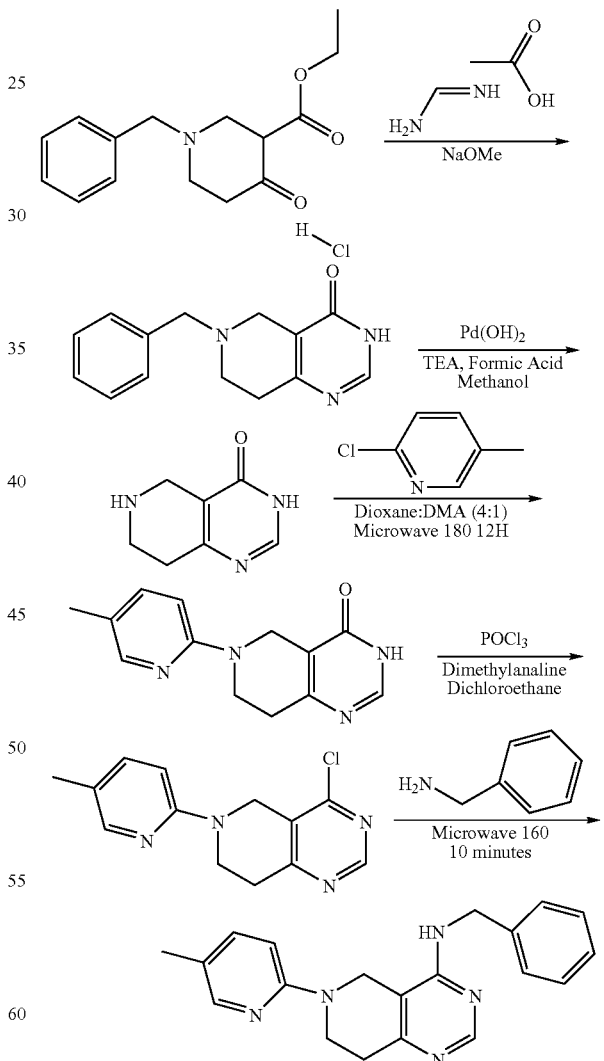

Organic Process Research & Development 2005, 9, 80–87

Various 6 substituted 5,6,7,8-tetrahydro-6-(5-methylpyridin-2-yl)pyrido[4,3-d]pyrimidines are prepared using a general procedure shown above. Ethyl 1-benzyl-4-oxopiperidine-3-carboxylate hydrochloride is reacted with formamidine acetate to yield 6-benzyl-5,6,7,8-tetrahydropyrido[4,3-d]pyrimidin-4(4aH)-one, which, in turn, is reduced to 5,6,7,8-tetrahydropyrido[4,3-d]pyrimidin-4(3H)-one. The intermediate coupled with 5 chloro 2 methyl pyridine to produce 5,6,7,8-tetrahydro-6-(5-methylpyridin-2-yl)pyrido[4,3-d]pyrimidin-4(3H)-one. Chlorination of the resulting product using POCl₃ and displacement of the chloride using various benzylamines via microwave displacement will afford various 6 substitiuted 5,6,7,8-tetrahydro-6-(5-methylpyridin-2-yl)pyrido[4,3-d]pyrimidines.

The following synthetic and biological examples are offered to illustrate this invention and are not to be construed in any way as limiting the scope of this invention. In the examples below, all temperatures are in degrees Celsius (unless otherwise indicated). The syntheses of these representative compounds are carried out in accordance with the methods set forth above and using the appropriate reagents, starting materials, and purification methods known to those skilled in the art.

Exemplary Compounds of the Invention

The following compounds have been prepared according to the methods of the invention. Corresponding compounds have been recited hereinabove and in the claims. Unless otherwise indicated, reactions in microwave were carried out in Emrys Optimizer or Smith Creator microwave models manufactured by Personal Chemistry, Inc.

Synthesis of Intermediates

Intermediate 1

6-Benzyl-5,6,7,8-tetrahydropyrido[4,3-d]pyrimidin-4(3H)-one

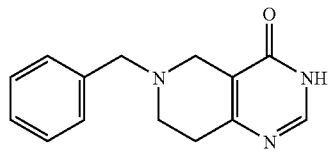

A mixture of ethyl 1-benzyl-4-oxopiperidine-3-carboxylate hydrochloride (50.0 g, 0.168 mol), formamidine acetate (16.2 g, 0.201 mol), 4.37 M of sodium methoxide in methanol (190 mL) and methanol (200 mL, 5 mol) was heated to 85° C. for 16 hour in a 350 ml sealed reaction vessel. The mixture was allowed to cool and reduced in vacuo. The residue was dissolved in 1N NaOH (150 ml) and poured over ice. Glacial acetic acid was added to the mixture until the pH of the mixture was 7 and a tan solid precipitated out. the solid was filtered, washed with water and cold ether, and dried on high vacuum to yield the title compound as a tan solid. (26.2 g, 61.4%).

MS: M+H=242.2.

$^1$H NMR (DMSO-d6): δ 2.29 (t, 5.8 Hz, 2H); 2.61 (t, 5.8 Hz, 2H); 3.26 (s, 2H); 3.64 (s, 2H); 7.21-7.36 (m, 6H); 7.96 (s, 1H).

Intermediate 2

6-Benzyl-4-chloro-5,6,7,8-tetrahydropyrido[4,3-d]pyrimidine

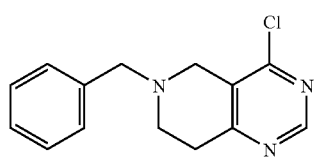

A mixture of 6-benzyl-5,6,7,8-tetrahydropyrido[4,3-d]pyrimidin-4(3H)-one (5.0 g, 0.02 mol), phosphoryl chloride (3.30 mL, 0.035 mol) and acetonitrile (80 mL) and DMF (catalytic amount) was heated to at 70° C. for 1 hour. The mixture was reduced in vacuo and the remaining black residue was taken up in dichloromethane (250 ml) and poured over ice. The mixture was carefully neutralized with the addition of solid sodium bicarbonate. The layers were separated and the organic dried over sodium sulfate and reduced in vacuo. The mixture was chromatographed using an ethyl acetate:hexanes (0-100%) gradient on an isco flash chromatography system. The combined pure fractions were reduced in vacuo to yield the title compound as a yellow oil (3 g, 57.8%).

MS: M+H=260.

$^1$H NMR (DMSO-d6): δ 8.80 (s, 1H). 7.40-7.24 (m, 5H), 3.76 (s, 2H), 3.57 (s, 2H), 2.92 (t, 2H), 2.80 (t, 2H).

EXAMPLES

Compound 1

6-(3-Chloropyridin-2-yl)-5,6,7,8-tetrahydro-N-[(4-difluoromethoxy)phenyl]pyrido[4,3-d]pyrimidin-4-amine

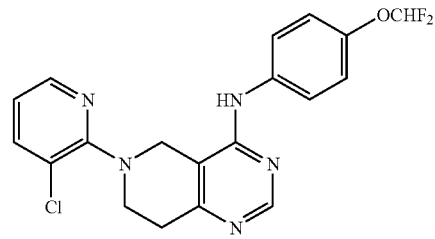

A. 6-Benzyl-5,6,7,8-tetrahydro-N-[(4-difluoromethoxy)phenyl]pyrido[4,3-d]pyrimidin-4-amine

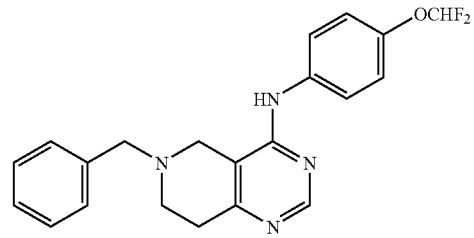

6-Benzyl-4-chloro-5,6,7,8-tetrahydropyrido[4,3-d]pyrimidine (1.09 g, 4.21 mmol) prepared as described above (Intermediate 2, 1.0 g, 3.86 mmol) was dissolved in anhydrous acetonitrile (3 mL) and 4-difluoromethoxyaniline was added (1.34 g, 8.42 mmol). The mixture was heated at 180° C. for 600 s in a microwave (Emrys Optimizer model, Personal Chemistry). The solvents were removed under vacuum to give the desired product as a beige powder (1.3 g, 94.2%). The crude product was used for the subsequent step.

B. 5,6,7,8-Tetrahydro-N-[(4-difluoromethoxy)phenyl]pyrido[4,3-d]pyrimidin-4-amine

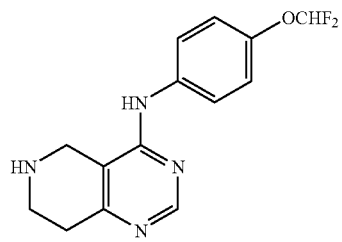

6-Benzyl-5,6,7,8-tetrahydro-N-[(4-difluoromethoxy)phenyl]pyrido[4,3-d]pyrimidin-4-amine (1.012 g, 2.65 mmol) was dissolved in methanol (20 mL) and palladium hydroxide (1.5 g, 20% wt) and ammonium formate (1.67 g, 26.46 mmol) were added. The mixture was heated at reflux for one hour and then 10 hours at room temperature under nitrogen. The mixture was filtered through celite and the filtrate concentrated to afford a solid which was taken up in saturated sodium bicarbonate (100 ml). The aqueous was extracted with ethyl acetate (3×100 ml). The organic layers were combined, washed with brine, dried over sodium sulfate and concentrated to leaved a tan solid. The crude solid was purified by column chromatography using a methanol:methylene chloride (0-20%) gradient. The combined pure fractions were reduced in vacuo to yield the title compound (0.201 g) as a yellow solid which was used directly in the next step

C. 6-(3-Chloropyridin-2-yl)-5,6,7,8-tetrahydro-N-[(4-difluoromethoxy)phenyl]pyrido[4,3-d]pyrimidin-4-amine

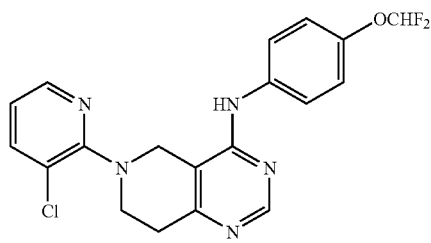

5,6,7,8-Tetrahydro-N-[(4-difluoromethoxy)phenyl]pyrido[4,3-d]pyrimidin-4-amine (0.091 g, 0.31 mmol) was dissolved in a mixture of dioxane/N,N-dimethylacetamide (4:1) (2 mL). To the mixture was added 2,3-dichloropyridine (0.092 g, 0.62 mmol) and N,N-diisopropylethylamine (0.081 mL, 0.47 mmol). The mixture was heated at 170° C. in a microwave (Emrys Optimizer model, Personal Chemistry) for 10 h. The mixture was allowed to cool to room temperature and poured into water (60 ml) and extracted with ethyl acetate (2×30 ml). The organic layers were combined, dried over Na$_2$SO$_4$, filtered, and evaporated to give a brown residue. The residue was purified using a gradient of ethyl acetate:hexane (0-100%) to give the desired compound as an off-white powder (0.38 g).

Compound 2

6-(3-Chloropyridin-2-yl)-5,6,7,8-tetrahydro-N-phenylpyrido[4,3-d]pyrimidin-4-amine

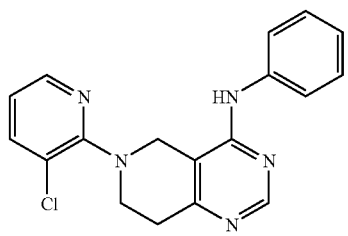

A. 6-Benzyl-5,6,7,8-tetrahydro-N-phenylpyrido[4,3-d]pyrimidin-4-amine

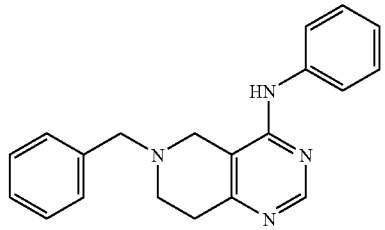

6-Benzyl-4-chloro-5,6,7,8-tetrahydropyrido[4,3-d]pyrimidine (Intermediate 2, 1.0 g, 3.86 mmol) was dissolved in anhydrous acetonitrile (3 mL) and aniline was added (0.39 mL, 4.24 mmol). The mixture was heated at 180° C. for 600 s in a microwave (Emrys Optimizer model, Personal Chemistry). The solvents were removed under vacuum to give the desired product as a beige powder (1.5 g, quant.). The crude product was used as such for the subsequent step.

MS: M+H=317.

B. 5,6,7,8-Tetrahydro-N-phenylpyrido[4,3-d]pyrimidin-4-amine

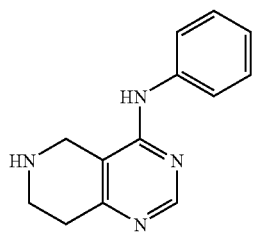

6-Benzyl-5,6,7,8-tetrahydro-N-phenylpyrido[4,3-d]pyrimidin-4-amine (1.5 g, 3.8 mmol) was dissolved in methanol (25 mL) and palladium hydroxide was added (1.5 g, 20% wt). The mixture was shaken on a Parr Shaker under H$_2$ (g) atmosphere (60 PSI) for 1 day. The mixture was filtered through celite and evaporated to give 0.95 g of material as a yellow solid (quant.), which was used as such for the next step.

MS: M+H=227.

C. 6-(3-Chloropyridin-2-yl)-5,6,7,8-tetrahydro-N-phenylpyrido[4,3-d]pyrimidin-4-amine

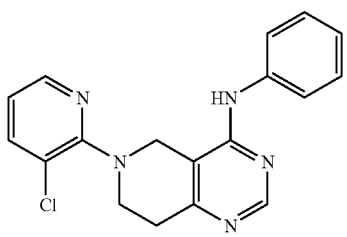

5,6,7,8-Tetrahydro-N-phenylpyrido[4,3-d]pyrimidin-4-amine (500 mg, 2.2 mmol) was dissoled in a mixture of dioxane/N,N-dimethylacetamide (4:1) (2 mL). To the mixture was added 2,3-dichloropyridine (423 mg, 2.86 mmol) and N,N-diisopropylethylamine (0.38 mL, 2.2 mmol). The mixture was heated at 150° C. in a microwave (Emrys Optimizer model, Personal Chemistry) for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified using a gradient of ethyl acetate:hexane (0-100%) to give the desired compound as an off-white powder (190 mg).

$^1$H NMR (DMSO-d6): δ 8.58 (s, 1H). 8.40 (s, 1H) 8.28 (dd, 4.8 Hz, 1.7 Hz, 1H); 8.28 (dd, 4.8 Hz, 1.7 Hz, 1H); 7.88 (dd, 7.8 Hz, 1.7 Hz, 1H); 7.67-7.63 (m, 2H); 7.28-7.34 (m, 2H); 7.10-7.03 (m, 2H); 4.39 (s, 2H) 3.62 (t, 5.8 Hz, 2H) 2.88 (t, 5.8 Hz, 2H).

Compound 3

6-(3-Chloropyridin-2-yl)-N-(4-fluorophenyl)-5,6,7,8-tetrahydropyrido[4,3-d]pyrimidin-4-amine

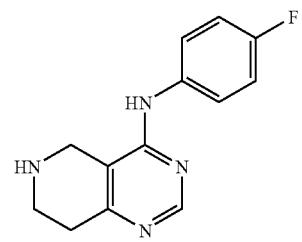

A. 6-Benzyl-N-(4-fluorophenyl)-5,6,7,8-tetrahydropyrido[4,3-d]pyrimidin-4-amine

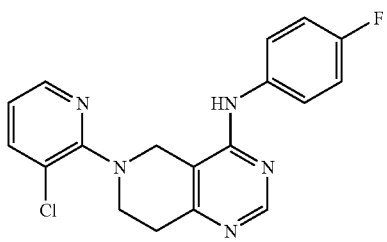

6-Benzyl-4-chloro-5,6,7,8-tetrahydro-pyrido[4,3-d]pyrimidine (Intermediate 2, 0.25 g, 0.97 mmol) was dissolved in anhydrous acetonitrile (3 mL) and 4-fluorobenzenamine was added (0.10 mL, 1.06 mmol). The mixture was heated at 200° C. for 600 s in a microwave (Emrys Optimizer model, Personal Chemistry). The solvents were removed under vacuum to give the desired product as a beige powder (0.313 g, 97%).
MS: M+H=335.

B. N-(4-Fluorophenyl)-5,6,7,8-tetrahydropyrido[4,3-d]pyrimidin-4-amine

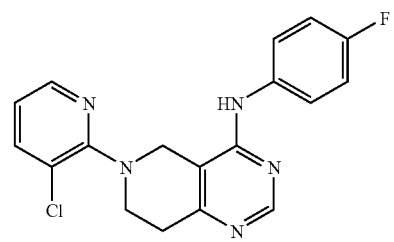

6-Benzyl-N-(4-fluorophenyl)-5,6,7,8-tetrahydropyrido[4,3-d]pyrimidin-4-amine (0.64 g, 1.9 mmol) was dissolved in methanol (25 mL) and palladium hydroxide was added (0.5 g, 20% wt). The mixture was shaken on a Parr Shaker under H$_2$ (g) atmosphere (60 PSI) for 1 day. The mixture was filtered through celite and evaporated to give 0.47 g of material which was used as such for the next step.
MS: M+H=245.

C. 6-(3-Chloropyridin-2-yl)-N-(4-fluorophenyl)-5,6,7,8-tetrahydropyrido[4,3-d]pyrimidin-4-amine

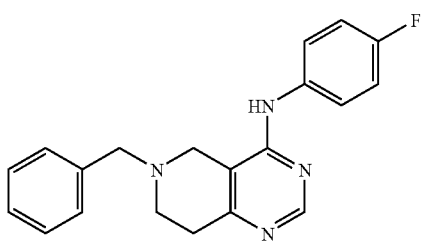

N-(4-Fluorophenyl)-5,6,7,8-tetrahydropyrido[4,3-d]pyrimidin-4-amine (0.47 g, 1.92 mmol) was dissolved in a mixture of dioxane/N,N-dimethylacetamide (4:1) (3 mL). To the mixture was added 2,3-dichloropyridine (420 mg, 2.86 mmol) and N,N-diisopropylethylamine (0.38 mL, 2.2 mmol). The mixture was heated at 150° C. in a Personal Chemistry microwave for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified by silica gel chromatography using a gradient of ethyl acetate:hexane (0-100%) to give the desired compound as an off-white powder (200 mg, 30%).

$^1$H NMR (DMSO-d6): δ 8.62 (s, 1H); 8.38 (s, 1H); 8.28 (dd, 4.7 Hz, 1.4 Hz, 1H) 7.89 (dd, 7.8 Hz, 1.4 Hz, 1H); 7.67-7.61 (m, 2H); 7.19-7.12 (m, 2H); 7.08 (dd, 7.8 Hz, 4.7 Hz, 1H); 4.38 (s, 2H); 3.61 (t, 5.4 Hz, 2H); 2.88 (t, 5.4 Hz, 2H).

Compound 4

6-(3-Chloropyridin-2-yl)-N-(6-(trifluoromethyl)pyridin-3-yl)-5,6,7,8-tetrahydropyrido[4,3-d]pyrimidin-4-amine

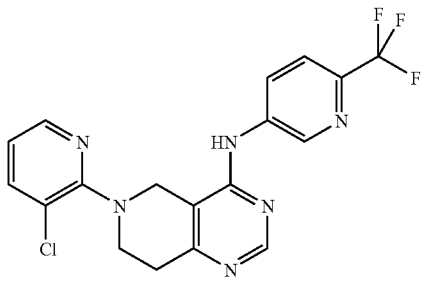

A. 6-Benzyl-N-(6-(trifluoromethyl)pyridin-3-yl)-5,6,7,8-tetrahydropyrido[4,3-d]pyrimidin-4-amine

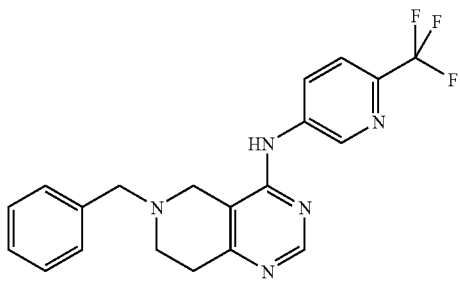

6-Benzyl-4-chloro-5,6,7,8-tetrahydropyrido[4,3-d]pyrimidine (0.5 g, 1.93 mmol) was dissolved in anhydrous dioxane (3 mL) and 6-trifluoromethylpyridin-3-ylamine was added (469 mg, 2.9 mmol), followed by HI/H$_2$O (0.3 mL, 47%). The mixture was heated at 130° C. for 600 s in a Personal Chemistry microwave. The solvents were removed under vacuum and the residue was dissolved in ethyl acetate and washed with sat. NaHCO$_3$ and brine. The organic layer was dried over Na$_2$SO$_4$, filtered and evaporated to give the product as an orange solid (700 mg, 95% crude). The crude product was used for the subsequent step.

MS: M+H=386.

B. N-(6-(Trifluoromethyl)pyridin-3-yl)-5,6,7,8-tetrahydropyrido[4,3-d]pyrimidin-4-amine

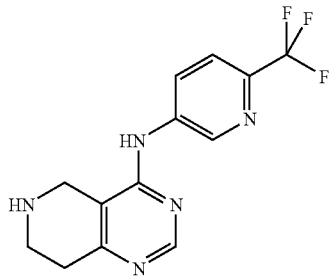

6-Benzyl-N-(6-(trifluoromethyl)pyridin-3-yl)-5,6,7,8-tetrahydropyrido[4,3-d]pyrimidin-4-amine (1.7 g, 4.4 mmol) was dissolved in methanol (25 mL) and palladium hydroxide was added (0.2 g, 20% wt). The mixture was shaken on a Parr Shaker under H$_2$(g) atmosphere (60 PSI) for 1 day. The mixture was filtered through celite and evaporated to give 1.3 g (quant.) as an orange oil, which was used as such for the next step.

MS: M+H=296.

C. 6-(3-Chloropyridin-2-yl)-N-(6-(trifluoromethyl)pyridin-3-yl)-5,6,7,8-tetrahydropyrido[4,3-d]pyrimidin-4-amine

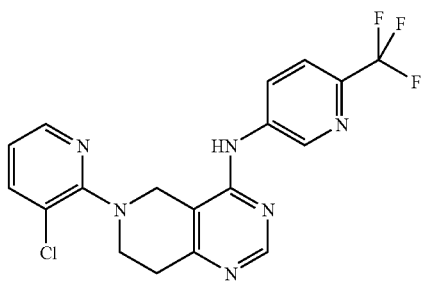

N-(6-(Trifluoromethyl)pyridin-3-yl)-5,6,7,8-tetrahydropyrido[4,3-d]pyrimidin-4-amine (130 mg, 0.44 mmol) was dissolved in a mixture of dioxane/N,N-dimethylacetamide (4:1) (2 mL). To the mixture was added 2,3-dichloropyridine (98 mg, 0.66 mmol) and N,N-diisopropylethylamine (0.11 mL, 0.66 mmol). The mixture was heated at 150° C. in a Personal Chemistry microwave for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified using a gradient of ethyl acetate:hexane (0-100%) to give the desired compound as an off-white powder (50 mg, 28%).

$^1$H NMR (DMSO-d6): δ 9.15 (s, 1H). 9.05 (d, 2.4 Hz, 1H); 8.54 (s, 1H); 8.44 (dd, 8.7 Hz, 2.4 Hz, 1H); 8.29 (dd, 4.6 Hz, 1.6 Hz, 1H); 7.90 (dd, 7.8 Hz, 1.6 Hz, 1H); 7.85 (d, 8.7 Hz, 1H); 7.09 (dd, 7.8 Hz, 4.6 Hz, 1H); 4.45 (s, 2H); 3.63 (t, 5.6 Hz, 2H); 2.95 (t, 5.6 Hz, 2H).

Compound 5

N-(6-(Trifluoromethyl)pyridin-3-yl)-5,6,7,8-tetrahydro-6-(3-(methylsulfonyl)pyridin-2-yl)pyrido[4,3-d]pyrimidin-4-amine

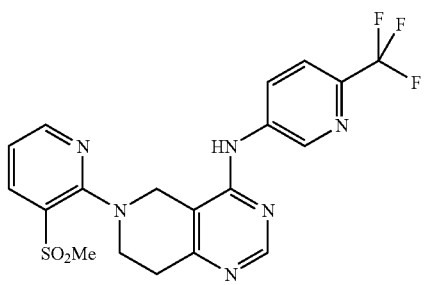

The title compound was prepared according to the procedure described for Compound 4 and reacting N-(6-(trifluoromethyl)pyridin-3-yl)-5,6,7,8-tetrahydropyrido[4,3-d]pyrimidin-4-amine (140 mg, 0.47 mmol) with 2-chloro-3-(methylsulfonyl)pyridine (Ponticello, *JOC,* 44(17), 1979)

(0.115 g, 0.06 mmol) in the presence of N,N-diisopropylethylamine (0.17 mL, 0.98 mmol) to give the desired Compound 5 as an off-white powder (55 mg, 26%).

$^1$H NMR (DMSO-d6): δ 9.07 (s, 1H). 9.04 (d, 2.3 Hz, 1H) 8.74 (dd, 4.7 Hz, 1.9 Hz, 1H); 8.46 (dd, 8.7 Hz, 2.3 Hz, 1H); 8.56 (s, 1H); 8.37 (dd, 7.8 Hz, 1.9 Hz, 1H); 7.85 (d, 8.7 Hz, 1H); 7.52 (dd, 7.8 Hz, 4.7 Hz, 1H); 4.39 (s, 2H); 3.33 (s, 3H); 3.53 (t, 5.7 Hz, 2H); 2.99 (t, 5.7 Hz, 2H).

Compound 6

6-(3-Chloropyridin-2-yl)-5,6,7,8-tetrahydro-N-(4-(trifluoromethylsulfonyl) phenyl)pyrido[4,3-d]pyrimidin-4-amine

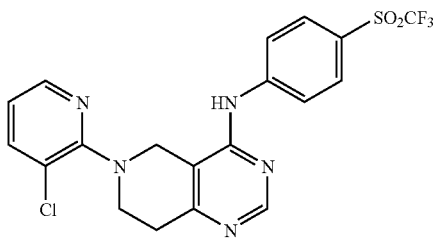

A. 6-Benzyl-5,6,7,8-tetrahydro-N-(4-(trifluoromethylsulfonyl)phenyl)pyrido[4,3-d]pyrimidin-4-amine

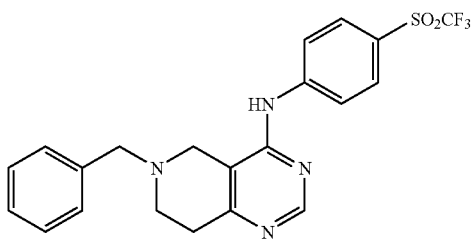

The title compound was prepared substantially according to the procedure given for Compound 4A, using 6-benzyl-4-chloro-5,6,7,8-tetrahydropyrido[4,3-d]pyrimidine (0.2 g, 0.77 mmol), and 4-(trifluoromethylsulphonyl)aniline (0.27 g, 1.2 mmol) to give the desired N-benzyl intermediate as a brown solid (278 mg. 82%).

MS: M+H=449.

B. 5,6,7,8-Tetrahydro-N-(4-(trifluoromethylsulfonyl) phenyl)pyrido[4,3-d]pyrimidin-4-amine

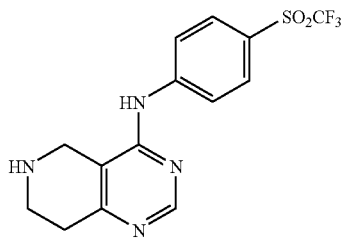

6-Benzyl-5,6,7,8-tetrahydro-N-(4-(trifluoromethylsulfonyl)phenyl)pyrido[4,3-d]pyrimidin-4-amine (270 mg, 0.55 mmol) was dissolved in anhydrous chloroform (10 mL) and 1-chloroethylchloroformate was added (0.18 mL, 1.65 mmol). After stirring for 30 min, N,N-diisopropylethylamine was added (0.24 mL, 1.65 mmol) and the mixture was stirred for an additional 2 h. The chloroform was removed under vacuum and 30 ml of methanol was added and the mixture was heated for 30 min. Upon reaction completion, the methanol was removed and the residue was dissolved in ethyl acetate and washed with sat. NaHCO$_3$ and brine. The organic layer was dried over Na$_2$SO$_4$, filtered and evaporated to give the product (163 mg, 83%).

M+H=359.

C. 6-(3-Chloropyridin-2-yl)-5,6,7,8-tetrahydro-N-(4-(trifluoromethylsulfonyl) phenyl)pyrido[4,3-d]pyrimidin-4-amine

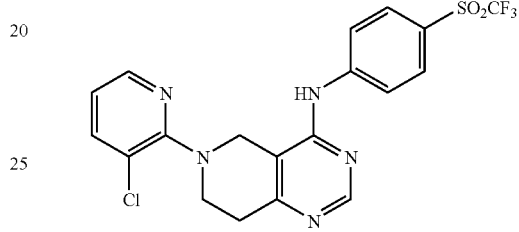

The title compound was prepared according to the procedure given for Compound 4C using 5,6,7,8-tetrahydro-N-(4-(trifluoromethylsulfonyl)phenyl)pyrido[4,3-d]pyrimidin-4-amine (160 mg, 0.45 mmol), 2,3-dichloropyridine (135 mg, 0.9 mmol) and N,N-diisopropylethylamine (0.16 mL, 0.9 mmol) to give the desired compound as an off-white powder (40 mg, 19%).

Compound 7

5,6,7,8-tetrahydro-6-(3-(methylsulfonyl)pyridin-2-yl)-N-(4-(trifluoromethylsulfonyl)phenyl)pyrido[4,3-d]pyrimidin-4-amine

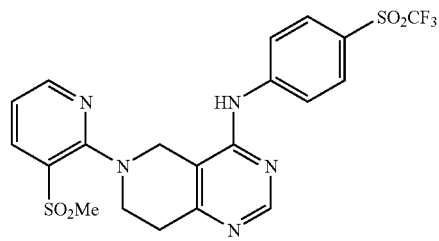

The title compound was prepared according to the procedure given for Compound 4C. using 5,6,7,8-tetrahydro-N-(4-(trifluoromethylsulfonyl) phenyl)pyrido[4,3-d]pyrimidin-4-amine (308 mg, 0.86 mmol), 2-chloro-3-(methylsulfonyl)pyridine (Ponticello, *JOC,* 44(17), 1979) (0.200 g, 1.04 mmol) and N,N-diisopropylethylamine (0.25 ml, 1.43 mmol) to give the desired compound as an off-white powder (75 mg, 19%).

$^1$H NMR (DMSO-d6): δ 9.28 (s, 1H). 8.74 (dd, 4.8 Hz, 1.8 Hz, 1H); 8.64 (s, 1H); 8.37 (dd, 7.8 Hz, 1.8 Hz, 1H); 8.20 (d, 9.0 Hz, 2H); 8.02 (d, 9.0 Hz, 2H); 7.51 (dd, 7.8 Hz, 4.8 Hz, 1H); 4.41 (s, 2H); 3.53 (t, 5.6 Hz, 2H); 3.31 (s, 3H); 3.0 (t, 5.6 Hz, 2H);

Compound 8

5,6,7,8-Tetrahydro-N-(2,3-dihydrobenzo[b][1,4]dioxin-6-yl)-6-m-tolylpyrido[4,3-d]pyrimidin-4-amine

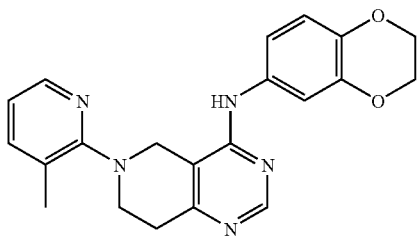

A. 6-Benzyl-5,6,7,8-tetrahydro-N-(2,3-dihydrobenzo[b][1,4]dioxin-6-yl)pyrido[3,4-d]pyrimidin-4-amine

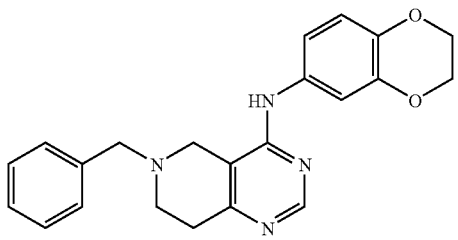

The title compound can be prepared using the general procedure set forth for Compound 1, above, using 2,3-dihydrobenzo[b][1,4]dioxin-6-amine (0.32 mL, 2.63 mmol) and 6-benzyl-4-chloro-5,6,7,8-tetrahydropyrido[3,4-d]pyrimidine (Compound 1B) (0.621 g, 2.39 mmol) in acetonitrile (3 mL).

B. 5,6,7,8-Tetrahydro-N-(2,3-dihydrobenzo[b][1,4]dioxin-6-yl)pyrido[4,3-d]pyrimidin-4-amine

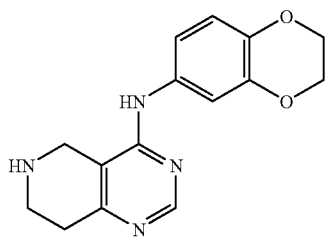

A mixture of 6-benzyl-5,6,7,8-tetrahydro-N-(2,3-dihydrobenzo[b][1,4]dioxin-6-yl)pyrido[3,4-d]pyrimidin-4-amine (0.742 g, 1.98 mmol), ammonium formate (1.25 g, 19.83 mmol) and palladium, 10% wt. on activated carbon (75 mg) in methanol (10 mL) is heated to 60° C. for 2 h. The mixture is cooled to r.t. and filtered over celite. The filtrate is concentrated under reduced pressure to give a white solid which is dissolved in water. The mixture is extracted twice with a 3:1 mixture of chloroform: isoproanol. The combined organic extracts are dried over sodium sulfate and concentrated to dryness to give the title compound.

C. 5,6,7,8-Tetrahydro-N-(2,3-dihydrobenzo[b][1,4]dioxin-6-yl)-6-m-tolylpyrido[4,3-d]pyrimidin-4-amine 5,6,7,8-Tetrahydro-N-(2,3-dihydrobenzo[b][1,4]dioxin-6-yl)pyrido[4,3-d]pyrimidin-4-amine (110 mg, 0.39 mmol) was dissolved in anhydrous THF (2 mL). To the mixture was added m-tolylboronic acid (105 mg, 0.78 mmol), Cu(OAc)$_2$ (141 mg, 0.78 mmol) and triethylamine (0.68 g, 0.095 mL) and 390 mg of crushed, activated 4 A molecular seives. The mixture was agitated for 6 h and the solvent was removed under vacuum. The residue was purified using a gradient of ethyl acetate:hexane (0-100%) to give the desired compound as reddish powder (14 mg, 9.6%).

Compound 9

N-(4-(Trifluoromethyl)phenyl)-5,6,7,8-tetrahydro-6-phenylpyrido[4,3-d]pyrimidin-4-amine

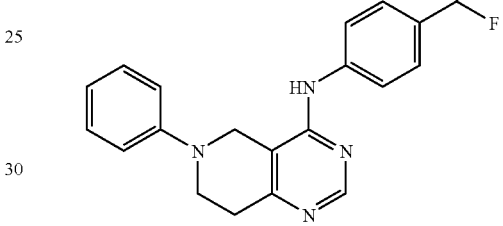

The (5,6,7,8-Tetrahydro-pyrido[4,3-d]pyrimidin-4-yl)-(4-trifluoromethylphenyl)amine (100 mg, 0.34 mmol) was dissolved in anhydrous THF (2 mL). To the mixture was added phenylboronic acid (83 mg, 0.68 mmol), Cu(OAc)$_2$ (124 mg, 0.68 mmol) and triethylamine (0.68 g, 0.095 mL). The mixture was agitated for 6 h and the solvent was removed under the vacuum. The residue was purified using a gradient of ethyl acetate:hexane (0-100%) to give the desired compound as reddish powder (8.0 mg, 6.0%).

$^1$H NMR (DMSO-d6): δ 8.82 (s, 1H). 8.50 (s, 1H); 7.96 (d, 8.8 Hz, 2H); 7.71 (d, 8.8 Hz, 2H); 7.32-7.26 (m, 2H); 7.20-7.15 (m, 2H); 6.85-6.80 (m, 1H); 4.27 (s, 2H); 3.61 (t, 5.8 Hz, 2H); 2.90 (t, 5.8 Hz, 2H).

Compound 10

N-(4-(Trifluoromethyl)phenyl)-5,6,7,8-tetrahydro-6-o-tolylpyrido[4,3-d]pyrimidin-4-amine

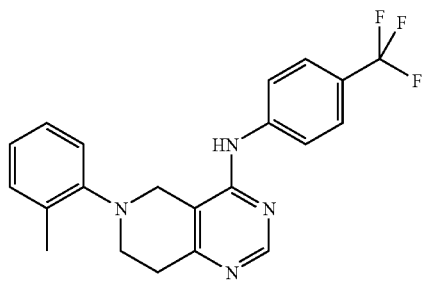

N-(4-(Trifluoromethyl)phenyl)-5,6,7,8-tetrahydropyrido[4,3-d]pyrimidin-4-amine (100 mg, 0.34 mmol) was dissolved in anhydrous THF (2 mL). To the mixture was added o-tolylboronic acid (92 mg, 0.68 mmol), Cu(OAc)$_2$ (124 mg, 0.68 mmol) and triethylamine (0.68 g, 0.095 mL). The mixture was agitated for 6 h and the solvent was removed under a vacuum. The residue was purified using a gradient of ethyl acetate:hexane (0-100%) to give the desired compound as reddish powder (6.0 mg, 5%).

Compound 11

N-(4-(Trifluoromethyl)phenyl)-5,6,7,8-tetrahydro-6-m-tolylpyrido[4,3-d]pyrimidin-4-amine

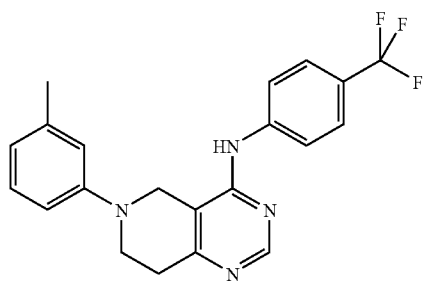

N-(4-(Trifluoromethyl)phenyl)-5,6,7,8-tetrahydropyrido[4,3-d]pyrimidin-4-amine (100 mg, 0.34 mmol) was dissolved in anhydrous THF (2 mL). To the mixture was added m-tolylboronic acid (92 mg, 0.68 mmol), Cu(OAc)$_2$ (124 mg, 0.68 mmol) and triethylamine (0.68 g, 0.095 mL). The mixture was agitated for 6 h and the solvent was removed under a vacuum. The residue was purified using a gradient of ethyl acetate:hexane (0-100%) to give the desired compound as reddish powder (6.2 mg, 5%).

$^1$H NMR (DMSO-d6): δ 8.81 (s, 1H). 8.50 (s, 1H); 7.97 (d, 8.8 Hz, 2H); 7.71 (d, 8.8 Hz, 2H); 7.19-7.14 (m, 1H); 7.01-6.94 (m, 2H); 6.65 (d, 7.6 Hz, 1H); 4.25 (s, 2H); 3.58 (t, 5.6 Hz, 2H); 2.89 (t, 5.6 Hz, 2H); 2.30 (s, 3H).

Compound 12

N-(4-(Trifluoromethyl)phenyl)-5,6,7,8-tetrahydro-6-p-tolylpyrido[4,3-d]pyrimidin-4-amine

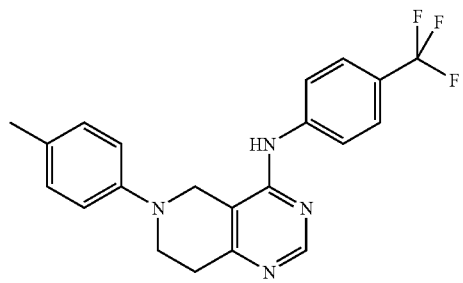

N-(4-(Trifluoromethyl)phenyl)-5,6,7,8-tetrahydropyrido[4,3-d]pyrimidin-4-amine (100 mg, 0.34 mmol) was dissolved in anhydrous THF (2 mL). To the mixture was added p-tolylboronic acid (92 mg, 0.68 mmol), Cu(OAc)$_2$ (124 mg, 0.68 mmol) and triethylamine (0.68 g, 0.095 mL). The mixture was agitated for 6 h and the solvent was removed under a vacuum. The residue was purified using a gradient of ethyl acetate:hexane (0-100%) to give the desired compound as reddish powder (12.8 mg, 10%).

$^1$H NMR (DMSO-d6): δ 8.80 (s, 1H). 8.49 (s, 1H); 7.96 (d, 8.7 Hz, 2H); 7.7 (d, 8.7 Hz, 2H); 7.10 (d, 9.1 Hz, 2H); 7.07 (d, 9.1 Hz, 2H); 4.21 (s, 2H); 3.54 (t, 5.7 Hz, 2H); 2.88 (t, 5.7 Hz, 2H); 2.23 (s, 3H).

Compound 13

6-[6-(3-Chloro-pyridin-2-yl)-5,6,7,8-tetrahydro-pyrido[4,3-d]pyrimidin-4-ylamino]-3,3-dimethyl-1,3-dihydro-indol-2-one

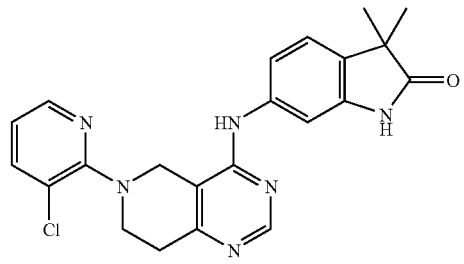

A. 6-amino-3,3-dimethylindolin-2-one

A mixture of 3,3-dimethyl-6-nitroindolin-2-one (1.2 g, 5.8 mmol) (Mertens et al, *J. Med. Chem.* 30:1279, 1987), 10% Pd—C (100 mg), and MeOH (100 mL) was stirred under hydrogen atmosphere (1 atm) for 10 h. The catalyst was filtered out and the filtrate was concentrated. The residue was purified by column to give an off-white solid (700 mg).

MS: M+H=177.

$^1$H NMR (d6-DMSO): 10.01 (s, 1H), 6.84 (d, 1H, J=8.0 Hz), 6.13-6.10 (m, 2H), 5.01 (s, 2H), 1.15 (s, 6H).

B. 6-(6-(3-chloropyridin-2-yl)-5,6,7,8-tetrahydropyrido[4,3-d]pyrimidin-4-ylamino)-3,3-dimethylindolin-2-one A mixture of 6-amino-3,3-dimethylindolin-2-one (156 mg), 4-chloro-6-(3-chloropyridin-2-yl)-5,6,7,8-tetrahydropyrido[4,3-d]pyrimidine (100 mg), and CH$_3$CN (5 mL) was run in a Microwave Reactor at 180° C. for 1 h. After cooling, the mixture was treated with sat. aq. Na$_2$CO$_3$ and extracted with EtOAc (30 mL×3). The combined organic layers were washed with brine, dried (Na$_2$SO$_4$) and concentrated. The residue was purified by column to give an off-white solid (120 mg, 80%).

$^1$H NMR (d6-DMSO): 10.32 (s, 1H), 8.54 (s, 1H), 8.40 (s, 1H), 8.28 (dd, 1H, J=5.2, 1.6 Hz), 7.89 (dd, 1H, J=8.0, 1.6 Hz), 7.30 (s, 1H), 7.19 (s, 2H), 7.08 (dd, 1H, J=8.0, 4.8 Hz), 4.38 (s, 2H), 3.61 (t, 2H, J=6.0 Hz), 2.88 (t, 2H, J=5.6 Hz), 1.24 (s, 6H).

Compound 14

1-{6-[6-(3-Chloro-pyridin-2-yl)-5,6,7,8-tetrahydro-pyrido[4,3-d]pyrimidin-4-ylamino]-3,3-dimethyl-2,3-dihydro-indol-1-yl}-ethanone

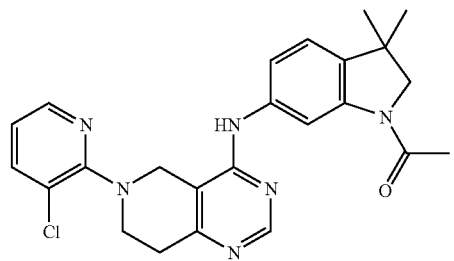

-continued

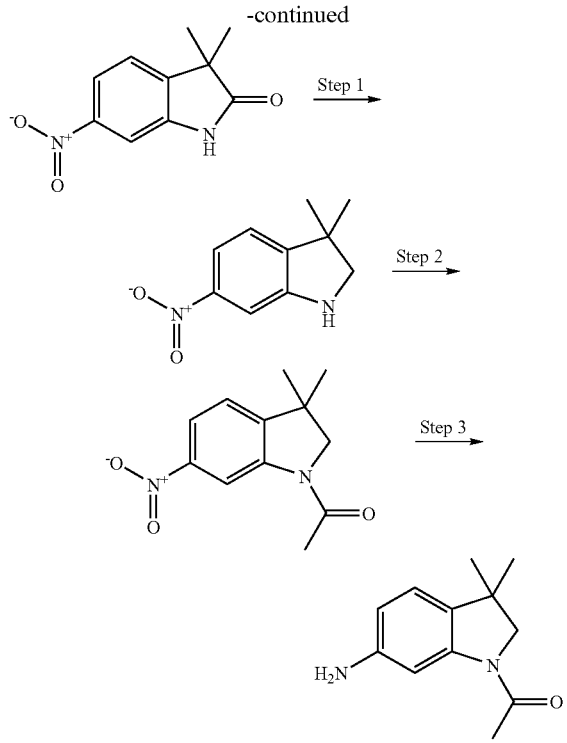

A. 3,3-dimethyl-6-nitroindoline

To a stirred solution of 3,3-dimethyl-6-nitroindolin-2-one (0.6 g, 3 mmol) (Mertens et al., *J. Med. Chem.* 30:1279, 1987) in THF (40 mL) at 0° C. under $N_2$ was added 2.0 M solution of $BH_3.Me_2S$ complex in THF (10 mL, 20 mmol). The mixture was stirred at rt for 10 h, and then quenched by addition of water (10 mL) and concentrated HCl (20 mL). The mixture was further stirred at rt for 5 h, and then basified with sat. aq. $Na_2CO_3$ and extracted with EtOAc (50 mL×3). The combined organic layers were washed with brine, dried ($Na_2SO_4$) and concentrated to give an orange syrup.

MS: M+H=193.

B. 1-(3,3-dimethyl-6-nitroindolin-1-yl)ethanone

To a stirred solution of 3,3-dimethyl-6-nitroindoline (450 mg) in $CH_2Cl_2$ (15 mL) and $Et_3N$ (0.6 mL) at −10° C. was added acetyl chloride (180 μL, 2.5 mmol). The mixture was stirred at rt overnight and quenched by addition of sat. aq. $NaHCO_3$, and extracted with EtOAc (30 mL×3). The combined organic layers were washed with brine, dried ($MgSO_4$) and concentrated. The residue was purified by column to give a light yellow solid (390 mg, 71% for two steps).

MS: M+H=235.

C. 1-(6-amino-3,3-dimethylindolin-1-yl)ethanone

A mixture of 1-(3,3-dimethyl-6-nitroindolin-1-yl)ethanone (300 mg), 10% Pd—C (50 mg), and EtOH (50 mL) was stirred under hydrogen atmosphere (1 atm) for 3 h. The catalyst was filtered out and the filtrate was concentrated to give a light yellow solid (260 mg).

MS: M+H=205.

D. 1-{6-[6-(3-chloro-pyridin-2-yl)-5,6,7,8-tetrahydro-pyrido[4,3-d]pyrimidin-4-ylamino]-3,3-dimethyl-2,3-dihydro-indol-1-yl}-ethanone A mixture of 1-(6-amino-3,3-dimethylindolin-1-yl)ethanone (80 mg), 4-chloro-6-(3-chloropyridin-2-yl)-5,6,7,8-tetrahydropyrido[4,3-d]pyrimidine (80 mg), and $CH_3CN$ (5 mL) was run in a Microwave Reactor at 180° C. for 1 h. After cooling, the mixture was treated with sat. aq. $Na_2CO_3$ and extracted with EtOAc (30 mL×3). The combined organic layers were washed with brine, dried ($Na_2SO_4$) and concentrated. The residue was purified by column to give a light yellow solid (75 mg).

$^1$H NMR (d6-DMSO): 8.61 (s, 1H), 8.34 (s, 1H), 8.28 (dd, 1H, J=4.8, 1.6 Hz), 8.19 (d, 1H, J=1.6 Hz), 7.88 (dd, 1H, J=8.0, 1.6 Hz), 7.35 (dd, 1H, J=8.0, 2.0 Hz), 7.15 (d, 1H, J=8.0 Hz), 7.07 (dd, 1H, J=8.0, 4.8 Hz), 4.38 (s, 2H), 3.86 (s, 2H), 3.61 (t, 2H, J=5.6 Hz), 2.87 (t, 2H, J=5.6 Hz), 2.16 (s, 3H), 1.30 (s, 6H).

Compound 15

[6-(3-Chloro-pyridin-2-yl)-5,6,7,8-tetrahydro-pyrido[4,3-d]pyrimidin-4-yl]-(3,3-dimethyl-2,3-dihydro-1H-indol-6-yl)-amine HCl salt

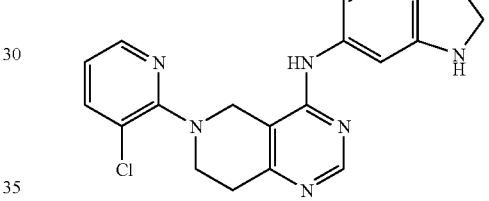

A mixture of 1-{6-[6-(3-chloro-pyridin-2-yl)-5,6,7,8-tetrahydro-pyrido[4,3-d]pyrimidin-4-ylamino]-3,3-dimethyl-2,3-dihydro-indol-1-yl}-ethanone (30 mg), EtOH (5 mL), and 5N aqueous HCl (1 mL) was stirred at 55° C. for 10 h. The mixture was concentrated in vacue to give the HCl salt as a light yellow solid (35 mg).

$^1$H NMR (d6-DMSO): 10.38 (s, 1H), 8.81 (s, 1H), 8.30 (dd, 1H, J=4.8, 1.6 Hz), 7.93 (dd, 1H, J=8.0, 1.6 Hz), 7.55-7.42 (m, 3H), 7.13 (dd, 1H, J=8.0, 4.8 Hz), 4.46 (s, 2H), 3.66 (t, 2H, J=5.6 Hz), 3.48 (s, 2H), 3.06 (t, 2H, J=5.6 Hz), 1.37 (s, 6H).

Compound 16

[6-(3-Chloro-pyridin-2-yl)-5,6,7,8-tetrahydro-pyrido[4,3-d]pyrimidin-4-yl]-(3,3-dimethyl-2,3-dihydro-1-methyl-indol-6-yl)-amine

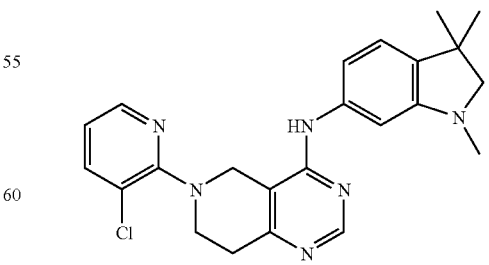

To a stirred mixture of [6-(3-chloro-pyridin-2-yl)-5,6,7,8-tetrahydro-pyrido[4,3-d]pyrimidin-4-yl]-(3,3-dimethyl-2,3-dihydro-1H-indol-6-yl)-amine HCl salt (10 mg), DMF (5 mL), and $K_2CO_3$ (50 mg) was added MeI (50 μL). The reaction mixture was stirred at rt for 5 h, and then diluted with EtOAc (50 mL). The organic phase was washed with brine, dried (Na$_2$SO$_4$) and concentrated. The residue was purified by column to give an off-white solid (7 mg).

$^1$H NMR (d6-DMSO): 8.35 (s, 2H), 8.28 (dd, 1H, J=4.8, 1.6 Hz), 7.88 (dd, 1H, J=8.0, 1.6 Hz), 7.07 (dd, 1H, J=8.0, 4.4 Hz), 6.91 (s, 2H), 6.73 (s, 1H), 4.35 (s, 2H), 3.61 (t, 2H, J=5.6 Hz), 3.03 (s, 2H), 2.86 (t, 2H, J=5.6 Hz), 2.67 (s, 3H), 1.23 (s, 6H).

Compound 17

(6-tert-Butyl-pyridin-3-yl)-[6-(3-chloro-pyridin-2-yl)-5,6,7,8-tetrahydro-pyrido[4,3-d]pyrimidin-4-yl]-amine

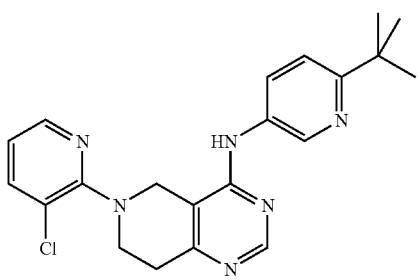

A. (6-Benzyl-5,6,7,8-tetrahydro-pyrido[4,3-d]pyrimidin-4-yl)-(6-tert-butyl-pyridin-3-yl)-amine

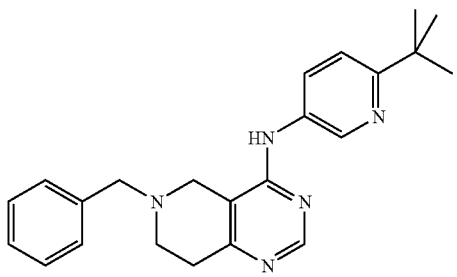

The title compound was prepared substantially according to the procedure given for Compound 1A, using 6-benzyl-4-chloro-5,6,7,8-tetrahydropyrido[4,3-d]pyrimidine (Intermediate 2), and 6-tert-butyl-pyridin-3-ylamine to give the desired N-benzyl intermediate as a brown solid.

B. (5,6,7,8-tetrahydro-pyrido[4,3-d]pyrimidin-4-yl)-(6-tert-butyl-pyridin-3-yl)-amine

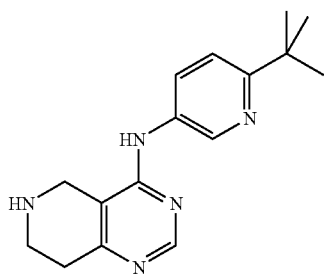

The title compound was prepared substantially according to the procedure given for Compound 1B by deprotection of 6-benzyl-5,6,7,8-tetrahydro-pyrido[4,3-d]pyrimidin-4-yl)-(6-tert-butyl-pyridin-3-yl)-amine.

C. (6-tert-Butyl-pyridin-3-yl)-[6-(3-chloro-pyridin-2-yl)-5,6,7,8-tetrahydro-pyrido[4,3-d]pyrimidin-4-yl]-amine

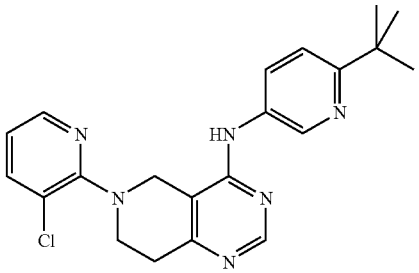

The title compound was prepared according to the procedure given for Compound 1C by reacting (5,6,7,8-tetrahydro-pyrido[4,3-d]pyrimidin-4-yl)-(6-tert-butyl-pyridin-3-yl)-amine with 2,3-dichloropyridine to give the desired compound as an off-white powder.

Compound 18

3,3-Dimethyl-1-{[6-(5-methyl-pyridin-2-yl)-5,6,7,8-tetrahydro-pyrido[4,3-d]pyrimidin-4-ylamino]-methyl}-cyclohexanol

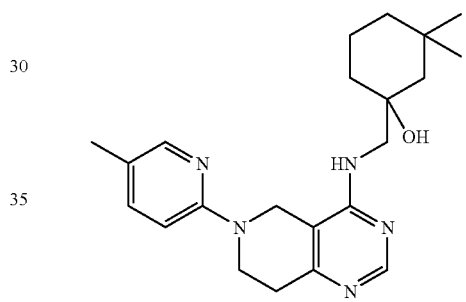

4-chloro-5,6,7,8-tetrahydro-6-(5-methylpyridin-2-yl)pyrido[4,3-d]pyrimidine (0.030 g, 0.00012 mol) and 1-aminomethyl-3,3-dimethyl-cyclohexanol (0.022 g, 0.00014 mol) in acetonitrile (3 mL, 0.06 mol) was heated via microwave in a sealed tube at at 180° C. for a total of 2 hours and five minutes. The reaction mixture was cooled to room temperature and poured into saturated sodium bicarbonate. The mixture was extracted with equal amounts of ethyl acetate and the organic layer was dried over magnesium sulfate. The residue was purified by flash chromatography over silica gel methanol/dichloromethane (0-10%) to yield the title compound.

Compounds 24-33 and 35-129

General Synthesis

Synthesis of amino substituted 5,6,7,8-tetrahydro-6-(5-methylpyridin-2-yl)pyrido[4,3-d]pyrimidine

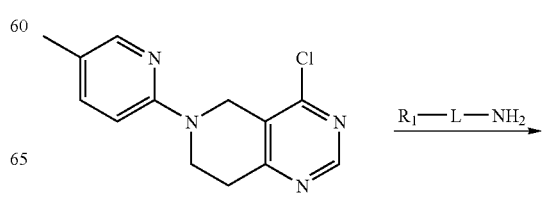

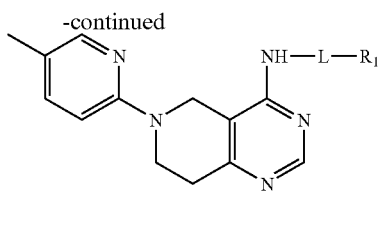

A. 5,6,7,8-Tetrahydro-3H-pyrido[4,3-d]pyrimidin-4-one

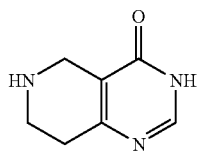

A mixture of 6-benzyl-5,6,7,8-tetrahydropyrido[4,3-d]pyrimidin-4(3H)-one (Intermediate 2, 18.0 g, 0.0738 mol), triethylamine (48 mL, 0.34 mol) Palladium hydroxide (10 g, 0.07 mol) in methanol (242 mL, 5.91 mol) was heated to 60° C. Formic acid (7.6 mL, 0.20 mol) was added dropwise to the mixture over a 15 minute period. The mixture was heated at at 65° C. for three hours, allowed to cool, and filtered over Celite. The filtrate was concentrated under reduced vacuum to yield the title compound as a yellow solid which was used directly in the next reaction. (9.62 g, 77.6%).

MS: M+H=152.2.

B. 5,6,7,8-Tetrahydro-6-(5-methylpyridin-2-yl)pyrido[4,3-d]pyrimidin-4(3H)-one

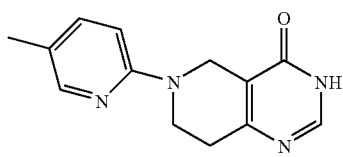

Into a 20 ml microwave tube was combined 5,6,7,8-Tetrahydro-3H-pyrido[4,3-d]pyrimidin-4-one (0.280 g, 0.00183 mol), 2-chloro-5-methylpyridine (0.47 g, 0.0037 mol), 1,4-dioxane (2.5 mL, 0.032 mol) N,N-diisopropylethylamine (0.64 mL, 0.0037 mol) and N,N-dimethylacetamide (0.5 mL, 0.005 mol). The mixture was heated via microwave at 150° C. for 4 hours. The mixture was reduced in vacuo and taken up in chloroform:IPA (3:1) (50 ml). The organic was washed with sodium bicarbonate and brine (1×50 ml), dried over sodium sulfate, and reduced in vacuo. The mixture was purified by flash chromatography on silica gel using a methylene chloride:methanol (0-10%) gradient. The combined pure fractions were reduced in vacuo to yield a bright yellow solid (0.215 g, 47.9%).

MS: M+H=243.28.

$^1$H NMR (DMSO-d6): δ 12.50 (brs, 1H), 8.05 (s, 1H) 7.98 (d, 1H), 7.41 (dd, 1H), 6.84 (d, 1H), 4.24, (s, 2H), 3.77 (t, 2H), 2.67 (t, 2H), 2.15 (s 3H).

C. 4-Chloro-5,6,7,8-tetrahydro-6-(5-methylpyridin-2-yl)pyrido[4,3-d]pyrimidine

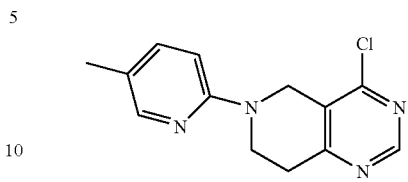

Into a 250 ml round bottom flask was combined 5,6,7,8-tetrahydro-6-(5-methylpyridin-2-yl)pyrido[4,3-d]pyrimidin-4(3H)-one (0.250 g, 0.00103 mol), phosphoryl chloride (0.8 mL, 0.008 mol), and 1,2-dichloroethane (10 mL, 0.1 mol). N,N-Dimethylaniline (0.01 g, 0.0001 mol) was added dropwise and the mixture was heated at reflux for 2 hours. The mixture was reduced in vacuo to yield a dark brown oil. The oil was taken up in methylene chloride (50 ml) and poured over ice. The mixture was carefully neutralized using sat sodium bicarbonate. The layers were separated and the organic was dried over sodium sulfate and reduced in vacuo. The mixture was purified by flash chromatography on silica gel using methylene chloride:methanol (0-10%). The combined pure fractions were reduced in vacuo to yield a bright yellow solid. (0.141 g, 52.4%).

MS: M+H=260.8.

$^1$H NMR (DMSO-d6): δ 8.83 (s, 1H), 8.00 (d, 1H), 7.50 (d, 1H), 6.99 (d, 1H), 4.67 (s, 2H), 3.89 (t, 2H), 2.98 (t, 2H), 2.16 (s, 3H).

D. 4-Substituted amino-5,6,7,8-tetrahydro-6-(5-methylpyridin-2-yl)pyrido[4,3-d]pyrimidine

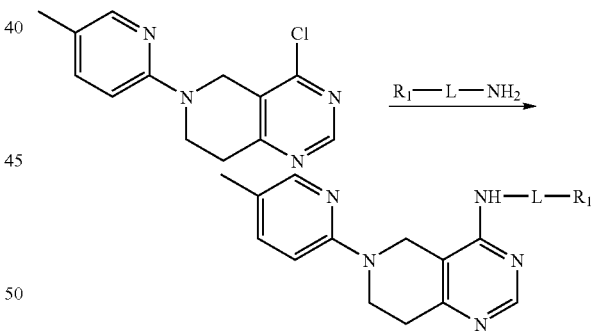

Into a 5 ml microwave reaction tube was combined 4-chloro-5,6,7,8-tetrahydro-6-(5-methylpyridin-2-yl)pyrido[4,3-d]pyrimidine (0.015 mg, 0.05 mmol), benzylamine (1 eq), acetontirile (800 ul) and DIPEA (2.0 eq). The mixture was heated at 150 degrees for 15 minutes. The volatiles were removed under reduced pressure and the mixture was purified by supercritical fluid chromatography to yield the desired product.

The following compounds (24-33 and 35-129) can be prepared substantially according to the procedure given above using 4-chloro-6-(5-methylpyridin-2-yl)-5,6,7,8-tetrahydro-pyrido[4,3-d]pyrimidine and an appropriate amine to give the corresponding amino tetrahydropyrido[4,3-d]pyrimidine derivatives, as shown in Table 1.

TABLE 1

| ID | Amine | Structure |
|---|---|---|
| 24 | 2-Methyl-benzylamine | 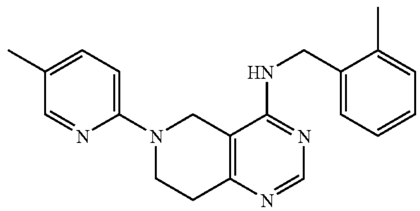 |
| 25 | 4-Chloro-benzylamine | 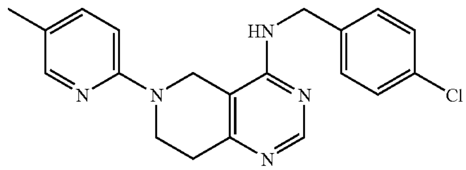 |
| 26 | C-Cyclohexyl-methylamine | 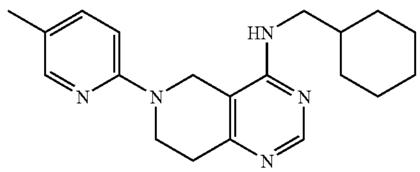 |
| 27 | 2-Methoxy-benzylamine | 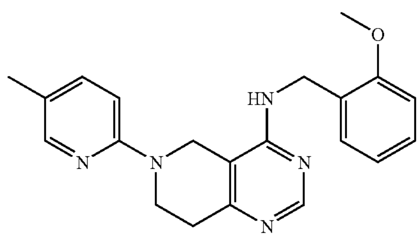 |
| 28 | 3-Methoxy-benzylamine | 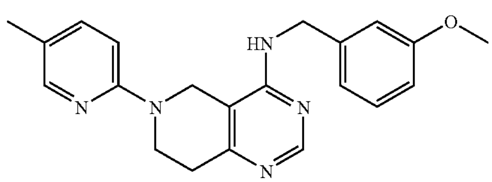 |
| 29 | C-(1-p-Tolyl-cyclohexyl)-methylamine | 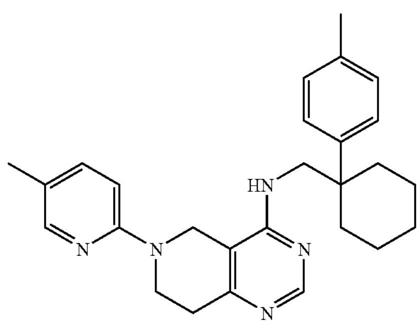 |
| 30 | 2-Chloro-benzylamine | 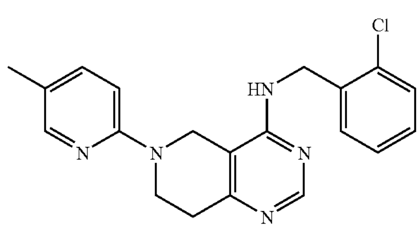 |

TABLE 1-continued

| ID | Amine | Structure |
|---|---|---|
| 31 | 2-Ethoxy-benzylamine | 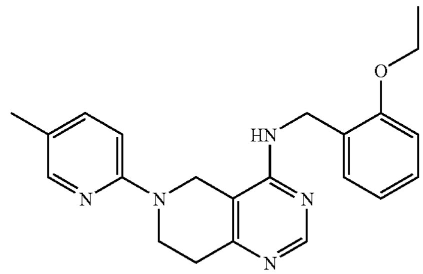 |
| 32 | 2-(2-Chloro-phenyl)-ethylamine | 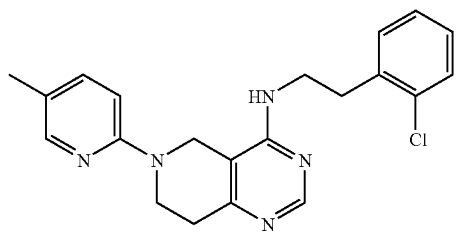 |
| 33 | C-Adamantan-1-yl-methylamine | 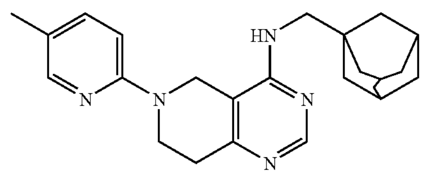 |
| 35 | 2-(4-Methoxy-phenyl)-ethylamine | 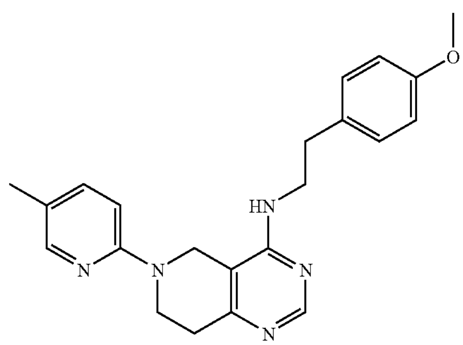 |
| 36 | Benzyl-methyl-amine | 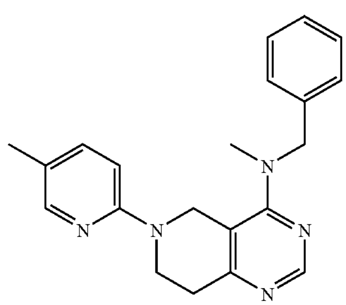 |

TABLE 1-continued

| ID | Amine | Structure |
|---|---|---|
| 37 | C-Benzo[1,3]dioxol-5-yl-methylamine | 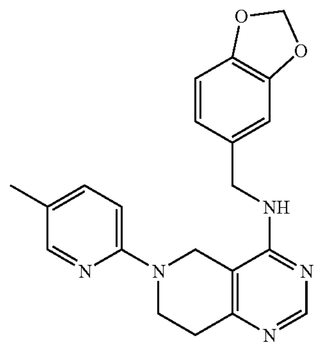 |
| 38 | 3-Trifluoromethyl-benzylamine | 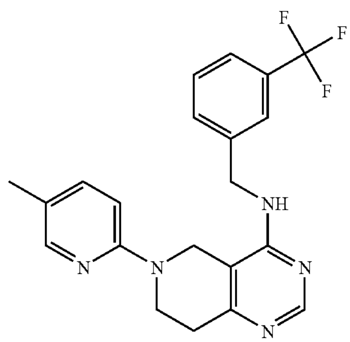 |
| 39 | 2-Trifluoromethyl-benzylamine | 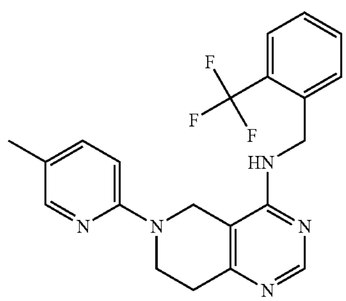 |
| 40 | 4-Trifluoromethoxy-benzylamine | 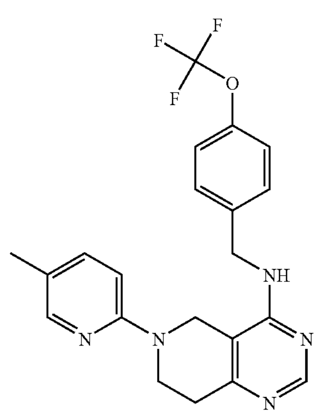 |

TABLE 1-continued
| ID | Amine | Structure |
|----|-------|-----------|
| 41 | 3-Trifluoromethoxy-benzylamine | 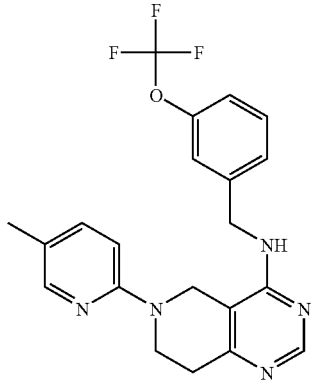 |
| 42 | 2-Trifluoromethoxy-benzylamine | 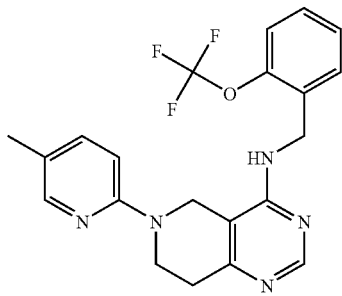 |
| 43 | Indan-1-ylamine | 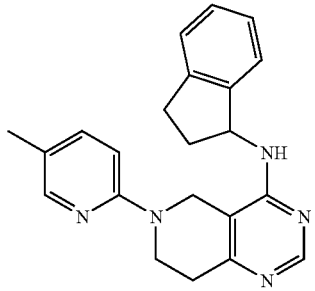 |
| 44 | 4-tert-Butyl-benzylamine | 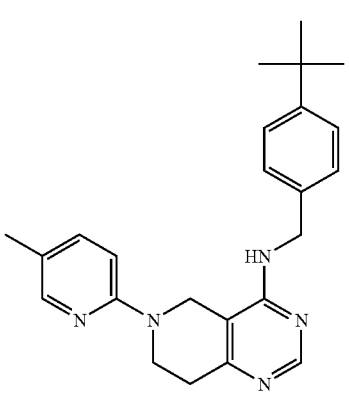 |

TABLE 1-continued
| ID | Amine | Structure |
|---|---|---|
| 45 | Phenethylamine | 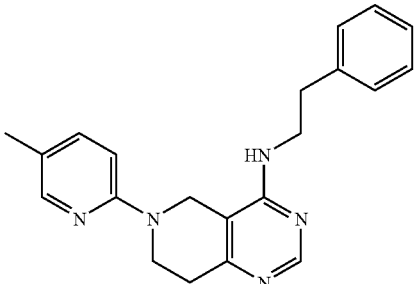 |
| 46 | 2-(3-Methoxy-phenyl)-ethylamine | 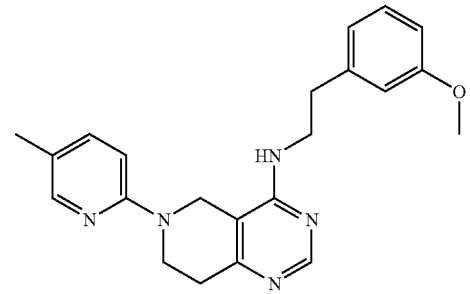 |
| 47 | 2-(3,4-Dimethoxy-phenyl)-ethylamine | 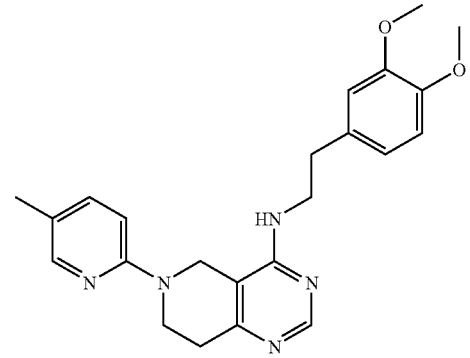 |
| 48 | 2-(4-Chloro-phenyl)-ethylamine | 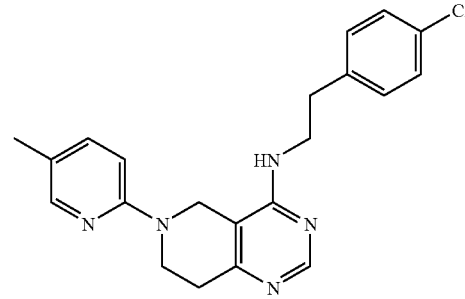 |
| 49 | 2-p-Tolyl-ethylamine | 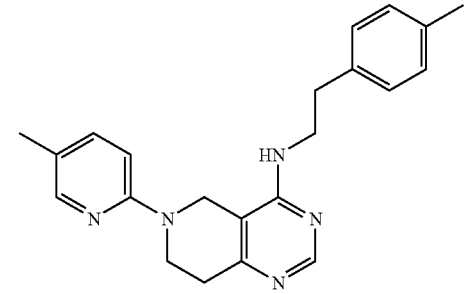 |

TABLE 1-continued
| ID | Amine | Structure |
|---|---|---|
| 50 | 4-Trifluoromethyl-benzylamine | 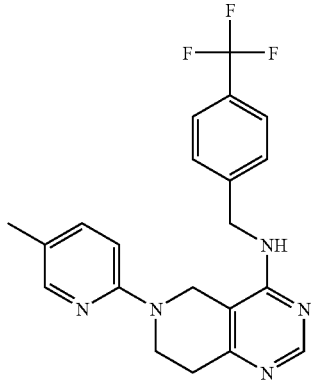 |
| 51 | 2-(3,5-Dimethoxy-phenyl)-ethylamine | 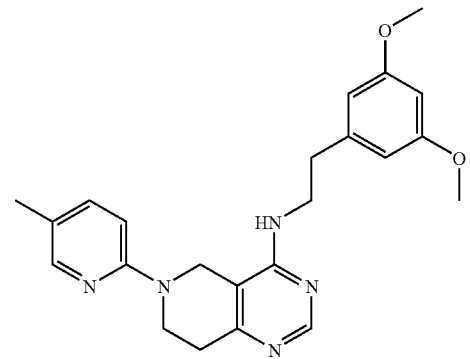 |
| 52 | 2-Difluoromethoxy-benzylamine | 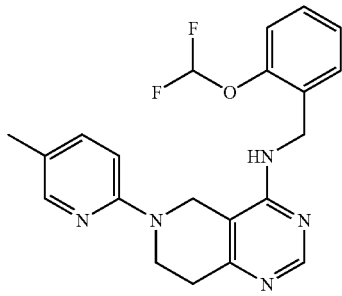 |
| 53 | 4-Methoxy-benzylamine | 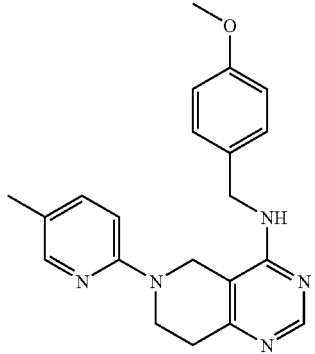 |

TABLE 1-continued

| ID | Amine | Structure |
|----|-------|-----------|
| 54 | 2-(3,4-Dichloro-phenyl)-ethylamine | 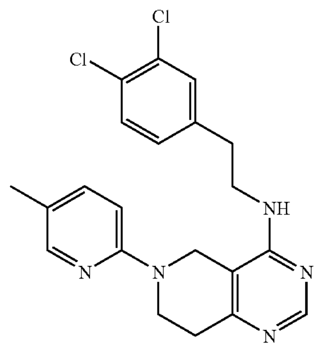 |
| 55 | 3-Chloro-benzylamine | 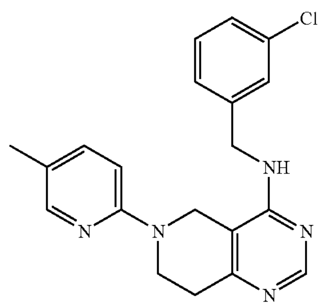 |
| 56 | 4-Methyl-benzylamine | 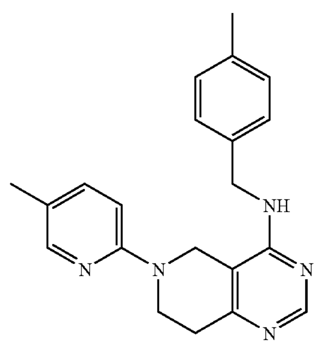 |
| 57 | 3-Fluoro-benzylamine | 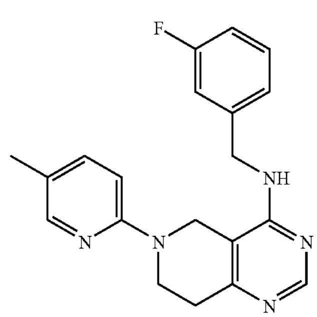 |

TABLE 1-continued
| ID | Amine | Structure |
| --- | --- | --- |
| 58 | 4-Isopropyl-benzylamine | 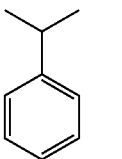 |
| 59 | (3,4-Dimethoxy-benzyl)-methyl-amine | 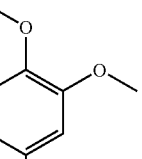 |
| 60 | 2-(4-Fluoro-phenyl)-1,1-dimethyl-ethylamine | 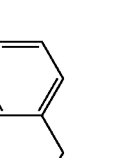 |
| 61 | 2-(3-Trifluoromethyl-phenyl)-ethylamine | 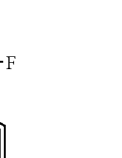 |

TABLE 1-continued

| ID | Amine | Structure |
|---|---|---|
| 62 | (4-Chloro-benzyl)-methyl-amine | 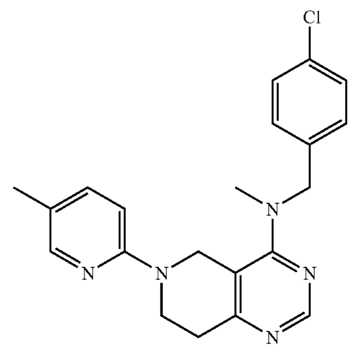 |
| 63 | (2-Methoxy-benzyl)-methyl-amine | 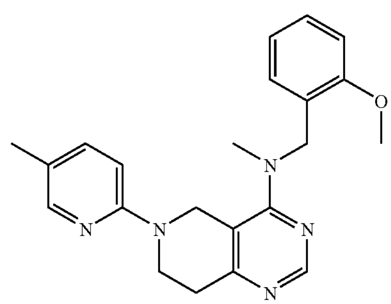 |
| 64 | (3-Methoxy-benzyl)-methyl-amine | 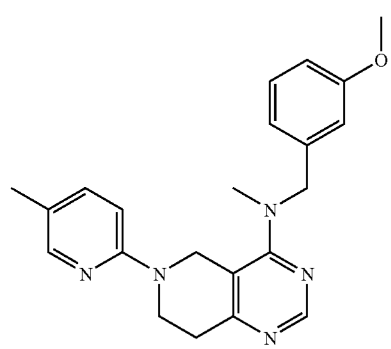 |
| 65 | (4-Ethyl-benzyl)-methyl-amine | 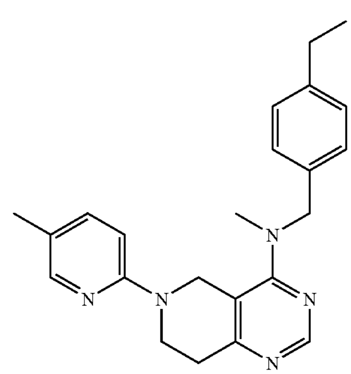 |

TABLE 1-continued

| ID | Amine | Structure |
| --- | --- | --- |
| 66 | (3-Chloro-benzyl)-methyl-amine | 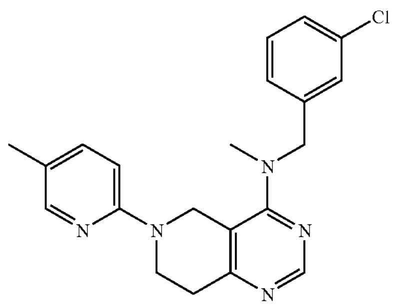 |
| 67 | (4-Fluoro-benzyl)-methyl-amine | 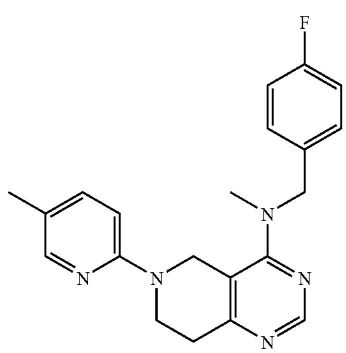 |
| 68 | (4-Methoxy-benzyl)-methyl-amine | 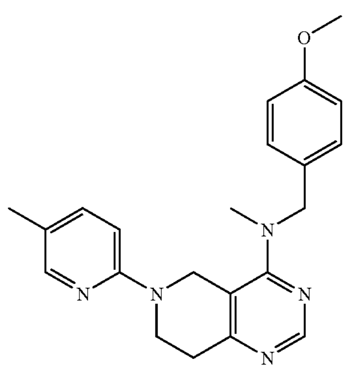 |
| 69 | Methyl-(4-trifluoromethyl-benzyl)-amine | 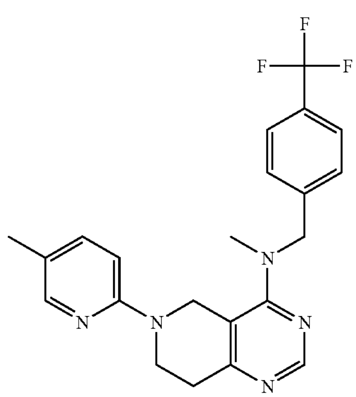 |

TABLE 1-continued

| ID | Amine | Structure |
| --- | --- | --- |
| 70 | Methyl-(4-methyl-benzyl)-amine | 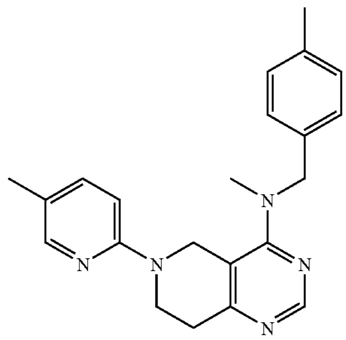 |
| 71 | 2,5-Difluoro-benzylamine | 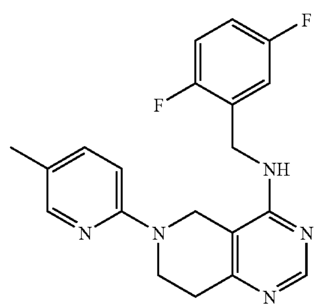 |
| 72 | 2,6-Difluoro-benzylamine | 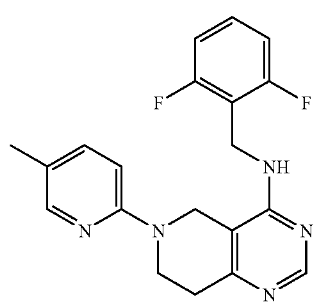 |
| 73 | 3,4-Difluoro-benzylamine | 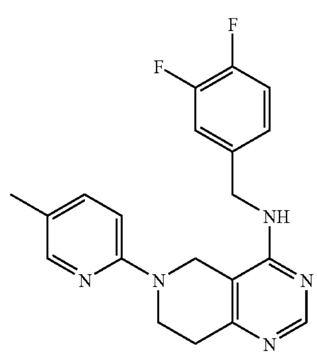 |

TABLE 1-continued

| ID | Amine | Structure |
|---|---|---|
| 74 | 2-Fluoro-5-trifluoromethyl-benzylamine | 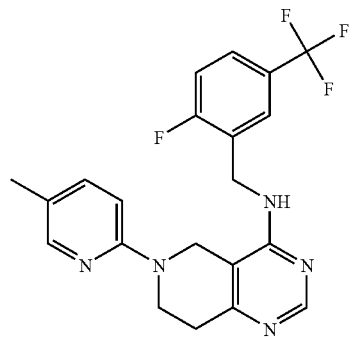 |
| 75 | 3-Fluoro-5-trifluoromethyl-benzylamine | 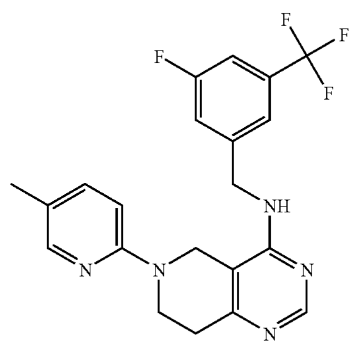 |
| 76 | 4-Fluoro-3-trifluoromethyl-benzylamine | 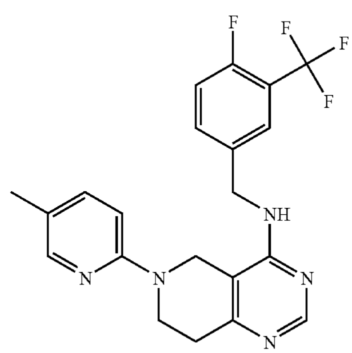 |
| 77 | 2,3-Difluoro-benzylamine | 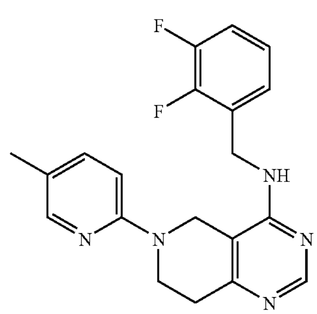 |

TABLE 1-continued

| ID | Amine | Structure |
|----|-------|-----------|
| 78 | 2,4-Dichloro-benzylamine | 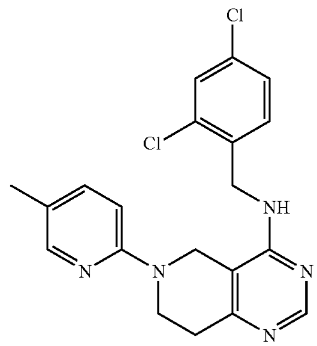 |
| 79 | 2,4-Dimethyl-benzylamine | 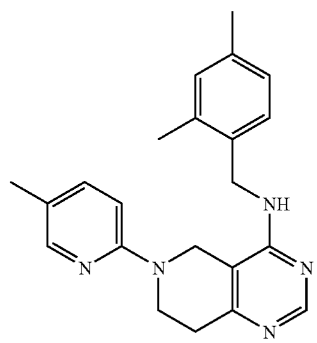 |
| 80 | 2,3-Dimethyl-benzylamine | 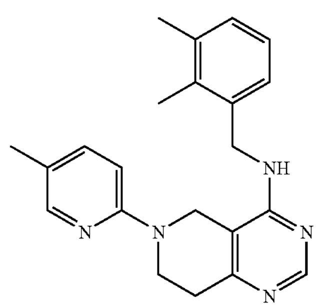 |
| 81 | 1-Methyl-1-phenyl-ethylamine | 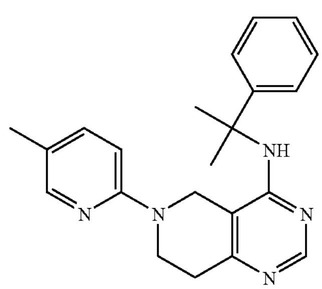 |

TABLE 1-continued

| ID | Amine | Structure |
|---|---|---|
| 82 | 4-Difluoromethoxy-benzylamine | 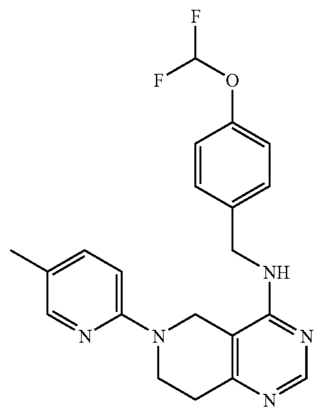 |
| 83 | 4-Chloro-2-fluoro-benzylamine | 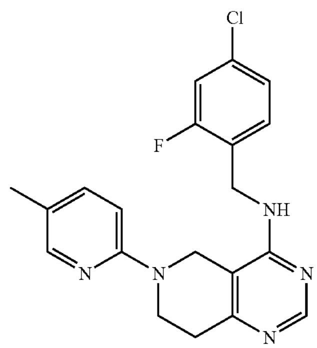 |
| 84 | 3,4-Dimethoxy-benzylamine | 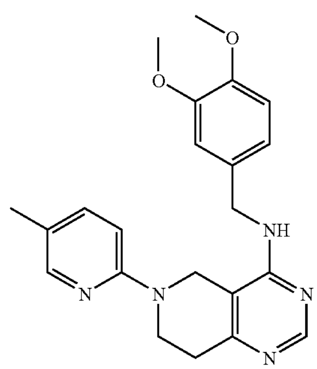 |
| 85 | 3,4-Dichloro-benzylamine | 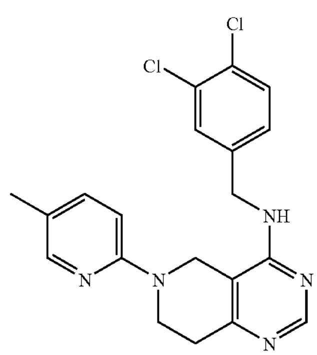 |

TABLE 1-continued

| ID | Amine | Structure |
|---|---|---|
| 86 | 1-(4-Fluoro-phenyl)-ethylamine | 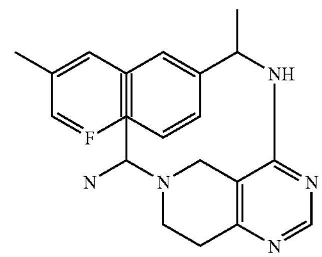 |
| 87 | 3,5-Dimethoxy-benzylamine | 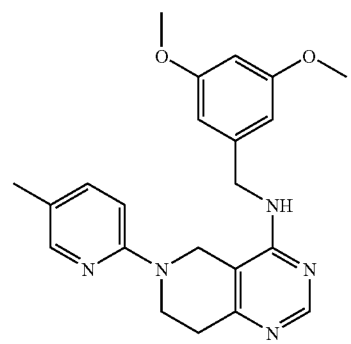 |
| 88 | 2,4-Dimethoxy-benzylamine | 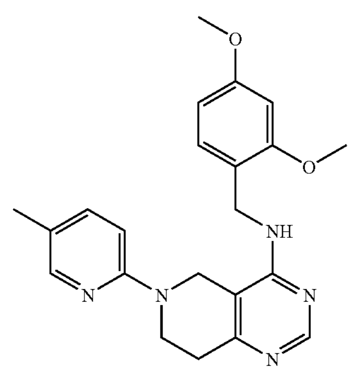 |
| 89 | 2-Chloro-5-trifluoromethyl-benzylamine | 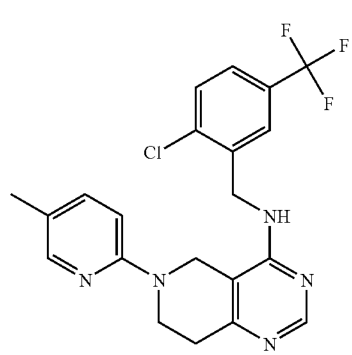 |

TABLE 1-continued
| ID | Amine | Structure |
|----|-------|-----------|
| 90 | C-Pyridin-3-yl-methylamine | 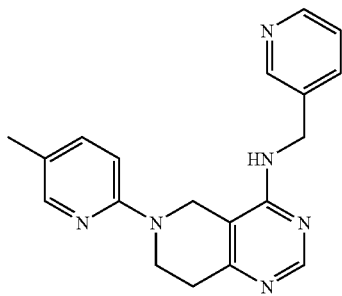 |
| 91 | C-Pyridin-4-yl-methylamine | 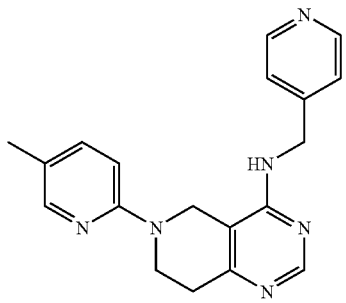 |
| 92 | 3-Methyl-benzylamine | 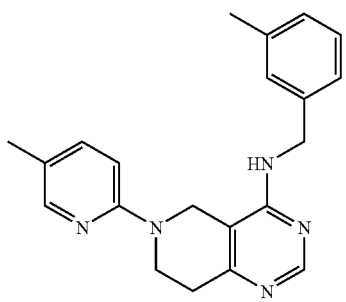 |
| 93 | 4-Fluoro-benzylamine | 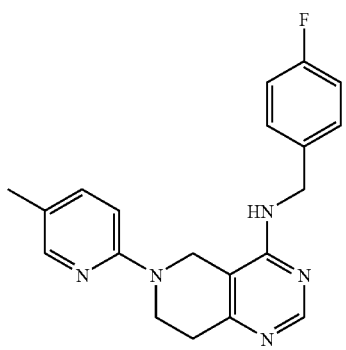 |
| 94 | 3,5-Dimethyl-benzylamine | 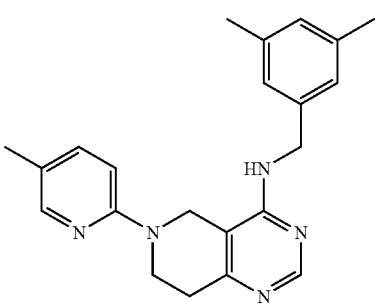 |

TABLE 1-continued

| ID | Amine | Structure |
|---|---|---|
| 95 | 2,5-Dimethyl-benzylamine | 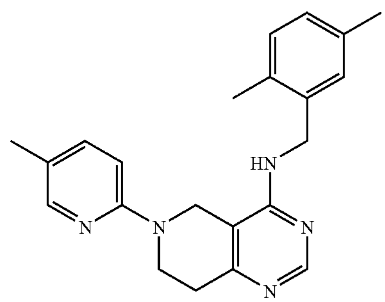 |
| 96 | 3,4-Dimethyl-benzylamine | 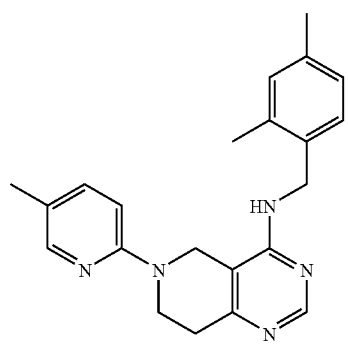 |
| 97 | 4-Ethyl-benzylamine | 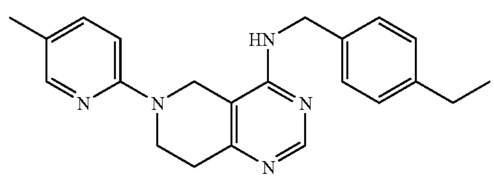 |
| 98 | 4-Fluoro-3-methyl-benzylamine | 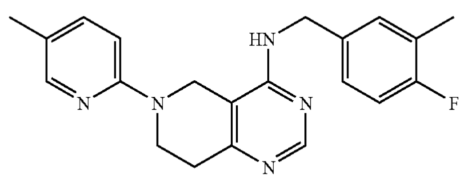 |
| 99 | 1-(3-Fluoro-phenyl-ethylamine | 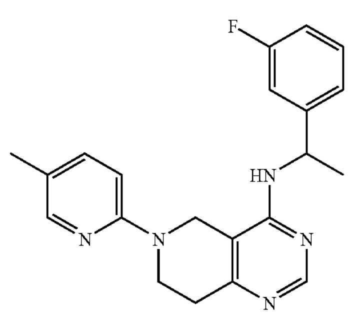 |

TABLE 1-continued
| ID | Amine | Structure |
|---|---|---|
| 100 | 2,4-Difluoro-benzylamine | 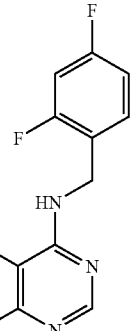 |
| 101 | 3,5-Difluoro-benzylamine | 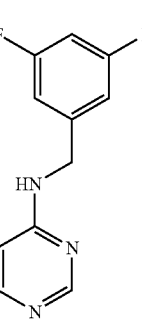 |
| 102 | 4-Chloro-2-methyl-benzylamine | 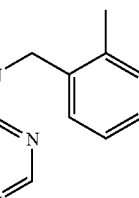 |
| 103 | 5-Chloro-2-methyl-benzylamine | 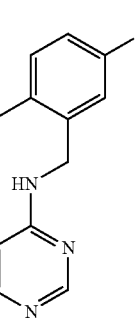 |
| 104 | 3-Chloro-2-methyl-benzylamine | 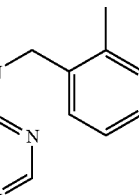 |

TABLE 1-continued

| ID | Amine | Structure |
|---|---|---|
| 105 | 1-(4-Chloro-phenyl)-ethylamine | 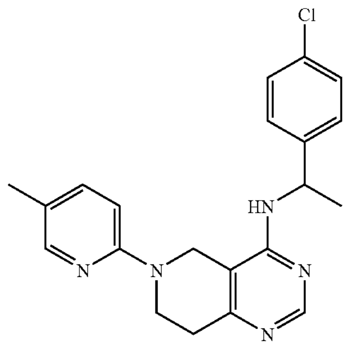 |
| 106 | 2,6-Difluoro-3-methyl-benzylamine | 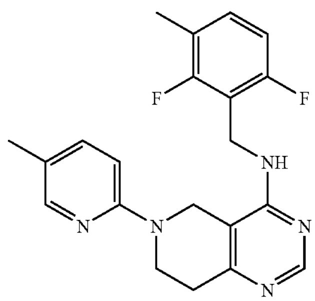 |
| 107 | C-Quinolin-6-yl-methylamine | 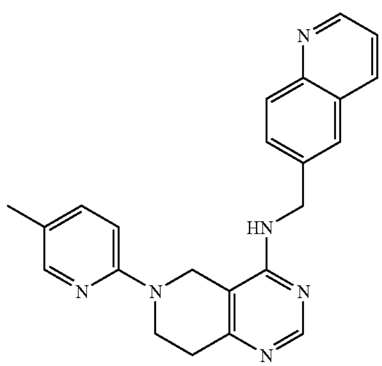 |
| 108 | 4-Chloro-3-fluoro-benzylamine | 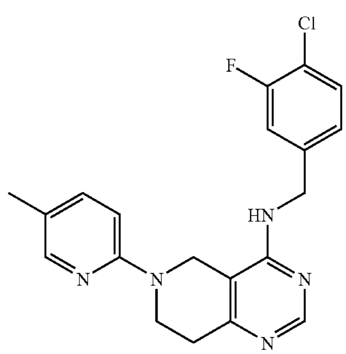 |
| 109 | 2-Chloro-4-fluoro-benzylamine | 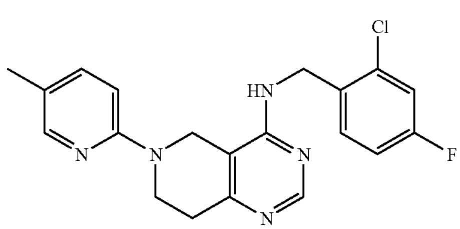 |

TABLE 1-continued
| ID | Amine | Structure |
|---|---|---|
| 110 | 3-Chloro-2-fluoro-benzylamine | 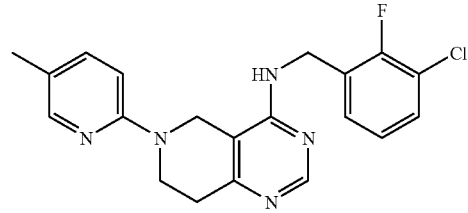 |
| 111 | 5-Chloro-2-fluoro-benzylamine | 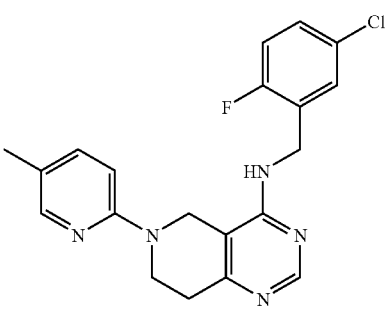 |
| 112 | 3-Chloro-4-fluoro-benzylamine | 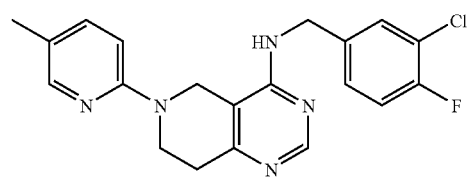 |
| 113 | 2,6-Dimethoxy-benzylamine | 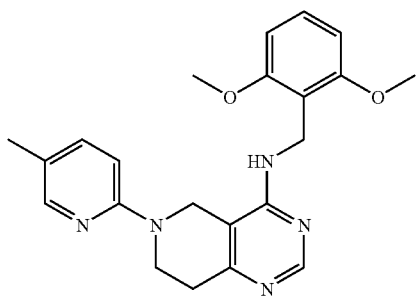 |
| 114 | 2,3-Dimethoxy-benzylamine | 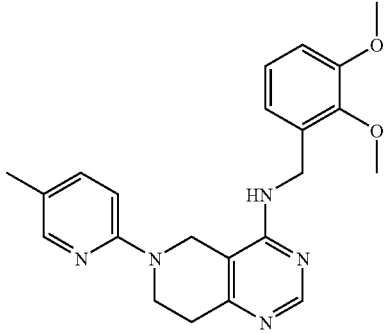 |

TABLE 1-continued
| ID | Amine | Structure |
|---|---|---|
| 115 | 3,5-Dichloro-benzylamine | 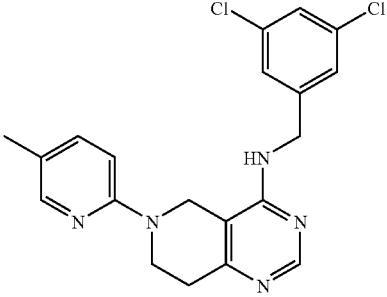 |
| 116 | 2,3-Dichloro-benzylamine | 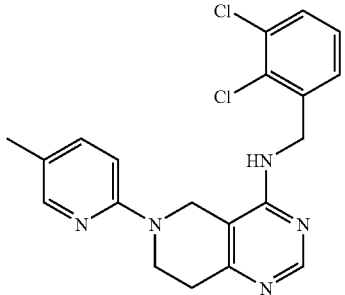 |
| 117 | 1-(3-Trifluoromethyl-phenyl)-ethylamine | 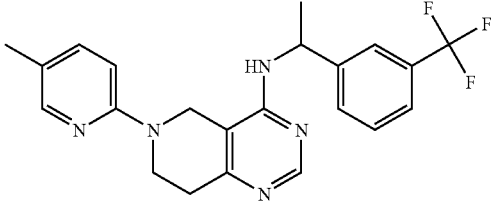 |
| 118 | 4-Fluoro-2-trifluoromethyl-benzylamine | 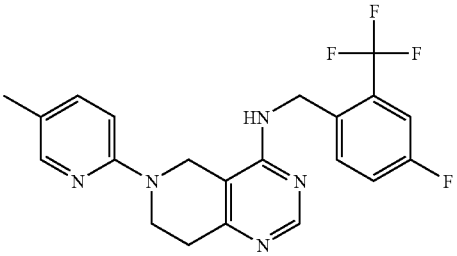 |
| 119 | 5-Fluoro-2-trifluoromethyl-benzylamine | 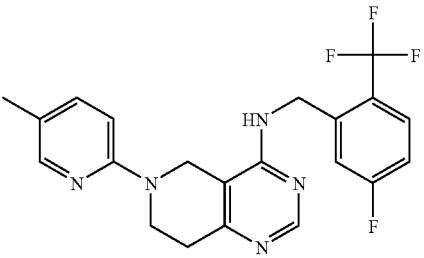 |

TABLE 1-continued

| ID | Amine | Structure |
|---|---|---|
| 120 | 2-Fluoro-3-trifluoromethyl-benzylamine | 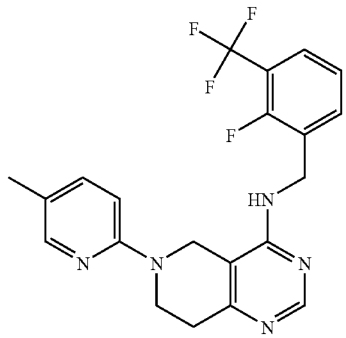 |
| 121 | 2-Fluoro-4-trifluoromethyl-benzylamine | 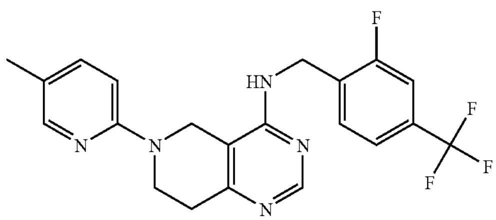 |
| 122 | 3-Fluoro-4-trifluoromethyl-benzylamine | 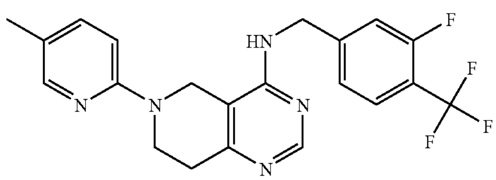 |
| 123 | 1-(4-Methanesulfonyl-phenyl)-ethylamine | 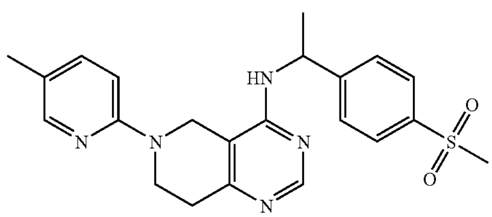 |
| 124 | 3-Phenoxy-benzylamine | 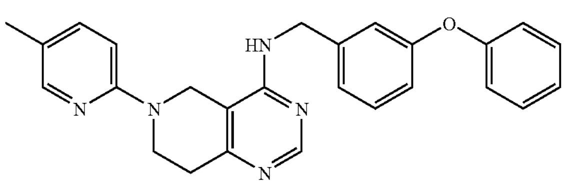 |
| 125 | 3,5-Bis-trifluoromethyl-benzylamine | 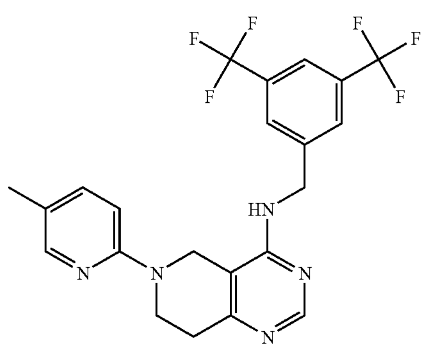 |

TABLE 1-continued

| ID | Amine | Structure |
|---|---|---|
| 126 | 5-Fluoro-2-methyl-benzylamine | 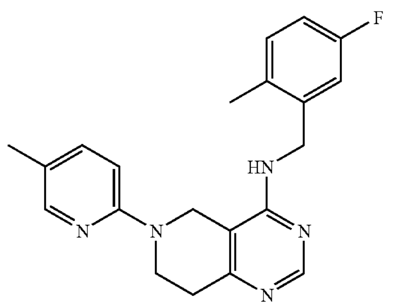 |
| 127 | 4-Chloro-3-trifluoromethyl-benzylamine | 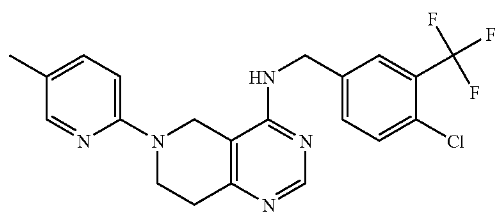 |
| 128 | [(S)-1-(4-Chloro-phenyl)-ethyl]amine | 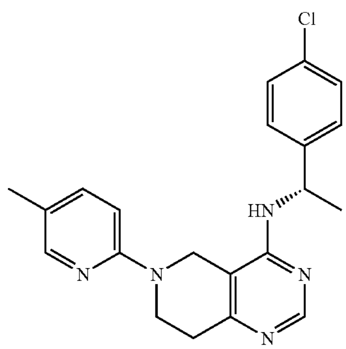 |
| 129 | [(R)-1-(4-Chloro-phenyl)-ethyl]amine | 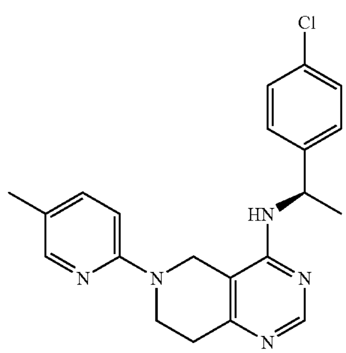 |

Compounds 19, 20 and 22

The following compounds (19, 20 and 22) can be prepared substantially according to the procedure given above using 4-chloro-6-(5-trifluoromethylpyridin-2-yl)-5,6,7,8-tetrahydropyrido[4,3-d]pyrimidine and an appropriate amine to give the corresponding amino tetrahydropyrido[4,3-d]pyrimidine derivatives, as shown in Table 2.

TABLE 2

| ID | Amine | Structure |
|----|-------|-----------|
| 19 | Benzylamine | 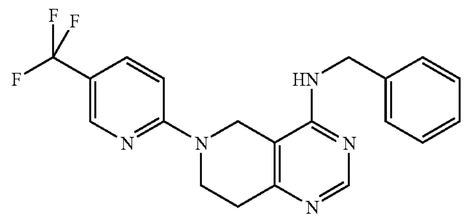 |
| 20 | 2-(2-chloro-phenyl)ethylamine | 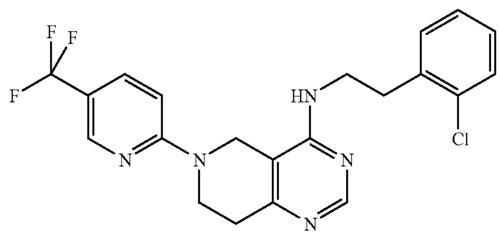 |
| 22 | C-cyclohexyl-methylamine | 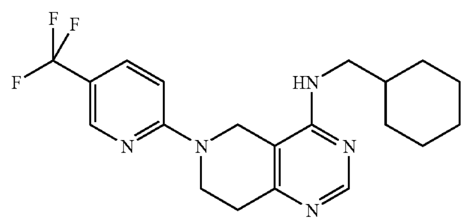 |

Compounds 21 and 23

The following compounds (21 and 23) can be prepared substantially according to the procedure given above using 4-chloro-6-(pyridin-2-yl)-5,6,7,8-tetrahydropyrido[4,3-d]pyrimidine and an appropriate amine to give the corresponding amino tetrahydropyrido[4,3-d]pyrimidine derivatives, as shown in Table 3.

TABLE 3

| ID | Amine | Structure |
|----|-------|-----------|
| 21 | C-cyclo-hexylmethyl amine | 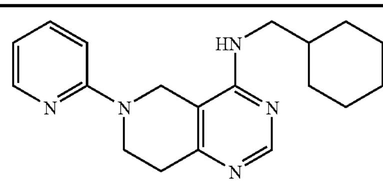 |
| 23 | 2-(2-chloro-phenyl)ethylamine | 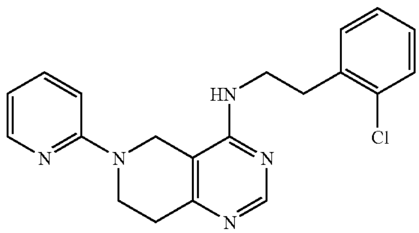 |

Compound 34

6-(3-Chloropyridin-2-yl)-N-(4-(trifluoromethyl)phenyl)-5,6,7,8-tetrahydropyrido[4,3-d]pyrimidin-4-amine

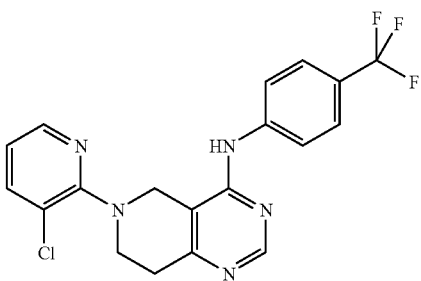

A. 6-Benzyl-N-(4-(trifluoromethyl)phenyl)-5,6,7,8-tetrahydropyrido[4,3-d]pyrimidin-4-amine

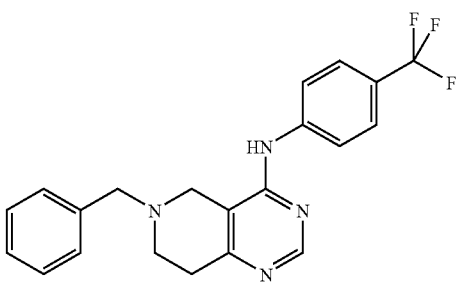

6-Benzyl-4-chloro-5,6,7,8-tetrahydro-pyrido[4,3-d]pyrimidine (0.6 g, 2.3 mmol) was dissolved in anhydrous dioxane (2 mL) and 4-(trifluoromethyl)aniline was added (0.43 mL, 3.45 mmol), followed by HI/H$_2$O (0.2 ml, 47%). The mixture was heated at 130° C. in a sealed tube for 10 min in a microwave (Smith creator model, Personal Chemistry). The solvents were removed under vacuum and the residue was dissolved in ethyl acetate and washed with sat. NaHCO$_3$ and brine. The organic layer was dried over Na$_2$SO$_4$, filtered and evaporated to give the desired compound as a yellow solid (800 mg, 91%) which was used as such for the next step.

M+H=385.

B. N-(4-(Trifluoromethyl)phenyl)-5,6,7,8-tetrahydropyrido[4,3-d]pyrimidin-4-amine

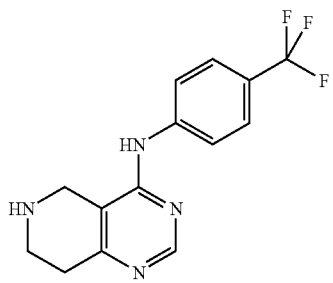

6-Benzyl-N-(4-(trifluoromethyl)phenyl)-5,6,7,8-tetrahydropyrido[4,3-d]pyrimidin-4-amine (1.5 g, 3.9 mmol) was dissolved in methanol (25 mL) and palladium hydroxide was added (1.5 g, 20% wt). The mixture was shaken on a Parr Shaker under H$_2$(g) atmosphere (60 PSI) for 3 days. The mixture was filtered through celite and evaporated to give 1.0 g of material as a yellow solid (87%), which was used as such for the next step.

MS: M+H=295.

$^1$H NMR (DMSO-d6): 8.61 (s, 0.8H), 8.46 (s, 1H), 7.94 (d, 8.6 Hz, 2H), 7.66 (d, 8.6 Hz, 2H), 3.84 (s, 2H), 3.05 (t, 5.6 Hz, 2H), 2.68 (t, 5.6 Hz, 2H).

C. 6-(3-Chloropyridin-2-yl)-N-(4-(trifluoromethyl) phenyl)-5,6,7,8-tetrahydropyrido[4,3-d]pyrimidin-4-amine

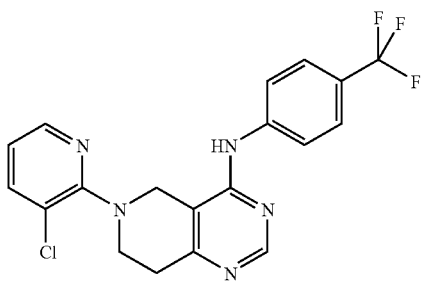

N-(4-(Trifluoromethyl)phenyl)-5,6,7,8-tetrahydropyrido[4,3-d]pyrimidin-4-amine (700 mg, 3.4 mmol) was dissolved in a mixture of dioxane/N,N-dimethylacetamide (4:1) (2 mL). To the mixture was added 2,3-dichloropyridine (1.5 g, 10.2 mmol) and N,N-diisopropylethylamine (0.87 mL, 5.1 mmol). The mixture was heated in a sealed tube at 150° C. in a microwave (Emrys Optimizer model, Personal Chemistry) for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified using a gradient of ethyl acetate:hexane (0-100%) to give the desired compound as an off-white powder (340 mg, 26%).

$^1$H NMR (DMSO-d6 8.91 (brs, 1H). 8.50 (s, 1H), 8.28 (dd, 4.7 Hz, 1.6 Hz, 1H), 7.94 (d, 8.4 Hz, 2H), 7.89 (dd, 7.7 Hz, 1.6 Hz, 1H), 7.67 (d, 8.4 Hz, 2H), 7.08 (dd, 7.6 Hz, 4.7 Hz, 1H), 4.44 (s, 2H), 3.63 (t, 5.6 Hz, 2H), 2.92 (t, 5.6 Hz, 2H).

Assays

Compounds provided herein can be evaluated using biochemical assays, for example, binding assays to purinergic P2X2 and P2X3 receptors, can be evaluated using cell-based assays, or can be evaluated in animal pain models. Examples of assays are described below.

The purinergic receptors P2X2 and P2X3 are expressed in a variety of neuronal and non-neuronal tissues including various sensory and sympathetic ganglia, such as the dorsal root (DRG), nodose (ND), trigeminal (TG), and superior cervical ganglia (SCG) and also in smooth muscle cells (Burnstock, *Trends Pharmacol. Sci.* 27:166-76, 2006). In several regions, P2X2 and P2X3 receptors are coexpressed and functional studies have demonstrated the presence of heteromeric P2X2/3 receptors whose properties differ from those of either homomeric receptor. In addition, chimeric P2X2/3 receptors, containing the N-terminal cytoplasmic domain of P2X2 fused to the first transmembrane domain of P2X3 have been described; these chimeric channels retain the pharmacological profile of homomeric P2X3 receptor, while gaining the non-desensitizing phenotype of the homomeric P2X2 receptor (Neelands et al., *Br. J. Pharmacol.* 140:202-10, 2003). The non-desensitizing behavior of the chimeric receptor is especially useful for screening.

Members of the P2X family are ligand-gated non-selective cation channels whose activity can be characterized by using electrophysiological methods, or by measuring calcium ion influx using calcium-sensitive fluorescent dyes. Applications of agonists such as ATP, or an ATP analog such as α,β-Methyleneadenosine 5'-triphosphate (αβMeATP, Sigma-Aldrich), causes channel opening, resulting in current flow and calcium influx (Bianchi et al., *Eur. J. Pharmacol.* 376:127-38, 1999).

The compounds of the invention can be tested for antagonist activity at P2X3 and P2X2/3 receptors by measuring their ability to affect receptor opening by ATP, αβMeATP, or other agonists. Functional tests of receptor activity include but are not limited to: (i) calcium ion influx measured by fluorescence of a calcium sensitive dye and; (ii) ion flux resulting from channel opening measured by electrophysiological methods. These methods can be used to evaluate channel function when the relevant receptor is heterologously expressed in a mammalian or amphibian cells. These methods can also be used to evaluate compounds of the invention in rodent primary neurons and other mammalian primary cells and cell lines that normally express the receptor of interest.

Compounds can further be evaluated for their ability to bind P2X3 and P2X2/3 receptors using biochemical approaches. Compounds can also be evaluated for their ability to modify sensory and autonomic nervous system signaling where the receptors are known to have a role (e.g., urinary bladder afferent signaling, sensory nerve pain sensation). Finally, compounds of the invention can be tested in vivo in animal pain models known to one skilled in the art, such as, for example, models of neuropathic, inflammatory, or visceral pain, or models of urinary incontinence.

The following biological examples are offered to illustrate the present invention and is not to be construed in any way as limiting in scope thereof.

Calcium Uptake Assay

Clones and Cell Lines:

Human P2X3 (Accession no. NM_002559), P2X2 (Accession no. NM_170682) and Rat P2X3 (Accession no. NM_031075) and P2X2 (Accession no. NM_053656) are cloned into a mammalian expression vector (e.g., pcDNA5/TO or pcDNA3 Invitrogen). For coexpression of P2X2 and P2X3, the coding regions of both receptors were cloned into a bicistronic vector using methods similar to those described by Kawashima et al., Receptors Channels 5:53-60, 1998. The P2X2/3 chimera clone was created as described by Neelands et al, and then cloned into an expression vector as above. Receptors are expressed in cells (e.g., HEK293 or 1321N1) via transient transfection using standard lipid mediated transfection, or by creation of stable transfectants for each receptor. Cell lines are maintained in DMEM+5% Glutamax, the appropriate level of selective antibiotic, and 10% heat inactivated FBS.

P2X Antagonist Assay:

The agonist $EC_{50}$ is determined at the start of the assay and compound $IC_{50}$ experiments are run using a set agonist concentration ($EC_{50-90}$ depending on cell line) as stimulus. The agonists used are αβMeATP, ATP, or other ATP analogs. Compounds may be tested at concentrations ranging from 1 pM to 10 µM. Functional activity of compounds at the P2X receptor is determined by measuring their ability to inhibit agonist-induced calcium influx. Compounds may be tested for antagonist activity against the P2X2/3 chimera, the P2X3 homomer, or the P2X2/3 heteromer. To test for antagonist activity, cells expressing the appropriate receptor are seeded onto 96 or 384 well plates 18-24 hours prior to assay. On the day of the assay, cells are loaded with calcium-sensitive fluorescent dye (e.g., Fluo-4 no wash reagent-Invitrogen cat# F36206, or the BD™ PBX Calcium Assay Kit-BD cat#640175) in Hank's Buffered Salt Solution (HBSS) with up to 10 mM supplemental $CaCl_2$. Plates are incubated at 37° C. and then equilibrated at room temperature. Antagonism of agonist-induced calcium influx is measured using a fluorescent imaging plate reader. The assay comprises two stages: a pre-treatment phase followed by a treatment phase. Compounds may be tested as follows: For the pre-treatment phase, 50 µL of 3× concentration of test compound in HBSS is added to cells containing 100 µL of dye loading media to achieve a final concentration of 1×. For the treatment phase, at a set interval after pre-treatment, 50 µL of 1× test compound plus 4× agonist solution is added to cells. Fluorescence is measured at 0.1-3 second intervals—with an excitation wavelength of 494 nM and an emission wavelength of 515 nM. Responses are measured as peak fluorescence after compound-agonist addition minus baseline fluorescence prior to treatment. Percent inhibition is calculated as follows:

$$\text{Percentage inhibition} = 1 - \frac{(\text{Compound Response} - \text{Control Response})}{(\text{Agonist Response} - \text{Control Response})} \times 100.$$

Electrophysiological Experiments

Whole Cell Patch Clamp:

Whole cell recordings are made using the Multiclamp700A patch-clamp amplifier and Clampex acquisition program (Molecular Devices Corporation). Whole-cell recordings are obtained from stably or transiently transfected 1321N1 or HEK cells. Solutions are either applied for periods of 1 to 3 s by a gravity flow, 8-valve delivery system, or for periods of milliseconds using the quick-change Dynaflow perfusion system (Cellectricon Inc.). The internal pipette solution may include 140 mM Cesium-Chloride, 10 mM EGTA, and 5 mM Hepes at pH 7.2; normal external solution is 140 mM NaCl, 5 mM KCl, 1 mM $CaCl_2$, 2 mM $MgCl_2$, 25 mM Hepes, and 10 mM glucose. Concentration-response curves are obtained by recording currents in response to brief applications of agonist at 1-3 min intervals where regular external solution is perfused during the intervals. To obtain inhibition curves, antagonists are pre-applied to the cells for a defined time period before a short application of the agonist+antagonist. The periods of antagonist pre-application and agonist+antagonist applications are constant for the entire test concentration series. Agonist evoked currents are measured in cells that are voltage clamped at −60 or −80 millivolts.

Oocyte Preparation:

Surgically removed *Xenopus* ovaries are obtained from NASCO. The oocytes are isolated by enzymatic dissociation using collagenase (Worthington, 2 mg/ml). Oocytes are then individually injected with P2X3, P2X2, or a combination of P2X2 and P2X3 RNA. Each oocyte receives ~64 nl of RNA solution in water at a concentration of ~0.01 µg/µl. Injected oocytes are stored in standard oocyte incubation solution, ND96, containing (in mM) 96 NaCl, 2 KCl, 1 $MgCl_2$, 1-5 $CaCl_2$ and 50 µg/ml Gentamicin at 16° C. Agonist-induced-current caused by P2X channel opening is observed in oocytes 1-5 days after injection.

Two-Electrode Voltage Clamp Recording:

Eight oocytes are placed in the recording chambers. Each oocyte is impaled by 2 glass electrodes having resistances of 0.5 to 1 MOhm when filled with a 3 M KCl solution. Electrode advancement and oocyte impalement are under software control (OPUSXPRESS 1.1, Molecular devices Corporation). The solutions are prepared in 96 well plates and robotically pipetted into the oocyte recording chambers by an 8 channel pipettor. Test solution delivery to the oocytes during the experiment is also under software control. A set of plates with wells containing agonist are used initially to verify P2X expression. A set of 96 well plates containing the test solutions is prepared. Inhibition by antagonists is determined by calculating % current remaining when oocytes are stimulated with agonist in the presence of test compound compared to the peak current in the presence of agonist alone. The sequence of solution application to the oocyte is as follows: a specific concentration (e.g., $EC_{50}$, $EC_{80}$, or $EC_{90}$) of the agonist is added first to elicit the maximal response. After the pulse, oocytes are washed for several minutes with ND96. The test compound is then added at a particular concentration, followed by the compound at the same concentration along with the agonist. In one instance, the tested concentrations for the compounds may range from 0.3 to 10,000 nM.

Manual Two-Electrode Voltage Clamp:

Individual oocytes are impaled manually with 2 electrodes and agonist evoked current are measured using an Oocyte clamp amplifier (Warner Instrument Corp.) and Clampex (Molecular Devices Corporation) acquisition software. Solutions are delivered using gravity flow and applied as above. The agonist induced current is measured in the absence and presence of antagonist. Antagonists are tested in a concentration series to obtain an inhibition curve.

Quantitative measurement of P2X current block is done by calculating the area under the curve described by the inward current. The resulting numbers for agonist-induced currents in the presence of increasing compound concentration are normalized to the maximum current obtained. These points are then plotted on a logarithmic scale and fitted by a Hill function. The $IC_{50}$ is calculated from the resulting Hill fit.

Selectivity Screens:

Compounds that inhibit P2X3 and/or P2X2/3H activation will be tested for activity against other P2X receptors to determine their selectivity for specific P2X family members. The list of receptors to be assayed includes, but is not restricted to P2X1, P2X2, P2X4, P2X5, P2X6, and P2X7. The types of assay used for selectivity determination may include: 1) Agonist-induced Calcium influx in cells heterologously expressing the relevant receptor, 2) Electrophysiological determination of receptor inhibition in either mammalian cells or *Xenopus oocytes* heterologously expressing the receptor of interest. Methods and data analysis will be similar to those described above for P2X3 and P2X2/3H.

Radioligand Binding:

Radioligand experiments are done to determine the affinity of test compounds for P2X3 homomeric and P2X2/3 heteromeric receptors. These studies also provide valuable insights into the mechanism of action of antagonism. The general methodologies used for radioligand binding experiments for P2X3 and P2X2/3 receptors are described by Jarvis et al., *J. Pharmacol. Exp. Ther.* 10:407-16, 2004.

Briefly, cell membranes are prepared from cells transiently or stably expressing P2X3 or P2X2/3 receptors. Cells are grown to confluence, washed, isolated, and stored as pellets at −80° C. until use. Some binding studies require the addition Apyrase (Sigma-Aldrich) during membrane preparation to minimize receptor desensitization during membrane preparation. Membranes are prepared by resuspending the cell pellet in homogenization buffer, homogenizing, and centrifuging to obtain a membrane pellet. Total protein concentrations are determined using standard methods.

Displacement binding studies are conducted using procedures adapted from Jarvis et al. Under optimized conditions, ligand competition experiments are conducted using radioligand ([3H]A-317491, Abbott), or other high affinity compounds and a range of different concentrations of test compounds in binding buffer. Ligand saturation studies are conducted using a range of concentrations of radioligand. All binding reactions are terminated by rapid filtration through a glass fiber filter. Membranes are washed, incubated in scintillant, and counted in a scintillation counter. IC50 values are determined using a four-parameter logistic Hill equation.

Bladder Afferent Nerve Recordings:

In order to determine the precise role of inhibition of P2X3 and P2X2/3 receptors in the micturition response, test compounds will be examined for their ability to modulate afferent signaling from the urinary bladder. Compounds will be evaluated in the urinary bladder/pelvic nerve preparation described by Vlaskovska et al., *J. Neuroscience*, 21:5670-7, 2001, and Cockayne et al., *J. Physiol.* 567:621-39, 2005. Briefly, the whole urinary tract attached to the lower vertebrae and surrounding tissues is isolated en bloc and superfused in a recording chamber with oxygenated (5% CO2 and 95% O2) Krebs solution. The bladder is catheterized through the urethra for intraluminal infusion. A second double lumen catheter is inserted into the bladder to measure intraluminal pressure and to drain the bladder. After the bladder is prepared, the pelvic nerve exiting the vertebrae is dissected and impaled with a suction glass electrode. Nerve activity is measured using standard electrophysiological methods. Following a 60 min stabilization period, repeated ramp distensions are performed until the afferent response stabilizes. This stabilized afferent response was used for comparing mechanosensitivity of bladder afferents between different treatment groups.

Drug Metabolism and Pharmacokinetics

Caco-2 Permeability:

Caco-2 permeability is measured according to the method described in Yee, *Pharm. Res.* 14:763-6, 1997. Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media is removed and test compound solution (10 µM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of cumulative appearance of substrate on the receiver side and apparent permeability coefficient (Papp) is calculated from the following equation:

$$Papp(cm/sec) = (F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding:

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet was resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all time. For saturation assays, experiments are conducted in a total volume of 200 µl. Saturation is determined by incubating 20 µl of [$^3$H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration became equal to 1%. Compounds are dispensed in triplicate in assay plates (4 µl). Total binding and nonspecific binding wells are set up in 6 wells as vehicle and 10 µM dofetilide at final concentration, respectively. The radioligand was prepared at 5.6× final concentration and this solution is added to each well (36 µl). The assay is initiated by addition of YSi poly-L-lysine Scintillation Proximity Assay (SPA) beads (50 µl, 1 mg/well) and membranes (110 µl, 20 µg/well). Incubation is continued for 60 min at room temperature. Plates are incubated for a further 3 hours at room temperature for beads to settle. Receptor-bound radioactivity is quantified by counting WALLAC MICROBETA plate counter.

HERG Assay:

HEK 293 cells which stably express the HERG potassium channel are used for electrophysiological study. The methodology for stable transfection of this channel in HEK cells can be found elsewhere (Zhou et al., *Biophys. J.* 74:230-41, 1998). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances >1 GΩ are accepted for further experimentation. Series resistance compensation was applied up to a maximum of 80%. No leak subtraction is done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This was followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there were minimal changes in the amplitude of the evoked current response in the vehicle control condition, the test compound of either 0.3, 1, 3, 10 mM is applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There is a subsequent wash period of a 10-20 min to assess reversibility. Finally, the cells is exposed to high dose of dofetilide (5 mM), a specific IKr blocker, to evaluate the insensitive endogenous current.

All experiments are performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, is measured off line on the computer.

The arithmetic mean of the ten values of amplitude is calculated under vehicle control conditions and in the presence of drug. Percent decrease of IN in each experiment was obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Half-Life in Human Liver Microsomes (HLM):

Test compounds (1 µM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH was added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system. The half-life value is obtained by plotting the natural logarithm of the peak area ratio of compounds/internal standard versus time. The slope of the line of best fit through the points yields the rate of metabolism (k). This is converted to a half-life value using following equation:

$$\text{Half-life} = \ln 2/k.$$

In Vivo Assays:

Various in vivo neuropathic, inflammatory, and visceral pain assays will be conducted in male Sprague-Dawley rats weighing 250-350 g. Test compounds may also be evaluated in models of bladder function. P2X3 antagonists may be administered prior to or post-induction of the pain model depending upon the specific model and the compound PK characteristics. The route of administration may include intraperitoneal, (i.p.), subcutaneous (s.c.), oral (p.o.), intranvenous (i.v.), intrathecal (i.t.), or intraplantar. The endpoints for these studies may include mechanical allodynia, thermal hyperalgesia, cold allodynia, decreased formalin-induced pain responses, decreased writhing and contractions or altered bladder mechanosensation as appropriate for the model as described below.

Neuropathic Pain Models

Chronic Constriction Injury Model (CCI or Bennett Model):

The CCI model is performed according to the method described by Bennett and Xie, *Pain,* 33:87-107, 1988. Briefly, under isoflurane anesthesia, the right sciatic nerve is exposed at mid-thigh level via blunt dissection through the biceps femoris. Proximal to the bifurcation of the sciatic nerve, about 7 mm of nerve is freed of adhering tissue and 4 loose ligatures of 4.0 chromic gut are tied around the nerve. Spacing between ligatures is approximately 1 mm. The wound is closed in layers, and the skin closed with staples or non-silk sutures. Sham operated animals are treated identically with the exception that the sciatic nerve will not be ligated. Mechanical allodynia, cold allodynia, or thermal hyperalgesia testing occur 7-21 days post surgery.

Spinal Nerve Transection (SNT or Chung Model):

The SNT model will be performed according to the method described by Kim and Chung, *Pain* 50:355-363, 1992. Under isoflurane anesthesia, a longitudinal incision is made at the lower lumbar and sacral levels, exposing paraspinal muscles on the left side. The location of the incision is determined by the position of the L5 spinous process. The paraspinal muscles are isolated and removed from the level of the L4 spinous process to the sacrum. This opens up the space ventrolateral to the articular processes, dorsal to the L6 transverse process, and medial to the ileum. Remaining connective tissues and muscles are removed. Under a dissecting microscope, the L6 transverse process, which covers the L5 spinal nerve, is removed. Due to their close proximity, the L4 and L5 spinal nerves may need to be separated to fully expose the L5 spinal nerve for ligation using extra caution not to damage the L4 nerve during this process. Animals that exhibit L4 nerve damage as evidenced by paw drop post-anesthesia are not included in studies. Once the L5 spinal nerve is exposed, the nerve is ligated with 6-0 silk. Alternatively, the spinal nerve is cut distal to the ligation site. If a more complete neuropathy is required, then the L6 spinal nerve may also be ligated using the procedure described above. Sham operated animals are treated identically with the exception that the nerves will not be ligated/transected. Following spinal nerve ligation, hemostasis is confirmed, the muscles are sutured in layers, and the skin is closed with staples or non-silk sutures. Mechanical allodynia, cold allodynia, or thermal hyperalgesia testing occur 7-21 days post surgery.

Chemotherapy-Induced Painful Neuropathy:

Chemotherapy neuropathy is induced by i.p. administration of 1 mg/kg Taxol administered once/day on 4 alternating days (total dose=4 mg/kg) (Polomano et al., *Pain*, 94:293-304, 2001). Mechanical allodynia, cold allodynia, or thermal hyperalgesia testing occur 9-30 days post day 1 of Taxol administration.

Inflammatory Pain Models

Formalin Model:

Test compounds are administered at various times prior to intraplantar administration of formalin. A dilute solution of formalin (50 µL of 2.5% formaldehyde/saline) is administered s.c. into the plantar surface of the left hind paw under light restraint. Immediately following injection, animals are placed on a mesh stand inside a clear observation chamber large enough to allow for free movement of the animals during the study. Behaviors are scored using manual scoring or automated scoring.

Manual scoring: Using a three channel timer, the observer records the time (t in seconds) of decreased weight-bearing ($t_1$), paw lifting ($t_2$), and licking/biting/shaking ($t_3$). Results are weighted according to the method of Dubuisson and Dennis, *Pain*, 4:161-174, 1977, using the formula $t_1+2t_2+3t_3/180$ where 180 s is the evaluation time for each increment. Behaviors are acquired in alternating 3 min increments starting at time=0 min (i.e. 0-3 min, 6-9 min etc.) and ending at 60 min.

Automated scoring: A small metal band weighing 0.5 g is placed on the left paw. Formalin is administered and the animal placed unrestrained inside an observation chamber over an electromagnetic detector system (Automated Nociception Analyzer, University of California, San Diego). The number of paw flinches are electronically recorded.

Complete Freund's Adjuvant Model (CFA):

Animals receive a s.c. injection of 100 µL complete Freund's adjuvant containing 100 µg *Mycobacterium tuberculosis* strain H37Ra into the plantar surface of the right hind paw under isoflurane anesthesia. Swelling and inflammation are visible within 1 h after administration. Mechanical allodynia or thermal hyperalgesia testing start 24 h post CFA administration.

Carageenan:

Animals receive a subcutaneous injection of 100 µL of either 2% carrageenan or saline (controls) into the plantar surface of the right hind paw under isoflurane anesthesia. Swelling and inflammation are visible within 1 h after administration. Mechanical allodynia or thermal hyperalgesia testing start 3-24 h post carageenan administration (Hargreaves et al., *Pain*, 32:77-88, 1988).

ATP and α,β-methylene (αβmeATP) ATP-Induced Inflammatory Pain:

Rats are administered up to 100 nmol αβmeATP, ATP, adenosine, or PBS in a volume up to 100 µL subcutaneously in the plantar surface of the left hindpaw under light restraint. Immediately following injection, animals are placed on a mesh stand inside a clear observation chamber large enough to allow for free movement of the animals. The duration of flinching and licking are recorded over a 4 min interval to evaluate nocifensive behavior. Following nocifensive screening, behavioral testing including measures of mechanical allodynia and thermal hyperalgesia are acquired for up to 6 h post administration.

Visceral Pain Models

Colo-Rectal Distension (CRD):

Prior to induction of the model, animals are deprived of food but allowed access to water ad libitum for 16 h prior to the induction of the model. A 5 cm latex balloon is attached to a barostat system composed of a flow meter and pressure control program by a length of tubing. Under isoflurane anesthesia, the balloon is inserted into the distal colon via the anus at a distance of 5 cm from the anus and taped to the base of the tail. Post-anesthesia, the animal is placed unrestrained into a clean polypropylene cage and allowed to acclimate for 30 mins. The balloon is progressively inflated from 0-75 mmHg in 5 mm increments every 30 s. The colonic reaction threshold is defined as the pressure inducing the first abdominal contraction. Abdominal contraction indicative of visceral pain correlates with hunching, hump-backed position, licking of the lower abdomen, repeated waves of contraction of the ipsilateral oblique musculature with inward turning of the ipsilateral hindlimb, stretching, squashing of the lower abdomen against the floor (Wesselman, *Neurosci. Lett.*, 246:73-76, 1998).

Acetic Acid Writhing Test:

A 0.6% solution of acetic acid (10 ml/kg) is administered i.p. to rats and the number of abdominal constrictions over 30 min are counted.

Behavioral Testing

Mechanical Testing:

Mechanical allodynia testing is performed using the up-down method of Dixon, *Ann. Rev. Pharmacol. Toxicol.* 20:441-462, 1980, modified for mechanical thresholds by Chaplan et al., *J. Neurosci. Methods* 53:55-63, 1994. Testing is performed during the day portion of the circadian cycle (7:00-19:00). Animals are placed in separate plastic enclosures with a mesh bottom which allowed for full access to the paws. For all tests, animals are acclimated to the apparatus for at least 15 min prior to testing or until cage exploration and major grooming activities have ceased. The area tested will be the mid-plantar hind paw. The paw is touched with 1 of a series of 8 von Frey hairs (Stoelting, Wood Dale, Ill.) with logarithmically incremental stiffness (0.4, 0.6, 1.4, 2, 4, 6, 8, and 15 g). Each von Frey hair is presented perpendicularly to the plantar surface with sufficient force to cause slight buckling against the paw and held for approximately 6-8 s. Stimulation is presented at intervals of several seconds, allowing for apparent resolution of any behavioral responses to previous stimuli. A positive response will be noted if the paw was sharply withdrawn. Flinching immediately upon removal of the hair will also be considered a positive response. Ambulation will be considered an ambiguous response and in such cases, the stimulus will be repeated.

To determine the 50% withdrawal threshold, testing will be initiated with the 2 g fiber (the middle fiber in the series). Fibers will be presented in a consecutive fashion whether ascending or descending. In the absence of a paw withdrawal response to the initially selected fiber, the next highest fiber was presented. In the event of a paw withdrawal, the next weaker fiber was presented. The optimal threshold calculation by this method requires 6 responses in the immediate vicinity of the 50% withdrawal threshold. Counting of the critical 6 data points will not begin until the response threshold is first crossed at which time the 2 responses straddling the threshold will be designated as the first 2 responses of the series of 6. Four additional responses to the continued presentation of the fibers constituted the remaining 4 responses.

In cases where continuous positive or negative responses are observed to the exhaustion of the fiber set, values of 15 g and 0.25 g were assigned, respectively.

The range of fibers tested in this paradigm have not been shown to cause tissue damage although prolonged stimulation over short time intervals may result in sensitization and/or habituation, scenarios which would lead to decreased or increased thresholds, respectively. Therefore, there is a minimum 1 h interval between testing sessions with no more than 4 testing sessions per day. For testing intervals, animals are returned to their cages following all testing sessions. Testing sessions will last no longer than 1 h. No two testing sessions will occur on consecutive hours. To minimize distress, mechanical allodynia testing is conducted no more than 4 times per day.

Thermal Testing:

To measure heat thermal hyperalgesia, an Ugo Basile radiant heat source (I.R. intensity of 40) will be provided by a light bulb focused onto the plantar surface of the paw (Hargreaves et al., *Pain* 32:77-88, 1988). Paw withdrawal latencies are defined as the time it takes for the animal to remove its paw from the heat source. To ensure that no tissue damage occurs, all tests will have a 20 sec cutoff even when the animal does not withdraw its paw away from the heat stimulation. The test consists of 3 measurements of the same paw, with a minimum 5 minute intervals between each determination. To minimize distress, thermal testing is conducted no more than 3 times per day.

Cold Testing:

To measure cold allodynia, a drop of acetone is applied to the plantar surface of the paw through the underside of the grating on which the animals are standing using a 50 μL Hamilton syringe. The process is performed 5 times with a 3 min interval between each time. Vigorous shaking will be recorded as a positive response. The acetone drop test is conducted no more than 5 times over the course of a study (including the pre-surgery baseline test) and no more than once per day (Kotinen et al., *Pain* 80:341-346, 1999).

Assays of Urinary Function

Bladder Cystometry:

Animals are anaesthetized, and transurethral closed cystometry was conducted as previously described (Dmitrieva et al., *Neuroscience* 78:449-59, 1997; Cockayne et al., *Nature* 407:1011-5, 2000). The bladder is catheterized cannulated transurethrally with a PE-10 polypropylene catheter. Each cystometrogram consists of slowly filling the bladder with normal saline via the transurethral catheter, and then recording the pressure associated with filling via a pressure transducer. Contractions greater than a predetermined threshold value are interpreted as micturition contractions. For each cystometrogram, the volume at which active contractions occurred (micturition threshold) and the number of contractions per cystometrogram are recorded.

Neuropathic Pain Measurements Using Chung Model

Under pentobarbital anesthesia (60 mg/kg, i.p.), rats are placed in a prone position on a flat, sterile surface. A midline incision from L4-S2 is made and the left paraspinal muscles are separated from the spinous processes. The L5 and L6 spinal nerves are tightly ligated with a 4-0 silicon-treated silk suture, according to the method described by Kim and Chung, *Pain*, 50:355-363, 1992. The L4 spinal nerve is carefully preserved from being surgically injured. The skin is closed with wound clips and animals are returned to their home cages. Rats exhibiting prolonged postoperative neurological deficits or poor grooming are excluded from the experiments. The animals are assessed for response to noxious mechanical stimuli by determining paw withdrawal threshold (PWT), as described below, prior to surgery (baseline), then immediately prior to and at various timepoints after being administered with a fused heterocyclic compound of this invention (30 mg/kg) in the left rear paw of the animal. Additionally, other animals may also be assessed for thermal or mechanical hyperalgesia, as described below.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., *Pain* 32: 77-88, 1988. The maximum exposure time is set at 32 seconds to avoid tissue damage and any directed paw withdrawal from the heat source is taken as the end point. Three latencies are determined at each time point and averaged. Only the affected (ipsilateral) paw is tested. An increase latency of paw withdrawal demonstrates reversal of hyperalgesia.

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in Stein et al., *Pharmacol. Biochem. Behav.* 31:451-455, 1988. The maximum weight that can be applied to the hind paw is set at 250 g and the end point is taken as complete withdrawal of the paw. PWT is determined once for each rat at each time point and only the affected (ipsilateral) paw is tested.

Activity of Compounds of the Invention

A calcium uptake assay was performed as described above under the section, Calcium Uptake, the headings, P2X Antagonist Assay, and Clones and Cell Lines. The % Inhibition data for the representative compounds are given in Table 4 below. In Table 4, activity of each compound is expressed as follows:

TABLE 4

| ID | MW (calcd) | MW (obsd) | Ca Influx P2X2/3C % Inhibition at 3 μM/10 μM |
|---|---|---|---|
| 1 | 403.82 | 403.40 | |
| 2 | 337.81 | 339.20 | +/ |
| 3 | 355.80 | 356.00 | |
| 4 | 406.80 | 407.80 | /* |
| 5 | 450.44 | 450.90 | |
| 6 | 469.87 | 470.20 | +/ |
| 7 | 513.52 | 515.30 | |
| 8 | 374.44 | 374.70 | |
| 9 | 370.38 | 370.60 | |
| 10 | 384.40 | 385.70 | /* |
| 11 | 384.40 | 384.60 | |
| 12 | 384.40 | 385.90 | /* |
| 13 | 420.90 | 421.40 | /* |
| 14 | 448.96 | 449.20 | |
| 15 | 406.92 | 407.40 | /* |
| 16 | 420.95 | 421.50 | +/ |
| 17 | 394.91 | 394.80 | /* |
| 18 | 381.52 | 382.3 | /* |
| 19 | 385.39 | 385.40 | |
| 20 | 433.86 | 433.60 | |
| 21 | 323.44 | 324.30 | |
| 22 | 391.44 | 391.80 | |
| 23 | 365.87 | 366.10 | |
| 24 | 345.45 | 345.80 | /**** |
| 25 | 365.87 | 366.20 | ++++/ |
| 26 | 337.47 | 338.40 | /**** |
| 27 | 361.45 | 362.36 | /**** |
| 28 | 361.45 | 362.35 | ++++/**** |
| 29 | 427.59 | 428.00 | |
| 30 | 365.87 | 366.19 | ++++/ |
| 31 | 375.47 | 375.70 | |
| 32 | 379.89 | 380.30 | ++++/**** |
| 33 | 389.54 | 390.40 | |

TABLE 4-continued

| ID | MW (calcd) | MW (obsd) | Ca Influx P2X2/3C % Inhibition at 3 μM/10 μM |
|---|---|---|---|
| 34 | 405.81 | 406.00 | |
| 35 | 375.47 | 376.36 | ++++/ |
| 36 | 345.45 | 346.24 | +/ |
| 37 | 375.43 | 376.26 | ++++/ |
| 38 | 399.42 | 400.17 | +++/ |
| 39 | 399.42 | 400.18 | +++/ |
| 40 | 415.42 | 416.31 | +++/ |
| 41 | 415.42 | 416.31 | |
| 42 | 415.42 | 416.31 | ++++/ |
| 43 | 357.46 | 358.26 | |
| 44 | 387.53 | 388.40 | +/ |
| 45 | 345.45 | 346.22 | ++++/ |
| 46 | 375.47 | 376.36 | ++++/ |
| 47 | 405.50 | 406.36 | +++/ |
| 48 | 379.89 | 380.30 | ++++/ |
| 49 | 359.47 | 360.29 | ++++/ |
| 50 | 399.42 | 400.17 | ++++/ |
| 51 | 405.50 | 406.35 | +++/ |
| 52 | 397.43 | 398.22 | ++++/ |
| 53 | 361.45 | 362.33 | ++++/ |
| 54 | 414.34 | 414.17 | +++/ |
| 55 | 365.87 | 366.20 | ++++/ |
| 56 | 345.45 | 346.20 | ++++/ |
| 57 | 349.41 | 350.32 | ++++/ |
| 58 | 373.50 | 374.22 | +/ |
| 59 | 405.50 | 406.35 | ++/**** |
| 60 | 391.49 | | |
| 61 | 413.44 | 414.22 | ++++/**** |
| 62 | 379.89 | 380.30 | +/ |
| 63 | 375.47 | 376.35 | +/ |
| 64 | 375.47 | 376.34 | +/ |
| 65 | 373.50 | 374.22 | +/ |
| 66 | 379.89 | 380.30 | +/ |
| 67 | 363.44 | 364.32 | +/*** |
| 68 | 375.47 | 376.35 | +/ |
| 69 | 413.44 | 414.22 | +/ |
| 70 | 359.47 | 360.29 | ++/ |
| 71 | 367.40 | 368.1 | +++/ |
| 72 | 367.40 | | |
| 73 | 367.40 | 367.00 | ++++/ |
| 74 | 417.41 | 417.90 | +/ |
| 75 | 417.41 | 418.4 | +/ |
| 76 | 417.41 | 417.00 | +/ |
| 77 | 367.40 | 368.0 | ++++/ |
| 78 | 400.31 | 400.00 | +/ |
| 79 | 359.47 | 360.4 | ++/ |
| 80 | 359.47 | 360.4 | +/ |
| 81 | 359.47 | | |
| 82 | 397.43 | | |
| 83 | 383.86 | 384.0 | +++/ |
| 84 | 391.47 | 391.00 | |
| 85 | 400.31 | 399.00 | +/ |
| 86 | 363.44 | 363.00 | ++++/ |
| 87 | 391.47 | 392.2 | +/ |
| 88 | 391.47 | 391.00 | |
| 89 | 433.86 | 435.00 | +/* |
| 90 | 332.41 | 333.9 | |
| 91 | 332.41 | 332.00 | |
| 92 | 345.45 | 345.00 | |
| 93 | 349.41 | 349.00 | |
| 94 | 359.47 | 359.00 | |
| 95 | 359.47 | 359.00 | |
| 96 | 359.47 | 359.00 | |
| 97 | 359.47 | 359.00 | |
| 98 | 363.44 | 363.00 | ++++/ |
| 99 | 363.44 | 364.00 | |
| 100 | 367.40 | 367.00 | |
| 101 | 367.40 | 367.00 | |
| 102 | 379.89 | 380.00 | |
| 103 | 379.89 | 379.00 | |
| 104 | 379.89 | 379.00 | |
| 105 | 379.89 | 379.00 | |
| 106 | 381.43 | 381.00 | |
| 107 | 382.47 | 382.00 | |
| 108 | 383.86 | 384.00 | |
| 109 | 383.86 | 384.00 | |

TABLE 4-continued

| ID | MW (calcd) | MW (obsd) | Ca Influx P2X2/3C % Inhibition at 3 μM/10 μM |
|---|---|---|---|
| 110 | 383.86 | 384.00 | |
| 111 | 383.86 | 383.00 | +++/ |
| 112 | 383.86 | 384.00 | |
| 113 | 391.47 | 391.00 | |
| 114 | 391.47 | 391.00 | |
| 115 | 400.31 | 400.00 | +/ |
| 116 | 400.31 | 400.00 | |
| 117 | 413.44 | 414.00 | |
| 118 | 417.41 | 417.00 | |
| 119 | 417.41 | 417.00 | |
| 120 | 417.41 | 417.00 | |
| 121 | 417.41 | 417.00 | ++++/ |
| 122 | 417.41 | 417.00 | |
| 123 | 423.54 | 424.00 | |
| 124 | 423.52 | 423.00 | |
| 125 | 467.42 | 466.00 | +/ |
| 126 | 363.44 | 363.00 | |
| 127 | 433.86 | 433.80 | |
| 128 | 379.89 | 381.8 | |
| 129 | 379.89 | 381.1 | |

+ compound exhibited 0–25% inhibition at 3 μM
++ compound exhibited 25–50% inhibition at 3 μM
+++ compound exhibited 50–75% inhibition at 3 μM
++++ compound exhibited 75% or greater inhibition at 3 μM
* compound exhibited 0–25% inhibition at 10 μM
** compound exhibited 25–50% inhibition at 10 μM
*** compound exhibited 25–50% inhibition at 10 μM
**** compound exhibited 25–50% inhibition at 10 μM.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A compound having a formula 1:

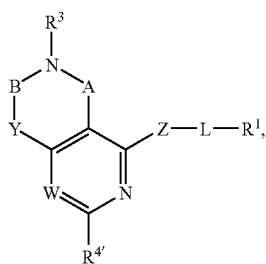

wherein
A and B are independently $CR^{2'}R^{2'}$, CO, or CS;
Y is $CR^{2'}R^{2'}$;
W is N;
Z is O or $NR^2$;
L is a single bond;
$R^1$ is a substituted or unsubstituted carbocyclic group or a substituted or unsubstituted heterocyclic group;
$R^2$ is hydrogen, $C_1$-$C_6$ alkyl, or $C_3$-$C_8$ cycloalkyl;
each $R^{2'}$ is independently hydrogen, $C_1$-$C_6$ alkyl, $C_3$-$C_8$ cycloalkyl, aryl, or aralkyl;
$R^3$ is a carbocyclic group or a heterocyclic group; and
$R^{4'}$ is $R^4$ or —Z'-L'-$R^4$, wherein Z' is a single bond, $NR^{2'}$, O, S, SO, $SO_2$, COO, or $CONR^{2'}$, and L' is ($C_1$-$C_6$)alkylene; and wherein $R^4$ is selected from the group consisting of H, alkyl, —C(O)$R^{20}$, —$NR^{21}$C(O)$R^{22}$, alkylamino, alkylthio, alkoxy, alkoxycarbonyl, alkylarylamino, arylalkyloxy, amino, aryl, arylalkyl, —$SO_2R^{23}$, substituted sulfanyl, aminosulfonyl, arylsulfonyl, dihydroxyphosphoryl, azido, carbamoyl, carboxyl, cyano, cycloalkyl, cycloheteroalkyl, dialkylamino, halo, heteroaryloxy, heteroaryl, heteroalkyl, hydroxy, nitro, and —SH; wherein
$R^{20}$ is hydrogen, alkyl, cycloalkyl, cycloheteroalkyl, aryl, arylalkyl, heteroalkyl, heteroaryl, or heteroarylalkyl;
$R^{21}$ is hydrogen, alkyl, cycloalkyl, cycloheteroalkyl, aryl, arylalkyl, heteroalkyl, heteroaryl, or heteroarylalkyl;
$R^{22}$ is alkyl, alkoxy, cycloalkyl, cycloheteroalkyl, aryl, arylalkyl, heteroalkyl, heteroaryl, or heteroarylalkyl; and
$R^{23}$ is alkyl, aryl, or heteroaryl;
or a pharmaceutically acceptable salt, a stereoisomer, a tautomer or an isotopic variant thereof.

2. A compound having a formula 1:

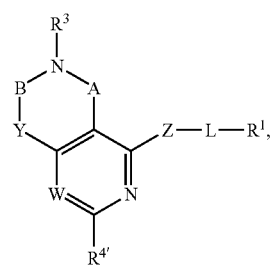

wherein
A and B are independently $CR^{2'}R^{2'}$, CO, or CS;
Y is $CR^{2'}R^{2'}$;
W is N;
Z is O or $NR^2$;
L is substituted or unsubstituted $C_1$-$C_9$ alkylene or substituted or unsubstituted $C_1$-$C_9$ heteroalkylene;
$R^1$ is a substituted or unsubstituted carbocyclic group or a substituted or unsubstituted heterocyclic group;
$R^2$ is hydrogen, $C_1$-$C_6$ alkyl, or $C_3$-$C_8$ cycloalkyl;
each $R^{2'}$ is independently hydrogen, $C_1$-$C_6$ alkyl, $C_3$-$C_8$ cycloalkyl, aryl, or aralkyl;
$R^3$ is substituted or unsubstituted aryl or substituted or unsubstituted heteroaryl; and
$R^{4'}$ is $R^4$ or —Z-L'-$R^4$, wherein Z' is a single bond, $NR^{2'}$, O, S, SO, $SO_2$, COO, or $CONR^{2'}$, and L' is ($C_1$-$C_6$)alkylene; and wherein $R^4$ is selected from the group consisting of H, alkyl, —C(O)$R^{20}$, —$NR^{21}$C(O)$R^{22}$, alkylamino, alkylthio, alkoxy, alkoxycarbonyl, alkylarylamino, arylalkyloxy, amino, aryl, arylalkyl, —$SO_2R^{23}$, substituted sulfanyl, aminosulfonyl, arylsulfonyl, dihydroxyphosphoryl, azido, carbamoyl, carboxyl, cyano, cycloalkyl, cycloheteroalkyl, dialkylamino, halo, heteroaryloxy, heteroaryl, heteroalkyl, hydroxy, nitro, and —SH; wherein
$R^{20}$ is hydrogen, alkyl, cycloalkyl, cycloheteroalkyl, aryl, arylalkyl, heteroalkyl, heteroaryl, or heteroarylalkyl;
$R^{21}$ is hydrogen, alkyl, cycloalkyl, cycloheteroalkyl, aryl, arylalkyl, heteroalkyl, heteroaryl, or heteroarylalkyl;
$R^{22}$ is alkyl, alkoxy, cycloalkyl, cycloheteroalkyl, aryl, arylalkyl, heteroalkyl, heteroaryl, or heteroarylalkyl; and
$R^{23}$ is alkyl, aryl, or heteroaryl;
or a pharmaceutically acceptable salt, a stereoisomer, a tautomer or an isotopic variant thereof.

lamino, halo, heteroaryloxy, heteroaryl, heteroalkyl, hydroxy, nitro, and —SH; wherein $R^{20}$ is hydrogen, alkyl, cycloalkyl, cycloheteroalkyl, aryl, arylalkyl, heteroalkyl, heteroaryl, or heteroarylalkyl;

$R^{21}$ is hydrogen, alkyl, cycloalkyl, cycloheteroalkyl, aryl, arylalkyl, heteroalkyl, heteroaryl, or heteroarylalkyl;

$R^{22}$ is alkyl, alkoxy, cycloalkyl, cycloheteroalkyl, aryl, arylalkyl, heteroalkyl, heteroaryl, or heteroarylalkyl; and $R^{23}$ is alkyl, aryl, or heteroaryl;

or a pharmaceutically acceptable salt, a stereoisomer, a tautomer or an isotopic variant thereof.

3. The compound according to claim 1, wherein L is branched $C_1$-$C_9$ alkylene or substituted $C_1$-$C_9$ alkylene.

4. The compound according to claim 1, wherein L is unsubstituted $C_1$-$C_9$ alkylene.

5. The compound according to claim 1, wherein Z is O.

6. The compound according to claim 1, wherein Z is $NR^2$.

7. The compound according to claim 1, wherein Z is NH.

8. The compound according to claim 1, wherein $R^{4'}$ is H.

9. The compound according to claim 3, having a formula 2:

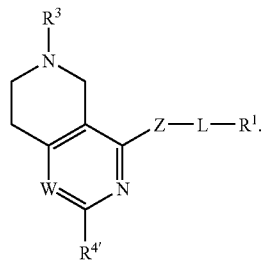

10. The compound according to claim 9, wherein
W is N;
Z is NH; and
$R^{4'}$ is H.

11. The compound according to claim 10, wherein L is selected from the group consisting of —$CH_2$—, —CHMe-, —$CMe_2$-, —$(CH_2)_2$—, —$CMe_2$-$CH_2$—, and —$(CH_2)_3$—.

12. The compound according to claim 10, wherein $R^1$ is aryl, heteroaryl, bicycloaryl, bicycloalkyl, or bicycloheteroaryl.

13. The compound according to claim 10, wherein $R^1$ is substituted or unsubstituted cycloalkyl.

14. The compound according to claim 10, wherein $R^1$ is substituted or unsubstituted quinoline, isoquinoline, methylenedioxyphenyl, or indole.

15. The compound according to claim 10, wherein $R^1$ is

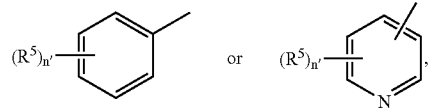

and wherein the subscript n' is 1, 2, 3, 4, or 5, and each $R^5$ is independently selected from the group consisting of hydrogen, substituted or unsubstituted alkyl, —C(O)$R^{20}$, —$NR^{21}$C(O)$R^{22}$, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, —S(O)$R^{24}$, —$SO_2R^{23}$, —$SO_2CF_3$, substituted sulfanyl, substituted or unsubstituted aminosulfonyl, substituted or unsubstituted arylsulfonyl, substituted or unsubstituted dihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and —SH; wherein $R^{20}$ is hydrogen, alkyl, cycloalkyl, cycloheteroalkyl, aryl, arylalkyl, heteroalkyl, heteroaryl, or heteroarylalkyl;

$R^{21}$ is hydrogen, alkyl, cycloalkyl, cycloheteroalkyl, aryl, arylalkyl, heteroalkyl, heteroaryl, or heteroarylalkyl;

$R^{22}$ is alkyl, alkoxy, cycloalkyl, cycloheteroalkyl, aryl, arylalkyl, heteroalkyl, heteroaryl, or heteroarylalkyl;

$R^{23}$ is alkyl, aryl, or heteroaryl; and $R^{24}$ is alkyl, aryl, or heteroaryl.

16. The compound according to claim 15, wherein the subscript n' is 1, 2 or 3.

17. The compound according to claim 15, wherein the subscript n' is 1 or 2.

18. The compound according to claim 15, wherein each $R^5$ is independently selected from the group consisting of Me, Et, Pr, iso-Pr, Ph, Cl, F, Br, CN, OH, OMe, OEt, OPh, COPh, $CO_2Me$, $CH_2$—N-morpholino, $CH_2$—N-(4-Me-piperidino), $CONH_2$, $CF_3$, $CHF_2$, $OCF_3$, $OCHF_2$, t-Bu, SMe, SOMe, $SO_2Me$, $SO_2CF_3$, $SO_2NH_2$, and pyridyl.

19. The compound according to claim 10, wherein $R^3$ is

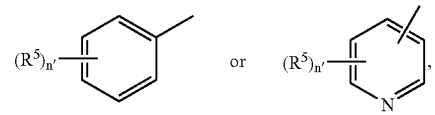

and wherein the subscript n' is 1, 2, 3, 4, or 5, and each of $R^5$ is independently selected from the group consisting of hydrogen, substituted or unsubstituted alkyl, —C(O)$R^{20}$, —$NR^{21}$C(O)$R^{22}$, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, —S(O)$R^{24}$, —$SO_2R^{23}$, —$SO_2CF_3$, substituted sulfanyl, substituted or unsubstituted aminosulfonyl, substituted or unsubstituted arylsulfonyl, substituted or unsubstituted dihydroxyphosphoryl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and —SH; wherein $R^{20}$ is hydrogen, alkyl, cycloalkyl, cycloheteroalkyl, aryl, arylalkyl, heteroalkyl, heteroaryl, or heteroarylalkyl;

$R^{21}$ is hydrogen, alkyl, cycloalkyl, cycloheteroalkyl, aryl, arylalkyl, heteroalkyl, heteroaryl, or heteroarylalkyl;

$R^{22}$ is alkyl, alkoxy, cycloalkyl, cycloheteroalkyl, aryl, arylalkyl, heteroalkyl, heteroaryl, or heteroarylalkyl;

$R^{23}$ is alkyl, aryl, or heteroaryl; and $R^{24}$ is alkyl, aryl, or heteroaryl.

20. The compound according to claim 19, wherein $R^3$ is

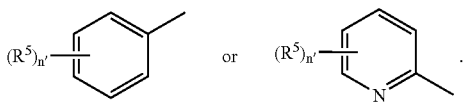

21. The compound according to claim 19 or 20, wherein the subscript n' is 1, 2 or 3.

22. The compound according to claim 19 or 20, wherein the subscript n' is 1 or 2.

23. The compound according to claim 19 or 20, wherein each $R^5$ is independently selected from the group consisting of Me, Et, Pr, iso-Pr, Ph, Cl, F, CN, OH, OMe, OEt, OPh, $CF_3$, $CHF_2$, $OCF_3$, $OCHF_2$, t-Bu, $SO_2Me$, and $SO_2CF_3$.

24. The compound according to claim 10, wherein $R^3$ is

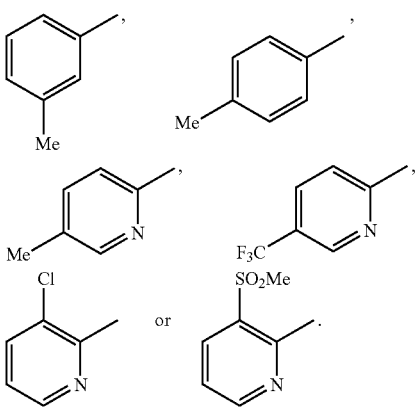

25. The compound according to claim 24, wherein $R^3$ is

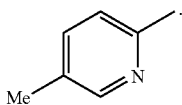

26. The compound according to claim 1, selected from the group consisting of:
(2,3-Difluoro-benzyl)-[6-(5-methyl-pyridin-2-yl)-5,6,7,8-tetrahydro-pyrido[4,3-d]pyrimidin-4-yl]-amine;
(4-Fluoro-3-methyl-benzyl)-[6-(5-methyl-pyridin-2-yl)-5,6,7,8-tetrahydro-pyrido[4,3-d]pyrimidin-4-yl]-amine; and
(2-Fluoro-4-trifluoromethyl-benzyl)-[6-(5-methyl-pyridin-2-yl)-5,6,7,8-tetrahydro-pyrido[4,3-d]pyrimidin-4-yl]-amine;
or a pharmaceutically acceptable salt, a stereoisomer, a tautomer or an isotopic variant thereof.

27. The compound according to claim 1, selected from the group consisting of:
(2-Methyl-benzyl)-[6-(5-methyl-pyridin-2-yl)-5,6,7,8-tetrahydro-pyrido[4,3-d]pyrimidin-4-yl]-amine;
(4-Chloro-benzyl)-[6-(5-methyl-pyridin-2-yl)-5,6,7,8-tetrahydro-pyrido[4,3-d]pyrimidin-4-yl]-amine;
Cyclohexylmethyl-[6-(5-methyl-pyridin-2-yl)-5,6,7,8-tetrahydro-pyrido[4,3-d]pyrimidin-4-yl]-amine;
(2-Methoxy-benzyl)-[6-(5-methyl-pyridin-2-yl)-5,6,7,8-tetrahydro-pyrido[4,3-d]pyrimidin-4-yl]-amine;
(3-Methoxy-benzyl)-[6-(5-methyl-pyridin-2-yl)-5,6,7,8-tetrahydro-pyrido[4,3-d]pyrimidin-4-yl]-amine;
(2-Chloro-benzyl)-[6-(5-methyl-pyridin-2-yl)-5,6,7,8-tetrahydro-pyrido[4,3-d]pyrimidin-4-yl]-amine;
[2-(2-Chloro-phenyl)-ethyl]-[6-(5-methyl-pyridin-2-yl)-5,6,7,8-tetrahydro-pyrido[4,3-d]pyrimidin-4-yl]-amine;
[2-(4-Methoxy-phenyl)-ethyl]-[6-(5-methyl-pyridin-2-yl)-5,6,7,8-tetrahydro-pyrido[4,3-d]pyrimidin-4-yl]-amine;
Benzo[1,3]dioxol-5-ylmethyl-[6-(5-methyl-pyridin-2-yl)-5,6,7,8-tetrahydro-pyrido[4,3-d]pyrimidin-4-yl]-amine;
[6-(5-Methyl-pyridin-2-yl)-5,6,7,8-tetrahydro-pyrido[4,3-d]pyrimidin-4-yl]-(2-trifluoromethoxy-benzyl)-amine;
[6-(5-Methyl-pyridin-2-yl)-5,6,7,8-tetrahydro-pyrido[4,3-d]pyrimidin-4-yl]-phenethyl-amine;
[2-(3-Methoxy-phenyl)-ethyl]-[6-(5-methyl-pyridin-2-yl)-5,6,7,8-tetrahydro-pyrido[4,3-d]pyrimidin-4-yl]-amine;
[2-(4-Chloro-phenyl)-ethyl]-[6-(5-methyl-pyridin-2-yl)-5,6,7,8-tetrahydro-pyrido[4,3-d]pyrimidin-4-yl]-amine;
[6-(5-Methyl-pyridin-2-yl)-5,6,7,8-tetrahydro-pyrido[4,3-d]pyrimidin-4-yl]-(2-p-tolyl-ethyl)-amine;
[6-(5-Methyl-pyridin-2-yl)-5,6,7,8-tetrahydro-pyrido[4,3-d]pyrimidin-4-yl]-(4-trifluoromethyl-benzyl)-amine;
(2-Difluoromethoxy-benzyl)-[6-(5-methyl-pyridin-2-yl)-5,6,7,8-tetrahydro-pyrido[4,3-d]pyrimidin-4-yl]-amine;
(4-Methoxy-benzyl)-[6-(5-methyl-pyridin-2-yl)-5,6,7,8-tetrahydro-pyrido[4,3-d]pyrimidin-4-yl]-amine;
(3-Chloro-benzyl)-[6-(5-methyl-pyridin-2-yl)-5,6,7,8-tetrahydro-pyrido[4,3-d]pyrimidin-4-yl]-amine;
(4-Methyl-benzyl)-[6-(5-methyl-pyridin-2-yl)-5,6,7,8-tetrahydro-pyrido[4,3-d]pyrimidin-4-yl]-amine;
(3-Fluoro-benzyl)-[6-(5-methyl-pyridin-2-yl)-5,6,7,8-tetrahydro-pyrido[4,3-d]pyrimidin-4-yl]-amine;
[6-(5-Methyl-pyridin-2-yl)-5,6,7,8-tetrahydro-pyrido[4,3-d]pyrimidin-4-yl]-[2-(3-trifluoromethyl-phenyl)-ethyl]-amine;
(3,4-Difluoro-benzyl)-[6-(5-methyl-pyridin-2-yl)-5,6,7,8-tetrahydro-pyrido[4,3-d]pyrimidin-4-yl]-amine; and
[1-(4-Fluoro-phenyl)-ethyl]-[6-(5-methyl-pyridin-2-yl)-5,6,7,8-tetrahydro-pyrido[4,3-d]pyrimidin-4-yl]-amine;
or a pharmaceutically acceptable salt, a stereoisomer, a tautomer or an isotopic variant thereof.

28. A pharmaceutical composition comprising a pharmaceutically acceptable carrier and a pharmaceutically effective amount of the compound of claim 1.

29. The pharmaceutical composition of claim 28, wherein the carrier is a parenteral carrier.

30. The pharmaceutical composition of claim 28, wherein the carrier is an oral carrier.

31. The pharmaceutical composition of claim 28, wherein the carrier is a topical carrier.

* * * * *